US011491147B2

(12) United States Patent
Zhang et al.

(10) Patent No.: US 11,491,147 B2
(45) Date of Patent: Nov. 8, 2022

(54) COMBINATION DRUG THERAPY REDUCES PARP-1 RELATED DNA REPAIR AND INCREASES THE EFFICACY OF GENOTOXIC AGENTS

(71) Applicant: Indiana University Research and Technology Corporation, Indianapolis, IN (US)

(72) Inventors: Jian-Ting Zhang, Carmel, IN (US); Jian-Yuan Liu, Carmel, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 16/339,042

(22) PCT Filed: Oct. 3, 2017

(86) PCT No.: PCT/US2017/054950
§ 371 (c)(1),
(2) Date: Apr. 3, 2019

(87) PCT Pub. No.: WO2018/067575
PCT Pub. Date: Apr. 12, 2018

(65) Prior Publication Data

US 2019/0350912 A1 Nov. 21, 2019

Related U.S. Application Data

(60) Provisional application No. 62/403,423, filed on Oct. 3, 2016.

(51) Int. Cl.
*A61K 31/4439* (2006.01)
*A61P 35/00* (2006.01)
(Continued)

(52) U.S. Cl.
CPC ........ *A61K 31/4439* (2013.01); *A61K 31/137* (2013.01); *A61K 31/4184* (2013.01);
(Continued)

(58) Field of Classification Search
CPC .............. A61K 2300/00; A61K 31/137; A61K 31/337; A61K 31/4184; A61K 31/4439;
(Continued)

(56) References Cited

U.S. PATENT DOCUMENTS

2004/0014694 A1* 1/2004 Chakroun ............ A61K 31/337 514/34
2009/0227633 A1* 9/2009 Damaj .................... A61P 35/02 514/338

FOREIGN PATENT DOCUMENTS

WO WO-2015134790 A1 * 9/2015 ........... C07D 277/40

OTHER PUBLICATIONS

Fako et al. (Journal of Medicinal Chemistry, 2015, 58, 778-784) (Year: 2015).*

(Continued)

*Primary Examiner* — Savitha M Rao
(74) *Attorney, Agent, or Firm* — Faegre Drinker Biddle & Reath LLP

(57) ABSTRACT

Various aspects and embodiments disclosed herein relate generally to the modelling, treatment, reduction of resistance to the treatment, prevention, and/or diagnosis of diseases characterized by the formation of cancers. Embodiments include methods of treating cancer, comprising the steps of: providing a patient diagnosed with cancer with a therapeutic regime that includes at least one therapeutically effective dose of at least one agent that reduces the activity of at least one DNA damage/repair pathway. Other embodiments include methods of treating cancer, comprising the steps of: treating a patient diagnosed with cancer with a combination (Continued)

A
M/Vec M/FASN M3K/Scr M3K/Sh
FASN
Actin

B
M/Vec
M/FASN
RRF
BLEO CDDP DOX $H_2O_2$ IR UVB

M3K/Scr
M3K/Sh
RRF
BLEO CDDP DOX $H_2O_2$ IR UVB of therapeutic agents that includes at least one therapeutically effective anti-cancer agent and at least one compound that reduces the activity of at least one DNA damage/repair pathway. Yet other embodiments include methods of reducing resistance to a genotoxic therapeutic, comprising the steps of: treating a patient at least one therapeutically effective dose of at least one agent that reduces at least one DNA damage/repair pathway.

12 Claims, 29 Drawing Sheets

Specification includes a Sequence Listing.

(51) Int. Cl.

| | |
|---|---|
| ***A61K 31/137*** | (2006.01) |
| ***A61K 31/4184*** | (2006.01) |
| ***A61K 31/454*** | (2006.01) |
| ***A61K 31/502*** | (2006.01) |
| ***A61K 31/5025*** | (2006.01) |
| ***A61K 31/55*** | (2006.01) |

(52) U.S. Cl.

CPC .......... *A61K 31/454* (2013.01); *A61K 31/502* (2013.01); *A61K 31/5025* (2013.01); *A61K 31/55* (2013.01); *A61P 35/00* (2018.01); *A61K 2300/00* (2013.01)

(58) Field of Classification Search

CPC ................ A61K 31/454; A61K 31/502; A61K 31/5025; A61K 31/55; A61K 31/555; A61K 31/675; A61K 33/243; A61P 35/00

See application file for complete search history.

(56) References Cited

OTHER PUBLICATIONS

Weil et al. ( Curr Probl Cancer2011: 35 (1)-pp. 1-29) (Year: 2011).*

Sohn et al. (Clinical Pharmacology and therapeutics , vol. 61, No. 5. 1997, pp. 574-582) (Year: 1997).*

Song et al. (Current therapeutic research, vol. 70, 3, 2009 (pp. 228-239) (Year: 2009).*

Spugnini, et al. “Lansoprazole as a rescue agent in chemoresistant tumors: a phase I/II study in companion animals with spontaneously occurring tumors,” The Journal of Translational Medicine, 2011, col. 9, No. 221, 29 pages.

International Search Report and Written Opinion issued by the European Patent Office, dated Dec. 29, 2017, for International Patent Application No. PCT/US2017/054950; 10 pages.

International Preliminary Report on Patentability issued by the International Searching Authority, dated Apr. 18, 2019, for International Patent Application No. PCT/US2017/054950; 8 pages.

Wikipedia page for “Proton-pump inhibitor” (available at https://en.wikipedia.org/wiki/Proton-pump_inhibitor).

Damaghi et al., 4 Front Physiol. 370 (2013).

Sardesai, et al., 27 Clin. Cancer. Res. 5810 (2021).

Wang et al., 509 Cancer Lett. 1 (2021).

* cited by examiner

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Primer for PARP-1

<400> SEQUENCE: 1

cccagggtct tcggatag                                                   18


<210> SEQ ID NO 2
<211> LENGTH: 20
<212> TYPE: DNA
```

-continued

```
<213> ORGANISM: Artificial Sequence
<220> FEATURE:
<223> OTHER INFORMATION: Primer for PARP-1

<400> SEQUENCE: 2

agcgtgcttc agttcataca                                               20


<210> SEQ ID NO 3
<211> LENGTH: 20
<212> TYPE: DNA
<213> ORGANISM: Artificial Sequence
<220> FEATURE:
<223> OTHER INFORMATION: Primer for PARP-1 promoter

<400> SEQUENCE: 3

ccgggtcctc caaagagcta                                               20


<210> SEQ ID NO 4
<211> LENGTH: 21
<212> TYPE: DNA
<213> ORGANISM: Artificial Sequence
<220> FEATURE:
<223> OTHER INFORMATION: Primer for PARP-1 promoter

<400> SEQUENCE: 4

gccgttccct gatagattgc t                                             21


<210> SEQ ID NO 5
<211> LENGTH: 100
<212> TYPE: DNA
<213> ORGANISM: Homo sapiens

<400> SEQUENCE: 5

cgcccgggaa actccgcccc ccggccggca gggggcgcgc gcgccgccgg ccccgccccg      60

tggacgcggg ttccgtgggc gttcccgcgg ccaggcatca                          100
```

COMBINATION DRUG THERAPY REDUCES PARP-1 RELATED DNA REPAIR AND INCREASES THE EFFICACY OF GENOTOXIC AGENTS

CROSS-REFERENCE TO RELATED APPLICATIONS

This application is a 35 U.S.C. § 371 national phase of Serial No. PCT/US2017/054950, filed Oct. 3, 2017, which claims the benefit of U.S. Provisional Application No. 62/403,423, filed on Oct. 3, 2016, the entire disclosure of which is hereby expressly incorporated by reference herein.

STATEMENT OF GOVERNMENTAL RIGHTS

This invention was made with government support under W81XWH-16-1-0030 awarded by U.S. Army Medical Research & Material Command. The government has certain rights in the invention.

FIELD OF THE INVENTION

Various aspects and embodiments disclosed herein relate generally to the modelling, treatment, reducing resistance to the treatment, prevention, and diagnosis of diseases characterized by the formation of cancers.

BACKGROUND AND SUMMARY

Fatty acid synthase (FASN) is a key mammalian enzyme required for de novo synthesis of palmitate. FASN expression and activity is largely suppressed by sufficient dietary fat in most normal non-adipose tissues, but abnormally elevated in many human cancer cells elevated level of activity of this enzyme in cancer cells is associates with poor prognosis. FASN's association with poor prognosis may derive in part from FASN functioning to elevate in drug resistance during chemotherapy. Indeed, it has been found that FASN expression and/or activity was increased in drug-selected and resistant breast and pancreatic cancer cells. It was also found that FASN over-expression causes cellular resistance to DNA-damaging drugs such as doxorubicin and mitoxantrone but not to microtubule modulators such as vinblastine and paclitaxel. Decreased ceramide production following doxorubicin treatment via suppressing tumor necrosis factor (TNF)-α production was believed to be one of the mechanisms of FASN-induced resistance to doxorubicin.

The observation that FASN increases resistance to genotoxic drugs prompted an investigation to determine if FASN over-expression may up-regulate DNA damage response/repair pathways. As reported herein this hypothesis was tested with a focus on repair of DNA double strand breaks (DSBs), which are thought to be induced by anticancer drugs such as doxorubicin, mitoxantrone, and ionizing radiation. In mammalian cells, DSBs are repaired mainly via homologous recombination (HR) and non-homologous end-joining (NHEJ) pathways. NHEJ is the predominant form of DSB repair because it appeasrs to occur during all phases of cell cycle while HR only initiates at the late G1 and S phases. NHEJ repair of DSB was studied and it was found that FASN up-regulates NHEJ activity and repair of DSB by increasing PARP-1 expression via increasing the expression of specific protein 1 (SP1) and reducing the expression of NF-κB which bind to the same composite element in the PARP-1 promoter. Furthermore, lipid-deprivation suppresses SP1 expression, which could be rescued by palmitate supplementation. These findings indicated that FASN may up-regulate DNA repair mechanisms by increasing PARP-1 expression via NF-κB and SP1, which in turn contributes to cellular resistance to genotoxic anticancer treatments. Thus, lipid metabolism likely plays an important role in cancer cell survival against genotoxic insults by regulating DNA repair pathways.

The findings disclosed herein reveals a potential molecular pathway on how FASN causes drug and radiation resistance and contributes to poor clinical prognosis of cancer diseases. FASN is the sole cytosolic enzyme responsible for de novo lipid synthesis, required for cancer cell survival but not for most normal non-adipose tissues. The finding that FASN regulates DNA repair by regulating SP1 and NF-κB in cancer cell response to anticancer treatments will have profound impact on designing treatment strategies. It also helps establish FASN as a target for therapeutic discovery to sensitize drug and radiation resistance. FASN is crucial for cancer cell survival and associates with poor prognosis. FASN over-expression has been found to cause resistance to genotoxic insults. Here, it was found that FASN suppresses NF-κB but increases SP1 expression. NF-κB and SP1 bind to a composite element in the PARP-1 promoter in a mutually exclusive manner and regulate PARP-1 expression. Up-regulation of PARP-1 by FASN in turn increases Ku protein recruitment and DNA repair. Furthermore, lipid-deprivation suppresses SP1 expression, which could be rescued by palmitate supplementation. However, lipid deprivation or palmitate supplementation had no effect on NF-κB expression. Thus, FASN may regulate NF-κB and SP1 expression using different mechanisms. While not wishing to be bound by this theory, FASN may regulate cellular response against genotoxic insults by up-regulating PARP-1 and DNA repair via NF-κB and SP1.

A first embodiment includes a method of treating cancer, steatosis, and/or diabetes, comprising the steps of: providing a patient diagnosed with cancer, steatosis, and/or diabetes with a therapeutic regime that includes at least one therapeutically effective dose of at least one agent that reduces the activity of at least one DNA damage/repair pathway. Some embodiments include a composition for use in treating cancer, steatosis, and/or diabetes comprising at least one therapeutically effective dose of at least one agent that reduces the activity of at least one DNA damage/repair pathway.

A second embodiment includes the method and/or the composition of the first embodiment, wherein the at least one agent that reduces the activity of the at least one DNA damage/repair pathway comprises a fatty acid synthase (FASN) inhibitor, a poly ADP ribose polymerase (PARP) inhibitor, a specific protein 1 (SP1) inhibitor, FASN siRNA, PARP siRNA, and/or SP1 siRNA.

A third embodiment includes the method and/or the composition of any one of the first and the second embodiments, wherein the therapeutic regime further includes comprises at least one proton pump inhibitor.

A fourth embodiment includes the method and/or the composition of any one of the first to the third embodiments, wherein the at least one agent is a proton pump inhibitor (PPI) selected from the group consisting of: omeprazole, PRILOSEC®, lansoprazole, PREVACID®, dexlansoprazole, DEXILENT®, rabeprazole, ACIPHEX®, pantoprazole, PROTONIX®, esomeprazole, NEXIUM®, and ZEGARID®, anaprazole, tenatoprazole, ilaprozole, and/or metabolites thereof, and/or R- or S-enantiomers thereof, and/or a pharmaceutically acceptable salt thereof.

A fifth embodiment includes the method and/or the composition of any one of the first to the fourth embodiments, wherein the at least one agent that reduces the activity of the at least one DNA damage/repair pathway is a poly ADP ribose polymerase (PARP) inhibitor selected from the group consisting of: olaparib, niraparib, iniparib, talazoparib, veliparib, and rucaparib.

A sixth embodiment includes a method of treating cancer, steatosis, and/or diabetes, comprising the steps of: treating a patient diagnosed with cancer, steatosis, and/or diabetes with a combination of therapeutic agents that includes at least one therapeutically effective anti-cancer agent and at least one compound that reduces the activity of at least one DNA damage/repair pathway. Some embodiments include a composition for use in treating cancer, steatosis, and/or diabetes comprising at least one therapeutically effective anti-cancer agent and at least one compound that reduces the activity of at least one DNA damage/repair pathway.

A seventh embodiment includes the method and/or the composition of the sixth embodiment, in which the at least one compound that reduces the up-regulation of a DNA damage/repair pathway acts by reducing the activity of PARP-1 and/or by affecting the activity of NF-κB pathway and/or SP1 activity.

An eighth embodiment includes the method and/or the composition of any one of the sixth and the seventh embodiments, in which the at least one compound that reduces the activity of the DNA damage repair activity comprises a fatty acid synthase (FASN) inhibitor, a poly ADP ribose polymerase (PARP) inhibitor, a specific protein 1 (SP1) inhibitor, FASN siRNA, PARP siRNA, and/or SP1 siRNA.

A ninth embodiment includes the method and/or the composition of any one of the sixth to the eighth embodiments, in which the combination of therapeutic agents further includes at least one proton pump inhibitor.

A tenth embodiment includes the method and/or the composition of any one of the sixth to the ninth embodiments, wherein the at least one agent is a proton pump inhibitor selected from the group consisting of: omeprazole, PRILOSEC®, lansoprazole, PREVACID®, dexlansoprazole, DEXILENT®, rabeprazole, ACIPHEX®, pantoprazole, PROTONIX®, esomeprazole, NEXIUM®, and ZEGARID®, anaprazole, tenatoprazole, ilaprozole, and/or metabolites thereof, and/or R- or S-enantiomers thereof, and/or a pharmaceutically acceptable salt thereof.

An eleventh embodiment includes the method and/or the composition of any one of the sixth to the tenth embodiments, in which the at least one agent reduces the activity of the DNA damage/repair pathway is a poly ADP ribose polymerase inhibitor selected from the group consisting of: olaparib, niraparib, iniparib, talazoparib, veliparib, rucaparib, and/or metabolites thereof, and/or R- or S-enantiomers thereof, and/or a pharmaceutically acceptable salt thereof.

A twelfth embodiment includes the method and/or the composition of any one of the sixth to the eleventh embodiments, wherein the at least one anti-cancer treatment induces DNA double strand breaks (DSBs).

A thirteenth embodiment includes the method and/or the composition of any one of the sixth to the twelfth embodiments, wherein the at least one anti-cancer treatment comprises treatments with doxorubicin, bleomycin, vinblastine, paclitaxel, mitoxantrone, cisplatine, $H_2O_2$, UVB, ionizing radiation, and/or DNA-damaging radiotherapy.

A fourteenth embodiment includes a method of reducing resistance to a genotoxic therapeutic, comprising the steps of: treating a patient at least one therapeutically effective dose of at least one agent that reduces at least one DNA damage/repair pathway. Some embodiments include a composition for use in reducing resistance to a genotoxic therapeutic comprising at least one therapeutically effective dose of at least one agent that reduces at least one DNA damage/repair pathway.

A fifteenth embodiment includes the method and/or the composition of the fourteenth embodiment, wherein the at least one agent comprises a fatty acid synthase (FASN) inhibitor, a proton pump inhibitor (PPIs), a poly ADP ribose polymerase (PARP) inhibitor, a specific protein 1 (SP1) inhibitor, FASN siRNA, PARP siRNA, and/or SP1 siRNA.

A sixteenth embodiment includes the method and/or the composition of any one of the fourteenth and the fifteenth embodiments, further includes administering at least one proton pump inhibitor to the patient.

A seventeenth embodiment includes the method and/or the composition of any one of the fourteenth to the sixteenth embodiments, in which the at least one proton pump inhibitor is selected from the group consisting of: omeprazole, PRILOSEC®, lansoprazole, PREVACID®, dexlansoprazole, DEXILENT®, rabeprazole, ACIPHEX®, pantoprazole, PROTONIX®, esomeprazole, NEXIUM®, and ZEGARID®, anaprazole, tenatoprazole, ilaprozole, and/or metabolites thereof, and/or R- or S-enantiomers thereof, and/or a pharmaceutically acceptable salt thereof.

An eighteenth embodiment includes the method and/or the composition of any one of the fourteenth to the seventeenth embodiments, wherein the at least one agent is a poly ADP ribose polymerase (PARP) inhibitor selected from the group consisting of: olaparib, niraparib, iniparib, talazoparib, veliparib, and rucaparib.

A nineteenth embodiment includes the method and/or the composition of any one of the fourteenth to the eighteenth embodiments, wherein the genotoxic therapy induces DNA double strand breaks (DSBs).

A twentieth embodiment includes the method and/or the composition of any one of the fourteenth to the nineteenth embodiments, wherein the at least one genotoxic therapy is selected from the group consisting of: doxorubicin, bleomycin, vinblastine, paclitaxel, mitoxantrone, cisplatine, $H_2O_2$, UVB, ionizing radiation and DNA-damaging radiotherapy. Some embodiments include the method of any one of the preceding embodiments, wherein the patient is treated with chemotherapy or hormonal therapy.

A twenty first embodiment includes the method and/or the composition of any one of the preceding embodiments, wherein the at least one therapeutically effective anti-cancer agent includes at least one agent comprising a DNA-damaging drug, a cross-linker, an anthracycline, an antimitotic, an anti-metabolite, an ER antagonist and/or agonist, a GnRH antagonist and/or agonist, an aromatase inhibitor, and/or a HER2 inhibitor. Some embodiments include the method of any one of the preceding embodiments, wherein the patient includes humans, animals, and/or tissues thereof, and/or cells thereof.

A twenty second embodiment includes the method and/or the composition of any one of the preceding embodiments, wherein the at least one therapeutically effective anti-cancer agent includes at least one agent comprising a DNA-damaging drug, a cross-linker, an anthracycline, an antimitotic, an ER antagonist and/or agonist, an aromatase inhibitor, and/or a HER2 inhibitor.

A twenty third embodiment includes the method and/or the composition of any one of the twenty first and twenty second embodiments, wherein the at least one therapeutically effective anti-cancer agent includes at least one agent comprising carboplatin, cisplatin, cyclophosphamide, epirubicin, doxorubicin, liposomal doxorubicin, docetaxel, paclitaxel, vinorelbine, capecitabine, gemcitabine, fluorouracil, methotrexate, fulvestrant, tamoxifen, goserelin, leuprolide, anastrozole, exemestane, letrozole, trastuzumb, and/or metabolites thereof, and/or a pharmaceutically acceptable salt thereof.

A twenty fourth embodiment includes the method and/or the composition of any one of the twenty first and twenty second embodiments, wherein the at least one therapeutically effective anti-cancer agent includes at least one agent comprising carboplatin, cisplatin, cyclophosphamide, epirubicin, doxorubicin, liposomal doxorubicin, docetaxel, paclitaxel, vinorelbine, fulvestrant, tamoxifen, anastrozole, exemestane, letrozole, trastuzumb, and/or metabolites thereof, and/or a pharmaceutically acceptable salt thereof.

A twenty fifth embodiment includes the method and/or the composition of any one of the preceding embodiments, wherein cancer includes bone cancer, brain cancer, breast cancer, endocrine cancer, gastrointestinal cancer, gynegologic cancer, head and neck cancer, hematologic cancer, lung cancer, prostate cancer, renal cell carcinoma, skin cancer, urologic cancer, and/or rare cancers. Consistent with this embodiment, wherein cancer includes breast cancer.

A twenty sixth embodiment includes the method and/or the composition of any one of the preceding embodiments, wherein at least one therapeutically effective anti-cancer agent and at least one compound that reduces the activity of at least one DNA damage/repair pathway exhibits synergy. In these embodiments, the at least one compound that reduces the activity of at least one DNA damage/repair pathway includes, but is not limited to, a fatty acid synthase (FASN) inhibitor, a proton pump inhibitor (PPI), a poly ADP ribose polymerase (PARP) inhibitor, a specific protein 1 (SP1) inhibitor, FASN siRNA, PARP siRNA, SP1 siRNA, and/or any combination thereof. Consistent with these embodiments, the synergistic composition comprises at least one proton pump inhibitor (PPI) and at least one PARP inhibitor, and the ratio between the at least one proton pump inhibitor (PPI) and at least one PARP inhibitor is from about 100:1 to about 1:100, from about 80:1 to about 1:80, from about 70:1 to about 1:70, from about 50:1 to about 1:50, from about 30:1 to about 1:30, from about 20:1 to about 1:20, from about 15:1 to about 1:15, from about 10:1 to about 1:10, from about 5:1 to about 1:5, from about 3:1 to about 1:3, from about 3:1 to about 1:1, and/or from about 1:1 to about 1:3. Some embodiments include the synergistic composition comprising the at least one proton pump inhibitor (PPI) and at least one PARP inhibitor and the ratio between the at least one proton pump inhibitor (PPI) and at least one PARP inhibitor is about 1:10, 1:9, 1:8, 1:7, 1:6, 1:5, 1:4, 1:3, 1:2, 1:1, 10:1, 9:1, 8:1, 7:1, 6:1, 5:1, 4:1, 3:1, and/or 2:1. Some synergistic compositions comprise a poly ADP ribose polymerase (PARP) inhibitor including, but is not limited to, olaparib, niraparib, iniparib, talazoparib, veliparib, and rucaparib; and a proton pump inhibitor including, but is not limited to, omeprazole, PRILOSEC®, lansoprazole, PREVACID®, dexlansoprazole, DEXILENT®, rabeprazole, ACIPHEX®, pantoprazole, PROTONIX®, esomeprazole, NEXIUM®, and ZEGARID®, anaprazole, tenatoprazole, ilaprozole, and/or metabolites thereof, and/or R- or S-enantiomers thereof, and/or a pharmaceutically acceptable salt thereof; or any combinations thereof.

Consistent with these embodiments, the synergistic composition comprises lansoprazole and olaparib, and the ratio between lansoprazole and olaparib is from about 100:1 to about 1:100, from about 80:1 to about 1:80, from about 70:1 to about 1:70, from about 50:1 to about 1:50, from about 30:1 to about 1:30, from about 20:1 to about 1:20, from about 15:1 to about 1:15, from about 10:1 to about 1:10, from about 5:1 to about 1:5, from about 3:1 to about 1:3, from about 3:1 to about 1:1, and/or from about 1:1 to about 1:3. Some embodiments include the synergistic composition comprising lansoprazole and olaparib, wherein the ratio between lansoprazole and olaparib is about 1:10, 1:9, 1:8, 1:7, 1:6, 1:5, 1:4, 1:3, 1:2, 1:1, 10:1, 9:1, 8:1, 7:1, 6:1, 5:1, 4:1, 3:1, and/or 2:1.

In other embodiments, the synergistic composition comprises lansoprazole and doxorubicin (or IR), and the ratio between lansoprazole and doxorubicin (or IR) is from about 100:1 to about 1:100, from about 80:1 to about 1:80, from about 70:1 to about 1:70, from about 50:1 to about 1:50, from about 30:1 to about 1:30, from about 20:1 to about 1:20, from about 15:1 to about 1:15, from about 10:1 to about 1:10, from about 5:1 to about 1:5, from about 3:1 to about 1:3, from about 3:1 to about 1:1, and/or from about 1:1 to about 1:3. Some embodiments include the synergistic composition comprising lansoprazole and doxorubicin (or IR), wherein the ratio between lansoprazole and doxorubicin (or IR) is about 1:10, 1:9, 1:8, 1:7, 1:6, 1:5, 1:4, 1:3, 1:2, 1:1, 10:1, 9:1, 8:1, 7:1, 6:1, 5:1, 4:1, 3:1, and/or 2:1.

A twenty seventh embodiment includes the method and/or the composition of any one of the preceding embodiments, wherein the at least one proton pump inhibitor is an R-enantiomer. Some embodiments include the method and/or the composition of any one of the preceding embodiments, wherein the at least one proton pump inhibitor is 5-hydroxy lansoprazole sulfide.

A twenty eighth embodiment includes the method and/or the composition of any one of the preceding embodiments, wherein the patient is diagnosed with type-1 and/or type-2 diabetes.

A twenty ninth embodiment includes the method and/or the composition according to any one of the preceding embodiments, wherein the therapeutically effective dose of the at least one proton pump inhibitor is on the order of between about 0.01 mg to about 200 mg and the dose of the compound is administered to the patient at least once per day. In some embodiments, the therapeutically effective dose of the at least one proton pump inhibitor includes, but is not limited to, on the order of between: about 0.01 mg to about 150 mg; about 0.01 mg to about 100 mg; about 0.01 mg to about 80 mg; about 0.01 mg to about 60 mg; about 0.05 mg to about 100 mg; about 0.05 mg to about 80 mg; about 0.05 mg to about 50 mg; about 0.1 mg to about 100 mg; about 0.1 mg to about 50 mg; about 0.2 mg to about 100 mg; about 0.2 mg to about 50 mg; about 0.5 mg to about 100 mg; about 0.5 mg to about 50 mg; about 100 mg to about 200 mg; about 100 mg to about 150 mg; and/or any combination thereof. Consistent with these embodiments, the therapeutically effective dose of the at least one proton pump inhibitor includes, but not limited to, on the order of between: about 0.01 $mg/m^2$ to about 100 $mg/m^2$; about 0.01 $mg/m^2$ to about 80 $mg/m^2$; about 0.01 $mg/m^2$ to about 50 $mg/m^2$; about 0.01 $mg/m^2$ to about 25 $mg/m^2$; about 0.05 $mg/m^2$ to about 100 $mg/m^2$; about 0.05 $mg/m^2$ to about 80 $mg/m^2$; about 0.05 $mg/m^2$ to about 50 $mg/m^2$; about 80 $mg/m^2$ to about 150 $mg/m^2$; about 80 $mg/m^2$ to about 120 $mg/m^2$; and/or any combination thereof.

A thirtieth embodiment includes the method and/or the composition according to any one of the preceding embodiments, wherein the therapeutically effective dose of the at least one anti-cancer agent is on the order of between about 0.01 mg to about 200 mg and the dose of the compound is administered to the patient at least once per day. In some embodiments, the therapeutically effective dose of the at least one anti-cancer agent includes, but is not limited to, on the order of between: about 0.01 mg to about 150 mg; about 0.01 mg to about 100 mg; about 0.01 mg to about 80 mg; about 0.01 mg to about 60 mg; about 0.05 mg to about 100 mg; about 0.05 mg to about 80 mg; about 0.05 mg to about 50 mg; about 0.1 mg to about 100 mg; about 0.1 mg to about 50 mg; about 0.2 mg to about 100 mg; about 0.2 mg to about 50 mg; about 0.5 mg to about 100 mg; about 0.5 mg to about 50 mg; about 100 mg to about 200 mg; about 100 mg to about 150 mg; and/or any combination thereof. Consistent with these embodiments, the therapeutically effective dose of the at least one anti-cancer agent includes, but not limited to, on the order of between: about 0.01 $mg/m^2$ to about 100 $mg/m^2$; about 0.01 $mg/m^2$ to about 80 $mg/m^2$; about 0.01 $mg/m^2$ to about 50 $mg/m^2$; about 0.01 $mg/m^2$ to about 25 $mg/m^2$; about 0.05 $mg/m^2$ to about 100 $mg/m^2$; about 0.05 $mg/m^2$ to about 80 $mg/m^2$; about 0.05 $mg/m^2$ to about 50 $mg/m^2$; about 80 $mg/m^2$ to about 150 $mg/m^2$; about 80 $mg/m^2$ to about 120 $mg/m^2$; and/or any combination thereof.

A thirty first embodiment includes the method and/or the composition according to any one of the preceding embodiments, wherein the therapeutically effective dose of the poly ADP ribose polymerase (PARP) inhibitor is on the order of between about 0.01 mg to about 200 mg and the dose of the compound is administered to the patient at least once per day. In some embodiments, the therapeutically effective dose of the poly ADP ribose polymerase (PARP) inhibitor includes, but is not limited to, on the order of between: about 0.01 mg to about 150 mg; about 0.01 mg to about 100 mg; about 0.01 mg to about 80 mg; about 0.01 mg to about 60 mg; about 0.05 mg to about 100 mg; about 0.05 mg to about 80 mg; about 0.05 mg to about 50 mg; about 0.1 mg to about 100 mg; about 0.1 mg to about 50 mg; about 0.2 mg to about 100 mg; about 0.2 mg to about 50 mg; about 0.5 mg to about 100 mg; about 0.5 mg to about 50 mg; about 100 mg to about 200 mg; about 100 mg to about 150 mg; and/or any combination thereof. Consistent with these embodiments, the therapeutically effective dose of the poly ADP ribose polymerase (PARP) inhibitor includes, but not limited to, on the order of between: about 0.01 $mg/m^2$ to about 100 $mg/m^2$; about 0.01 $mg/m^2$ to about 80 $mg/m^2$; about 0.01 $mg/m^2$ to about 50 $mg/m^2$; about 0.01 $mg/m^2$ to about 25 $mg/m^2$; about 0.05 $mg/m^2$ to about 100 $mg/m^2$; about 0.05 $mg/m^2$ to about 80 $mg/m^2$; about 0.05 $mg/m^2$ to about 50 $mg/m^2$; about 80 $mg/m^2$ to about 150 $mg/m^2$; about 80 $mg/m^2$ to about 120 $mg/m^2$; and/or any combination thereof.

A thirty second embodiment includes the method and/or the composition according to any one of the preceding embodiments, wherein the therapeutically effective dose of the at least one agent that reduces the activity of the at least one DNA damage/repair pathway is on the order of between about 0.01 mg to about 200 mg and the dose of the compound is administered to the patient at least once per day. In some embodiments, the therapeutically effective dose of the at least one agent that reduces the activity of the at least one DNA damage/repair pathway includes, but is not limited to, on the order of between: about 0.01 mg to about 150 mg; about 0.01 mg to about 100 mg; about 0.01 mg to about 80 mg; about 0.01 mg to about 60 mg; about 0.05 mg to about 100 mg; about 0.05 mg to about 80 mg; about 0.05 mg to about 50 mg; about 0.1 mg to about 100 mg; about 0.1 mg to about 50 mg; about 0.2 mg to about 100 mg; about 0.2 mg to about 50 mg; about 0.5 mg to about 100 mg; about 0.5 mg to about 50 mg; about 100 mg to about 200 mg; about 100 mg to about 150 mg; and/or any combination thereof. Consistent with these embodiments, the therapeutically effective dose of the at least one agent that reduces the activity of the at least one DNA damage/repair pathway includes, but not limited to, on the order of between: about 0.01 $mg/m^2$ to about 100 $mg/m^2$; about 0.01 $mg/m^2$ to about 80 $mg/m^2$; about 0.01 $mg/m^2$ to about 50 $mg/m^2$; about 0.01 $mg/m^2$ to about 25 $mg/m^2$; about 0.05 $mg/m^2$ to about 100 $mg/m^2$; about 0.05 $mg/m^2$ to about 80 $mg/m^2$; about 0.05 $mg/m^2$ to about 50 $mg/m^2$; about 80 $mg/m^2$ to about 150 $mg/m^2$; about 80 $mg/m^2$ to about 120 $mg/m^2$; and/or any combination thereof.

A thirty third embodiment includes the method and/or the composition of any one of the preceding embodiments, wherein the patient is treated by suppressing DNA damage repair via inhibiting FASN activity and PARP1 expression.

A thirty fourth embodiment includes the method and/or the composition of any one of the preceding embodiments, the patient includes, but is not limited to, African American and/or Caucasian patients.

BRIEF DESCRIPTION OF SEQUENCES

SEQ ID NO: 1
CCCAGGGTCTTCGGATAG.

SEQ ID NO: 2
AGCGTGCTTCAGTTCATACA.

SEQ ID NO: 3
CCGGGTCCTCCAAAGAGCTA.

SEQ ID NO: 4
GCCGTTCCCTGATAGATTGCT.

SEQ ID NO: 5
CGCCCGGGAAACTCCGCCCCCCGGCCGGCAGGGGGCGCGCGCCGCCGGC

CCCGCCCCGTGGACGCGGGTTCCGTGGGCGTTCCCGCGGCCAGGCATCA.

$$\frac{(D)_1}{(D_x)_1} + \frac{(D)_2}{(D_x)_2} = CI$$

as described by Chou and Talalay (Adv. Enzyme Regulation 22: 27-55; 1984) with CI<1 for synergism, CI=1 for additivity, and CI>1 for antagonism.

Figure 16:
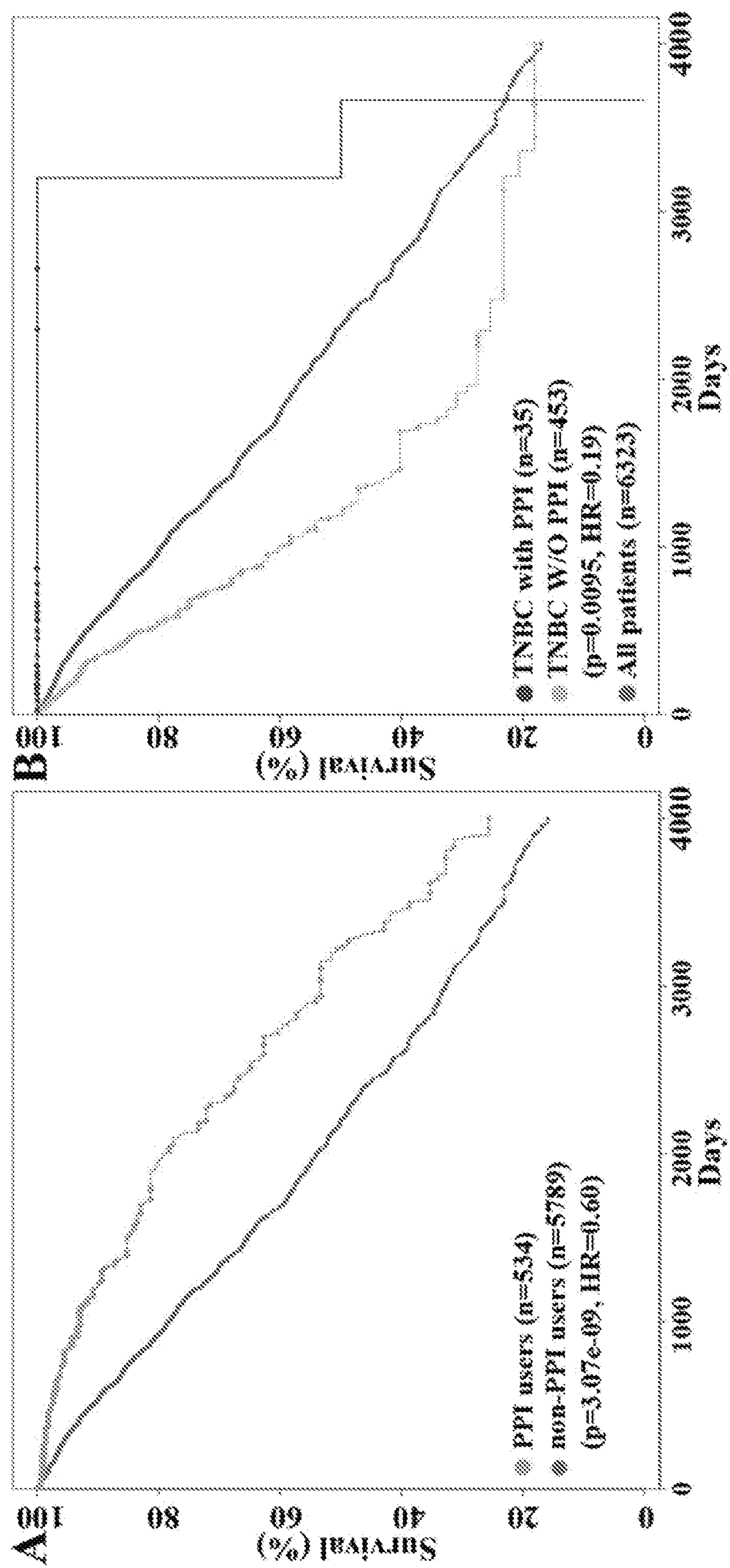

FIG. 16. Retrospective survival analysis of breast cancer patients with or without use of proton pump inhibitors (PPIs). De-identified electronic medical records of 6,752 breast cancer patients were retrieved from the database of Indiana Network for Patient Care (INPC) and subjected to Kaplan-Meier survival analysis in association with PPI usage in all patients (A) or in triple negative breast cancer patient subgroup (B). The p-value and hazard ratio (HR) were calculated from Cox proportional hazard models, which were adjusted for age, tumor stage, and time of first diagnosis.

Figure 17:
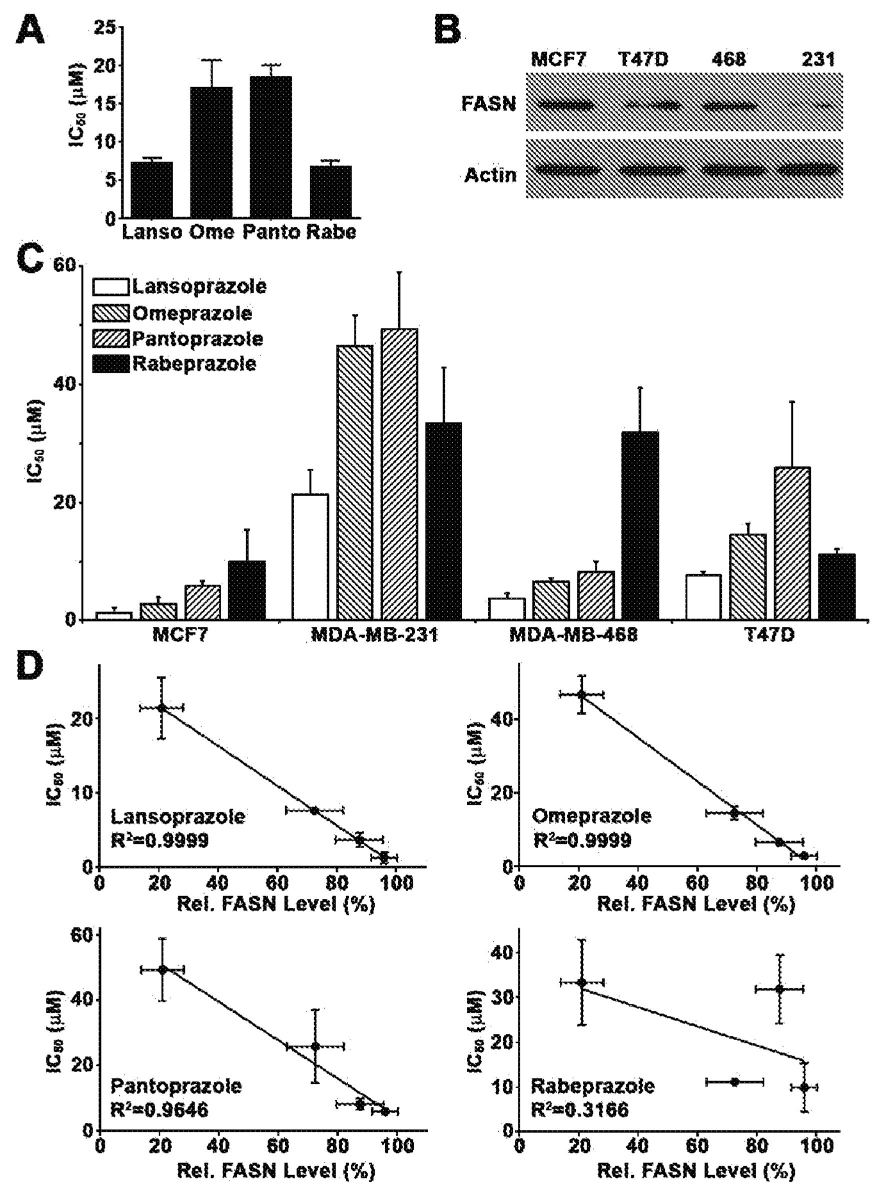

FIG. 17. PPI inhibition of FASN activity and breast cancer cell survival. A, $IC_{50}$ of PPIs in inhibiting FASN activity derived from dose-response curves (see FIG. 25). Lanso, lansoprazole; Ome, omeprazole; Panto, pantoprazole; Rabe, rabeprazole. B, Western blot analysis of FASN expression in different human breast cancer cell lines. 468, MDA-MB-468; 231, MDA-MB-231. C, $IC_{50}$ of PPIs in inhibiting breast cancer cell survival derived from dose response survival curves (see FIG. 26). D, Correlation analysis between PPI $IC_{50}$ in inhibiting survival of breast cancer cells and relative FASN expression level in the same cells.

Figure 18:
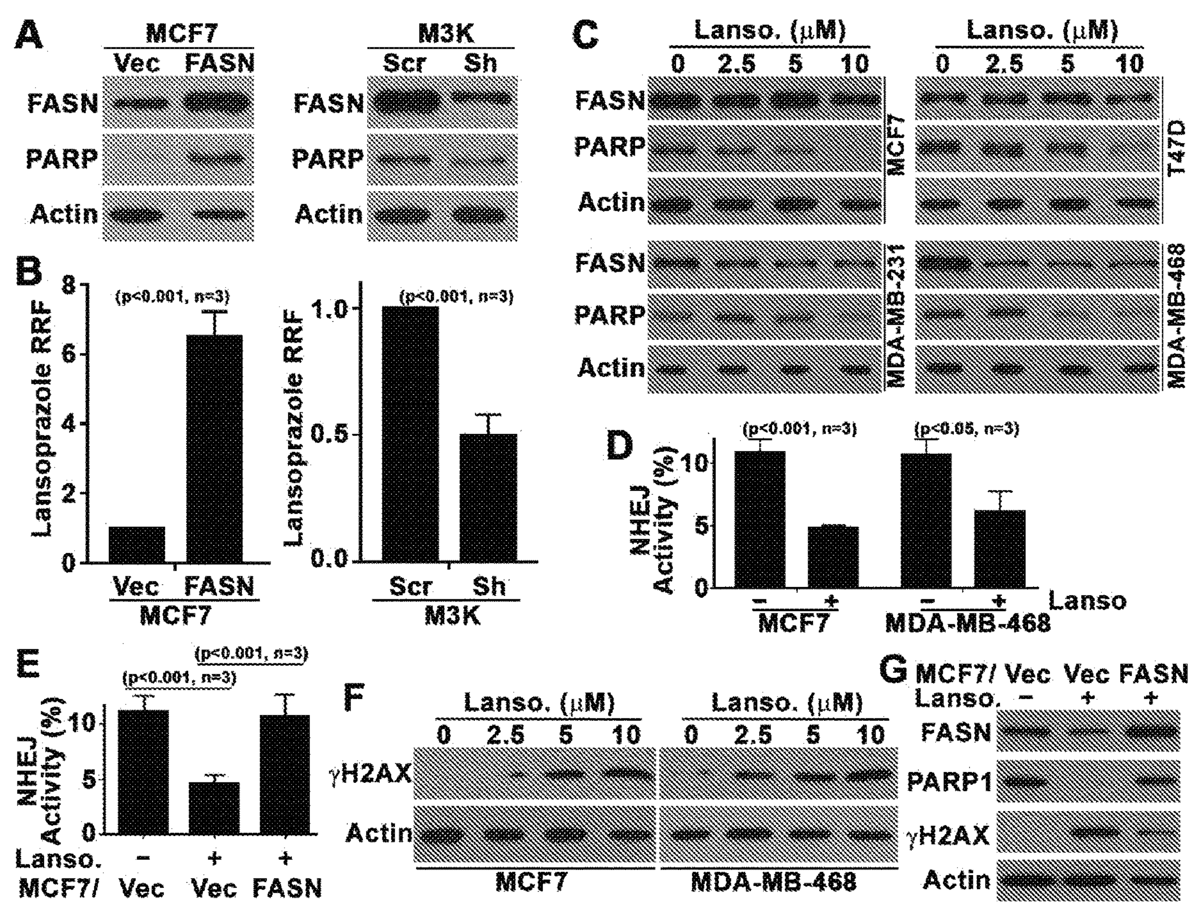

FIG. 18. Role of FASN in mediating PPI effect. A, Western blot analysis of FASN and PARP1 expression in MCF7 cells with ectopic FASN over-expression and in drug resistant MCF7/AdVp3000 (M3K) cells with FASN knockdown. B, Relative resistance factor (RRF) to lansoprazole in MCF7 cells with FASN over-expression or M3K cells with FASN knockdown. RRF=Lansoprazole $IC_{50\ (FASN\ or\ Sh)}/IC_{50\ (Vec\ or\ Scr)}$. C, Western blot analysis of endogenous FASN and PARP1 expression in MCF7, T47D, MDA-MB-231, and MDA-MB-468 cells following treatments with lansoprazole at different concentrations. D, Effect of lansoprazole on NHEJ activity in MCF7 and MDA-MB-468 cells. E, Rescue of lansoprazole-induced reduction in NHEJ activity by ectopic FASN over-expression. F, Western blot analysis of γH2AX level MCF7 and MDA-MB-468 cells treated with lansoprazole at different concentrations. G, Ablation of lansoprazole-induced γH2AX level increase by ectopic FASN over-expression as determined using Western blot analysis. Actin was used as loading control for all Western blot analyses.

Figure 19:
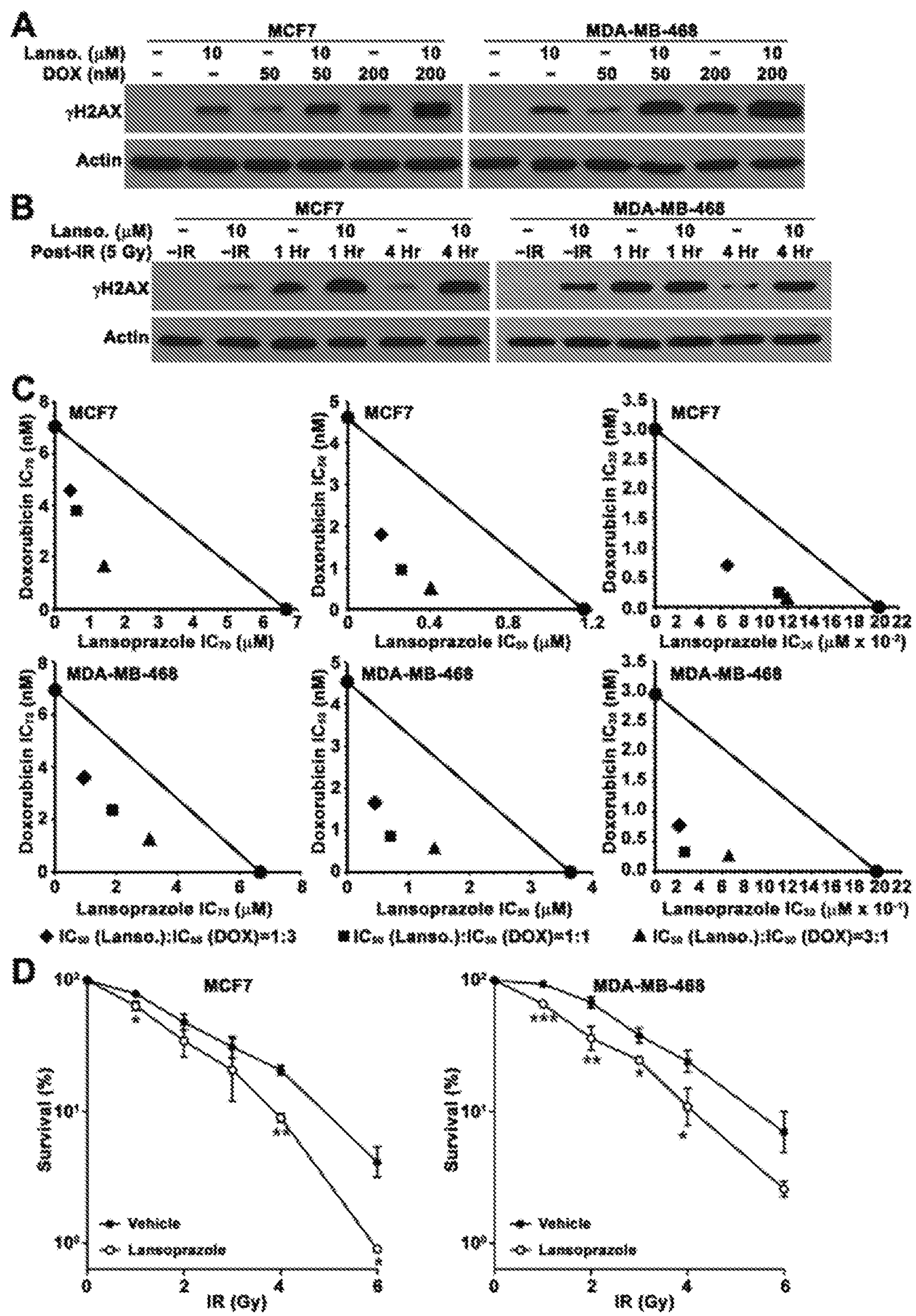

FIG. 19. Synergistic effect of lansoprazole with doxorubicin and ionizing radiation (IR). A and B, Western blot analysis γH2AX in MCF7 and MDA-MB-468 cells following treatment with lansoprazole, doxorubicin, IR, or lansoprazole with doxorubicin or IR. Actin was used as a loading control. C, Isoblologram of lansoprazole combination with doxorubicin with three different combination ratios. The solid circle connected by a solid line represents the $IC_{70}$, $IC_{50}$, or $IC_{30}$ of lansoprazole as doxorubicin single agents in survival assay. Other solid symbols represents $IC_{70}$, $IC_{50}$, or $IC_{30}$ of lansoprazole or doxorubicin in different combination treatments, which are below the line, indicating synergism. D, Lansoprazole sensitization of MCF7 and MDA-MB-468 cells to IR. (n=3, *p<0.05, **p<0.01).

Figure 20:
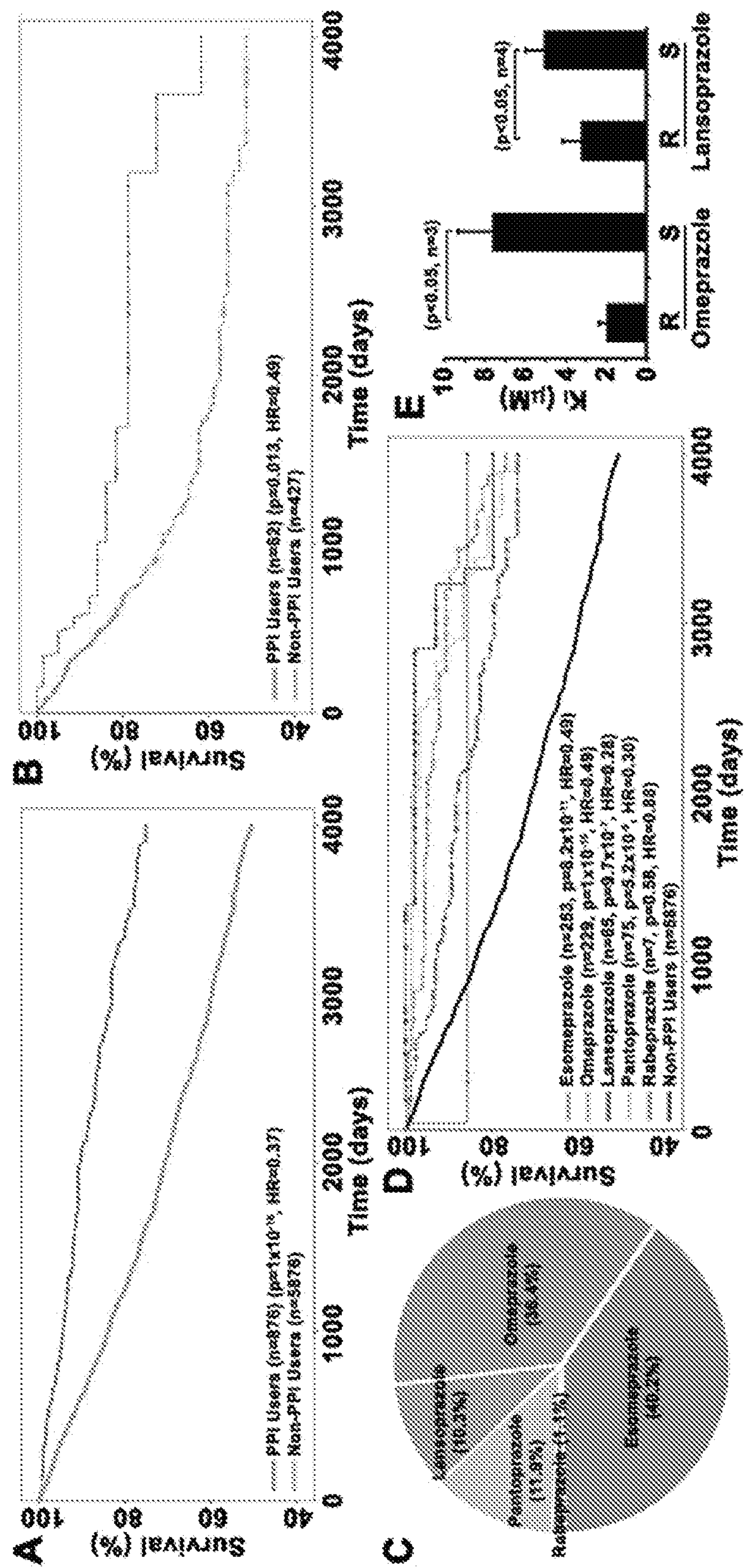

FIG. 20. Benefits of PPI usage and differential effects of R- and S-enantiomers. A, Kaplan-Meier analysis of overall survival among all breast cancer patients with or without PPI usage. Association of PPI usage with overall survival of breast cancer patients. B, Kaplan-Meier analysis of overall survival among TNBC patients with or without PPI usage. C, Distribution of single PPI users. D, Kaplan-Meier analysis of overall survival among all breast cancer patients using a single but different PPI. E, Inhibition of TE activity of FASN by different enantiomers of lansoprazole and omeprazole.

Figure 21:
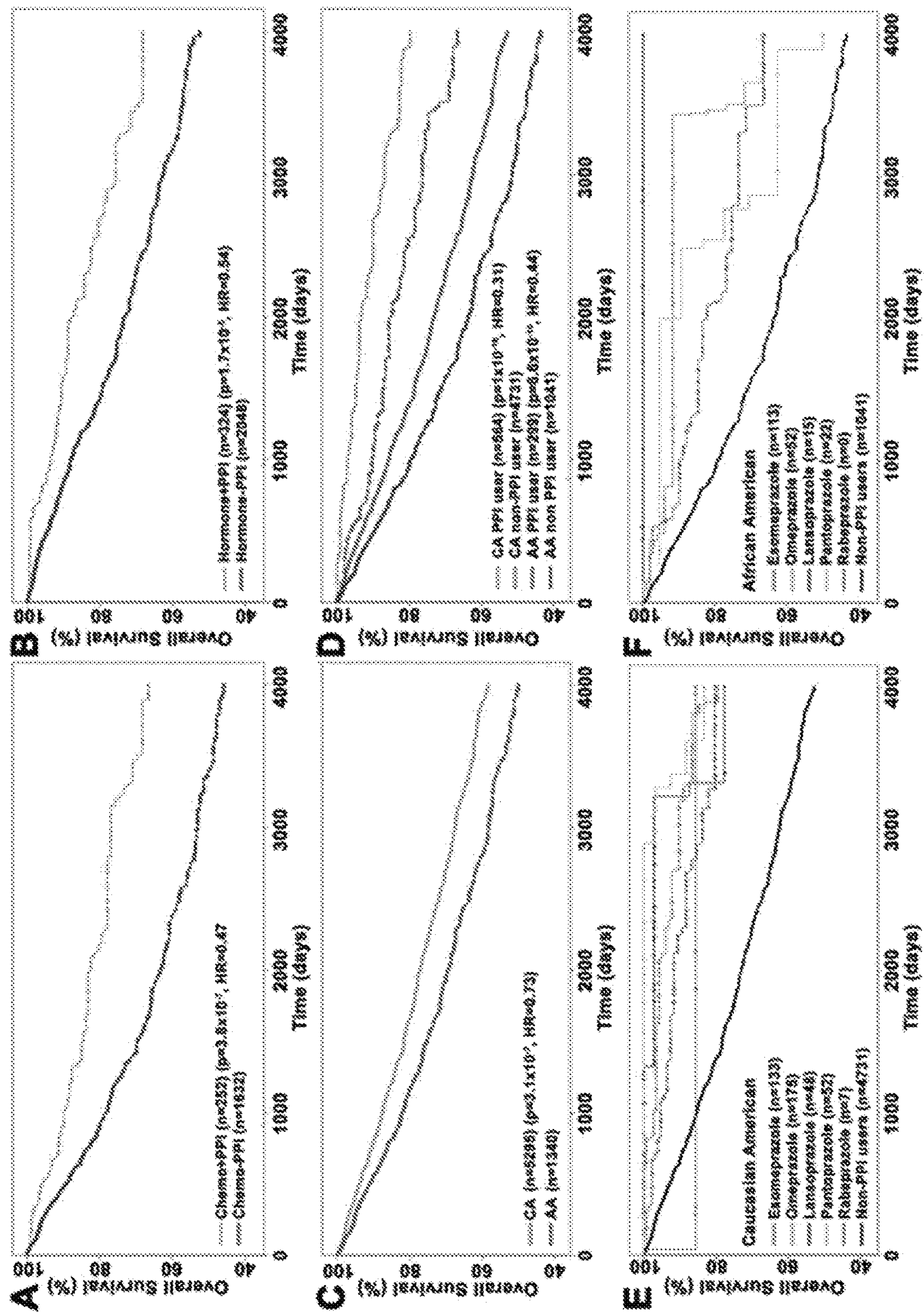

FIG. 21. Benefits of PPI usage in combination with chemotherapy or hormonal therapy and in different ethnic patients. A, Kaplan-Meier analysis of overall survival among all breast cancer patients receiving chemotherapy and with or without PPI usage. B, Kaplan-Meier analysis of overall survival among all breast cancer patients receiving hormonal therapy and with or without PPI usage. C, Kaplan-Meier analysis of overall survival Caucasian (CA) and African (AA) American breast cancer patients. D, Kaplan-Meier analysis of overall survival among CA and AA patients with or without PPI usage. E and F, Kaplan-Meier analysis of overall survival among CA and AA patients using different PPIs.

Figure 22:
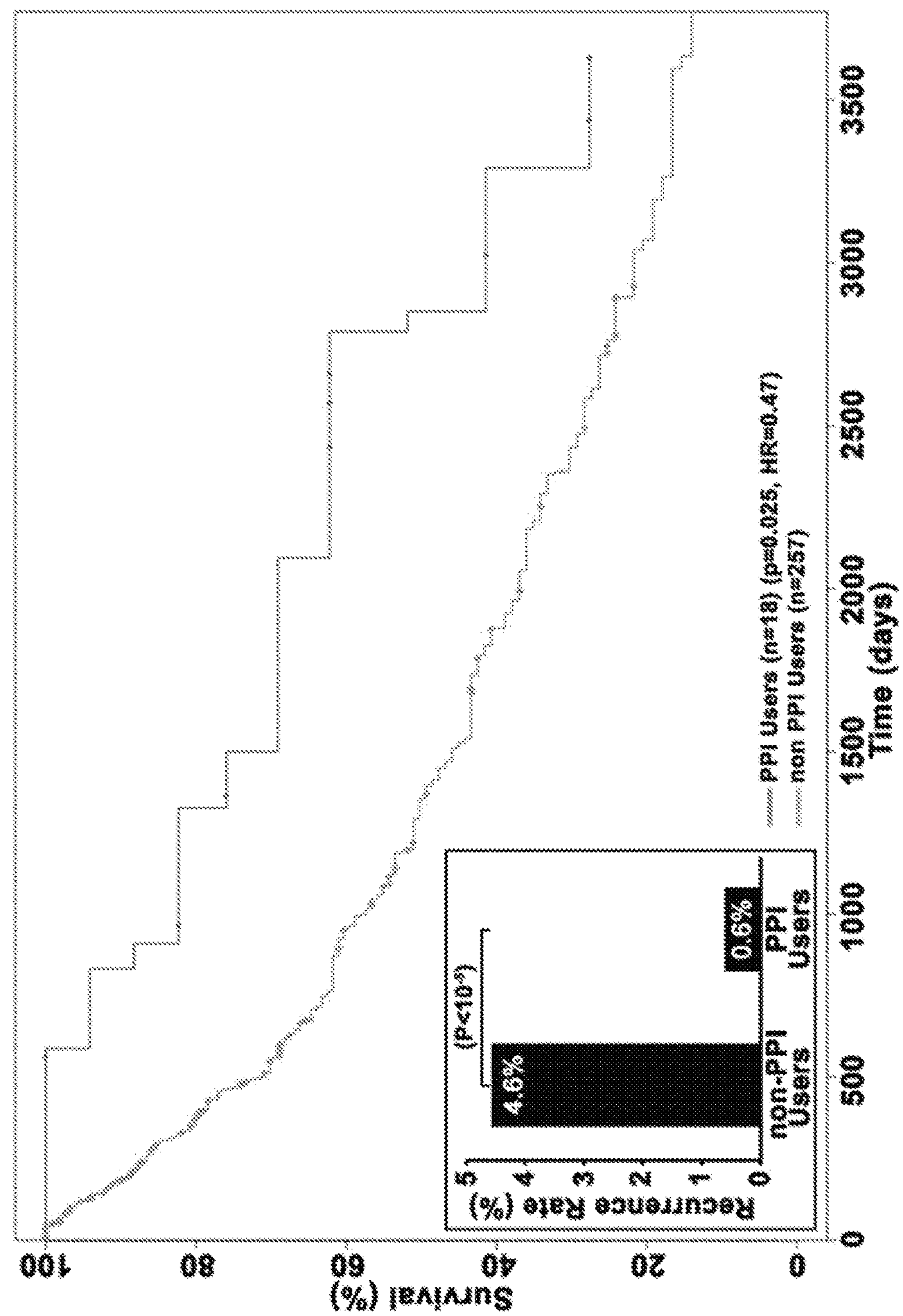

FIG. 22. Association between PPI usage and breast cancer recurrence. The curves show potential benefits of PPI usage on the overall survival of breast cancer patients with recurrent disease. The inset shows disease recurrence rates of PPI users and non-users.

Figure 23:
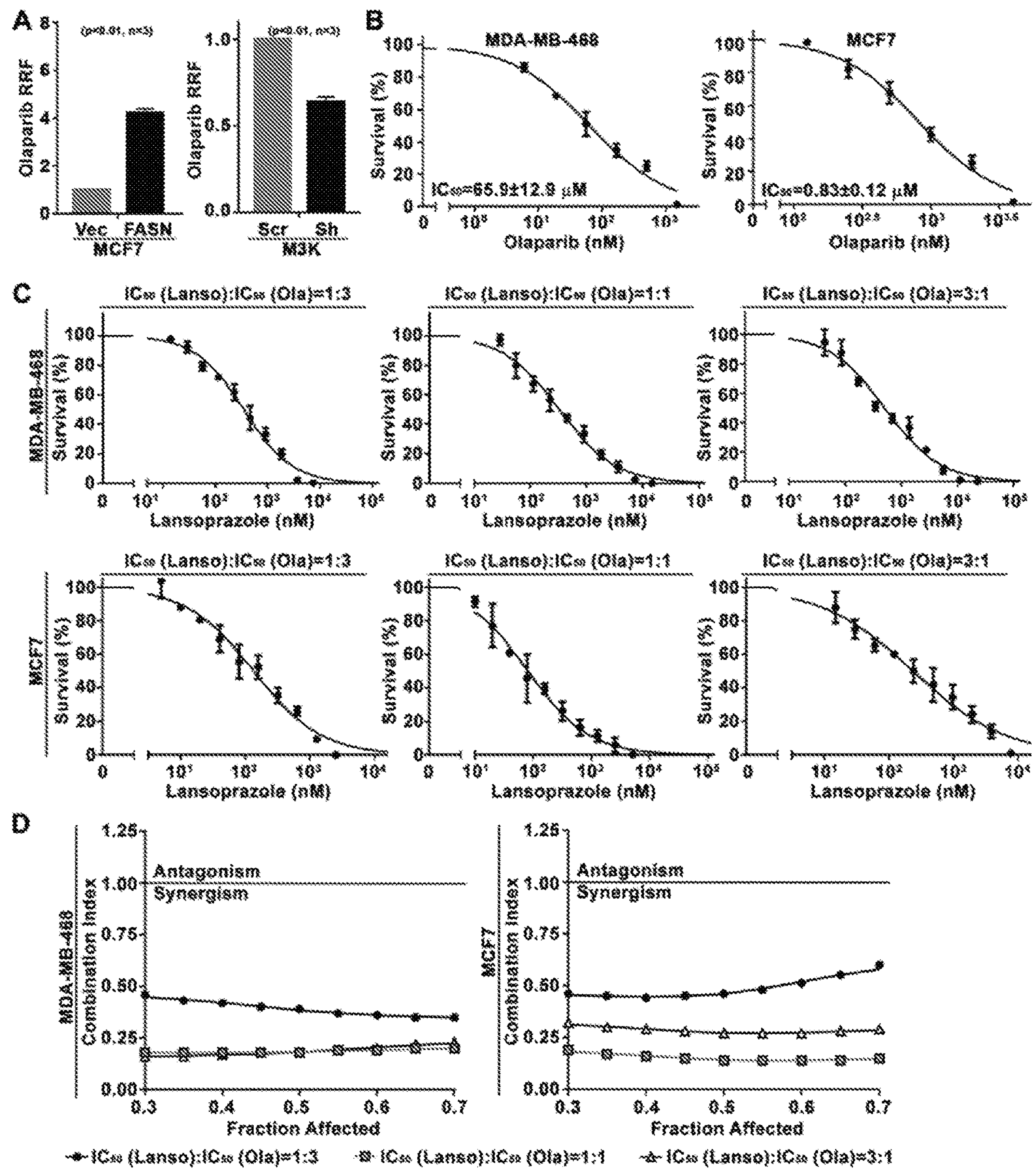

FIG. 23. Synergistic effect of lansoprazole with PARP inhibitor. A. Relative resistance factor (RRF) to olaparib in MCF7 cells with FASN over-expression or M3K cells with FASN knockdown. RRF=Lansoprazole $IC_{50\ (FASN\ or\ Sh)}/IC_{50\ (Vec\ or\ Scr)}$. B. Dose-dependent survival of MCF7 and MDA-MB-468 cells in the presence of olaparib as determined using colony formation assay. C. Dose-dependent survival of MCF7 and MDA-MB-468 cells in the presence of olaparib and lansoprazole in combination with different ratios. C. Combination index analysis between olaparib and lansoprazole in different combination ratios.

Figure 24:
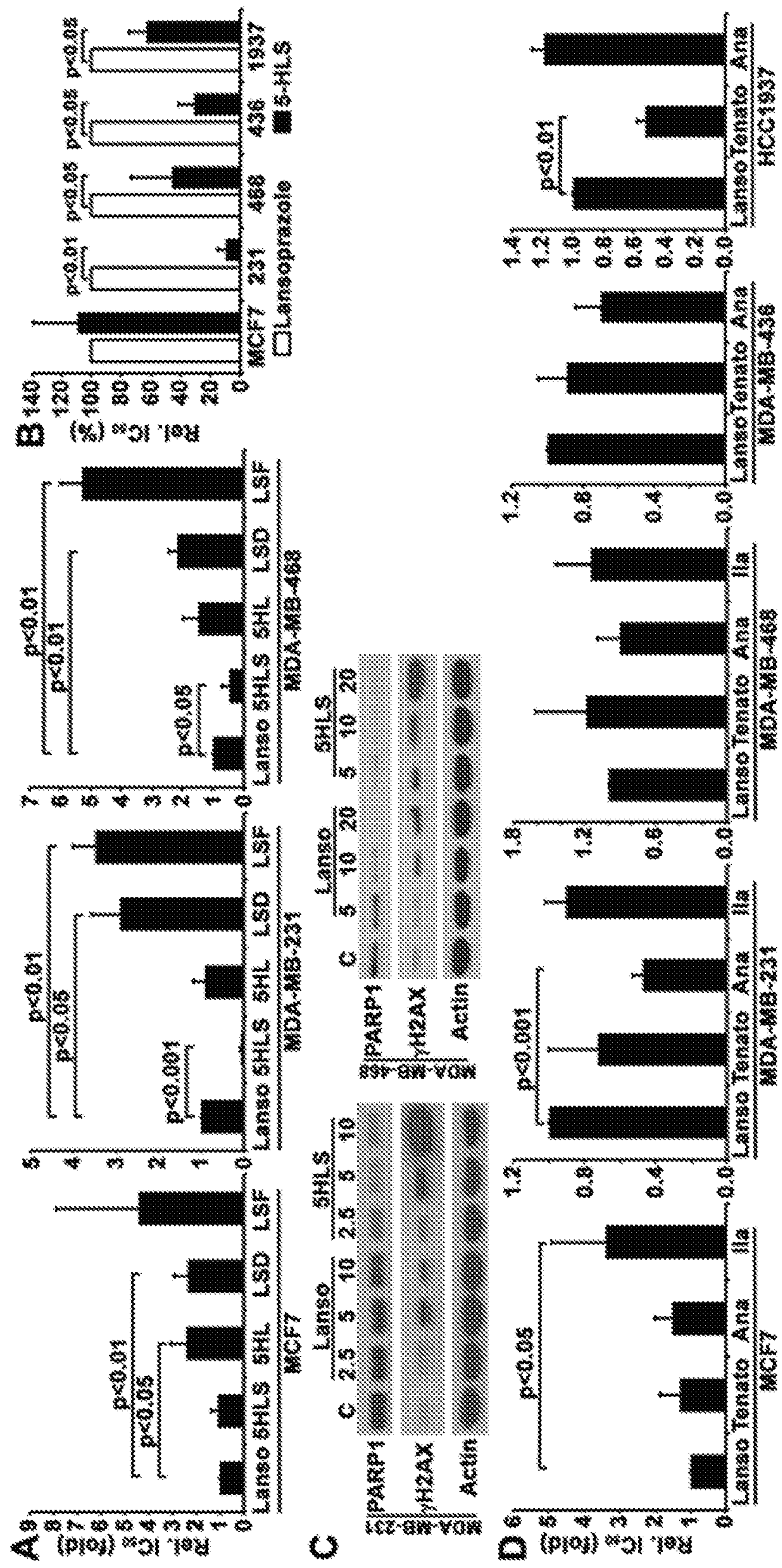

FIG. 24. Effect of lansoprazole metabolites and other non-approved PPIs on survival of breast cancer cells. A, effect of different metabolites of lansoprazole on the survival of MCF7, MDA-MB-231, MDA-MB-468 cells as determined using methylene blue staining assay. B, effect of 5-hydroxy lansoprazole sulfide on the survival of triple negative breast cancer cell lines. C, effect of 5-hydroxy lansoprazole on production of PARP1 and γ-H2AX as determined using Western blot analysis. Actin was used as a loading control. D. effect of non-approved PPIs on the survival of breast cancer cell lines. Relative $IC_{50}$=$IC_{50\ (metabolites\ or\ PPIs)}/IC_{50\ (lansoprazole)}$. Lanso, lansoprazole; 5HLS, 5-hydroxy lansoprazole sulfide; 5HL, 5-hydroxy lansoprazole; LSD, lansoprazole sulfide; LSF, lansoprazole sulfone; Ana, anaprazole; Tenato, tenatoprazole; Ila, ilaprazole.

Figure 25:
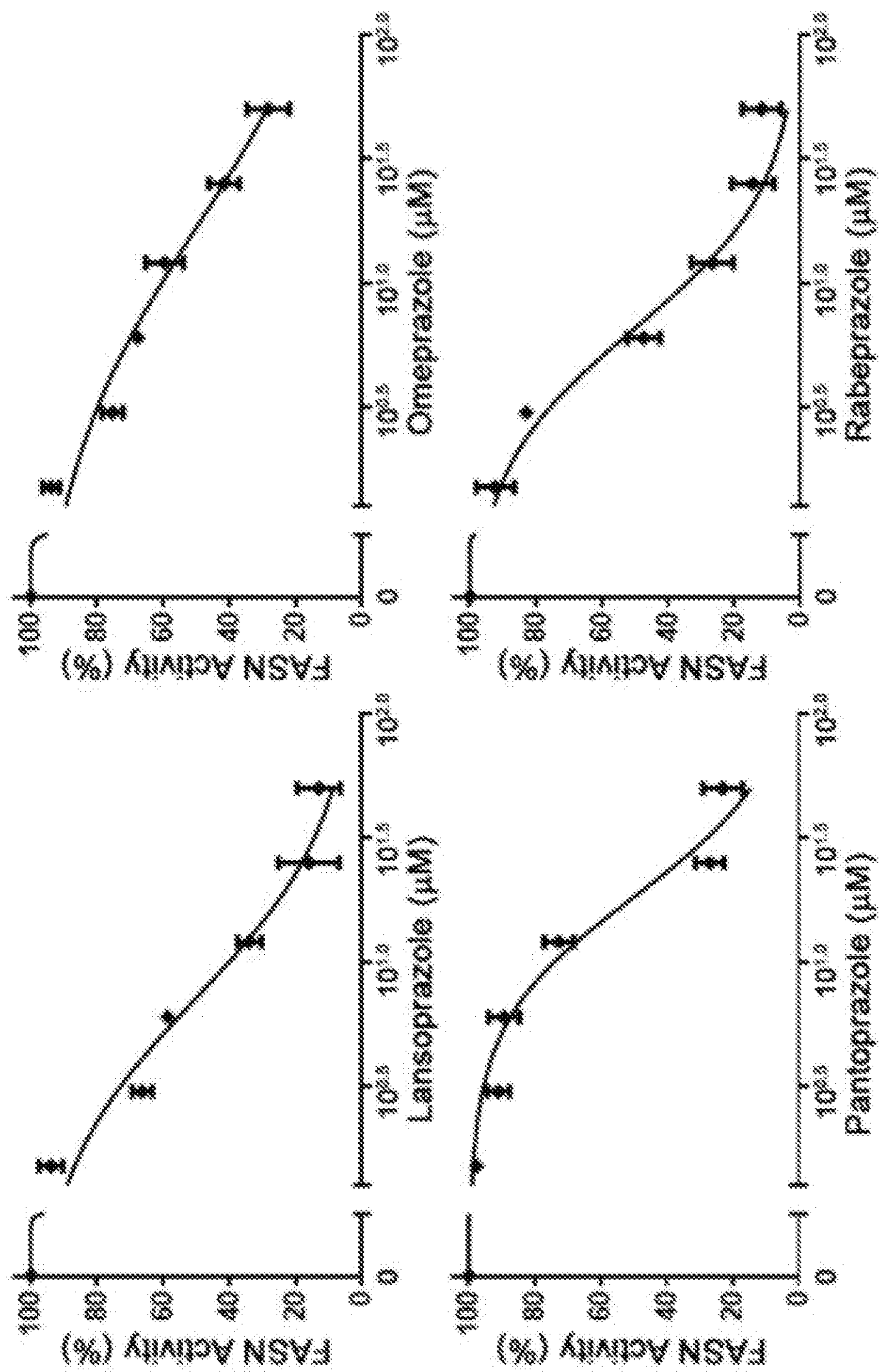

FIG. 25. Graphs illustrating dose-dependent inhibition of FASN activity by different PPIs.

Figure 26:
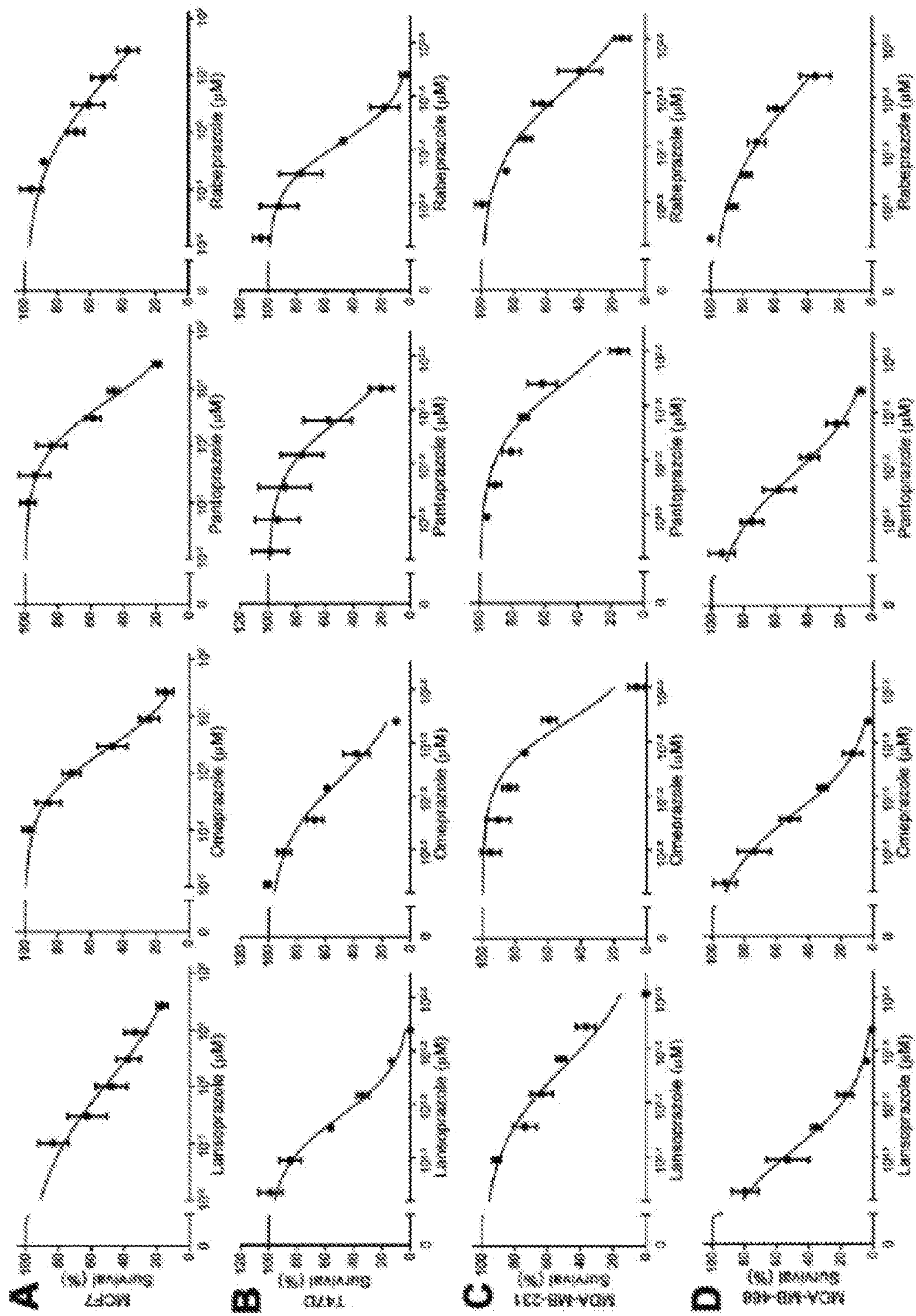

FIG. 26. Graphs illustrating colony formation survival assay of MCF7, T47D, MDA-MB-231, and MDA-MB-468 cells in the presence of various concentrations of different PPIs.

Figure 27:
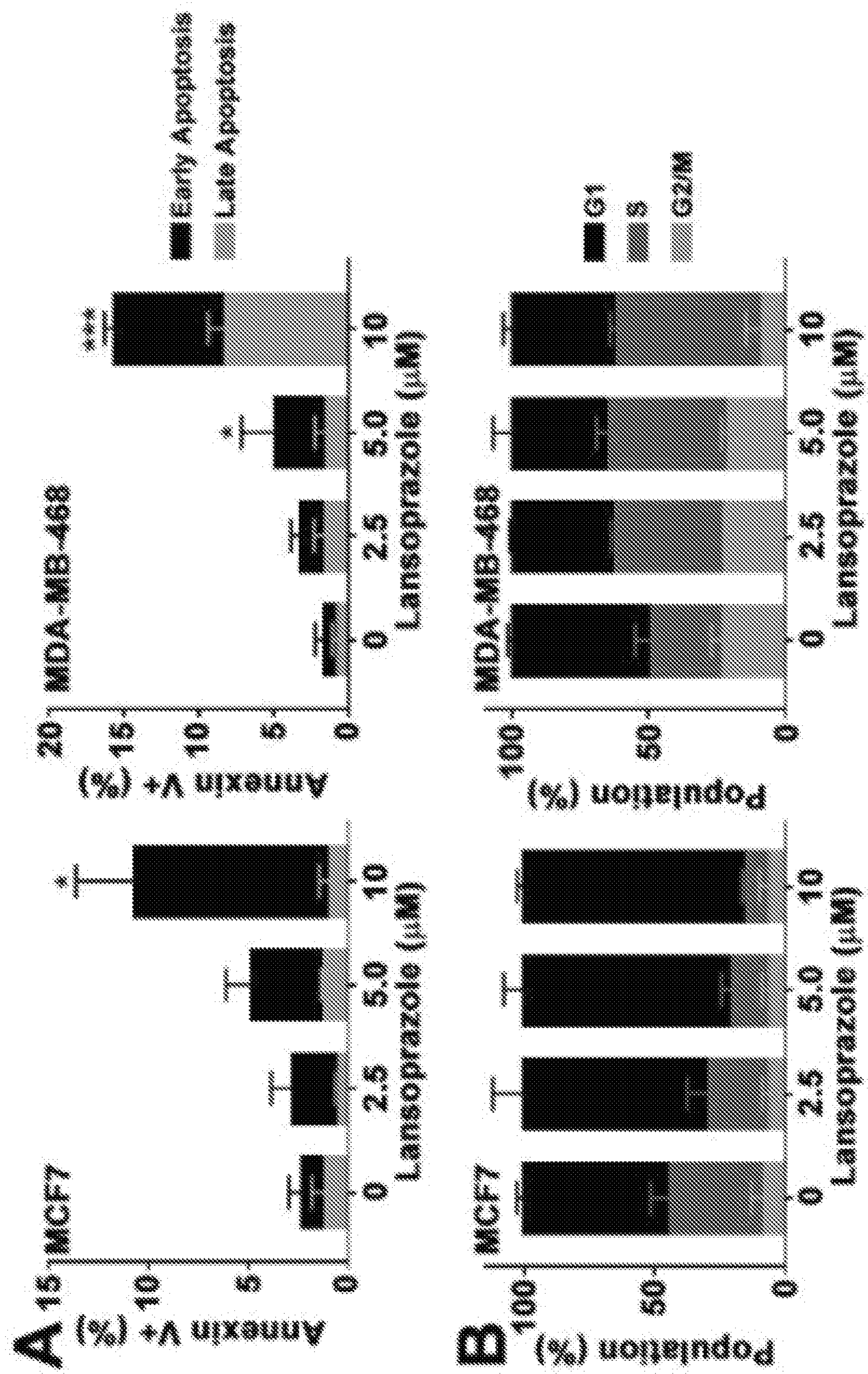

FIG. 27. Graphs illustrating the effect of lansoprazole on (A) apoptosis and (B) cell cycle distribution in MCF7 and MDA-MB-468 cells.

Figure 28:
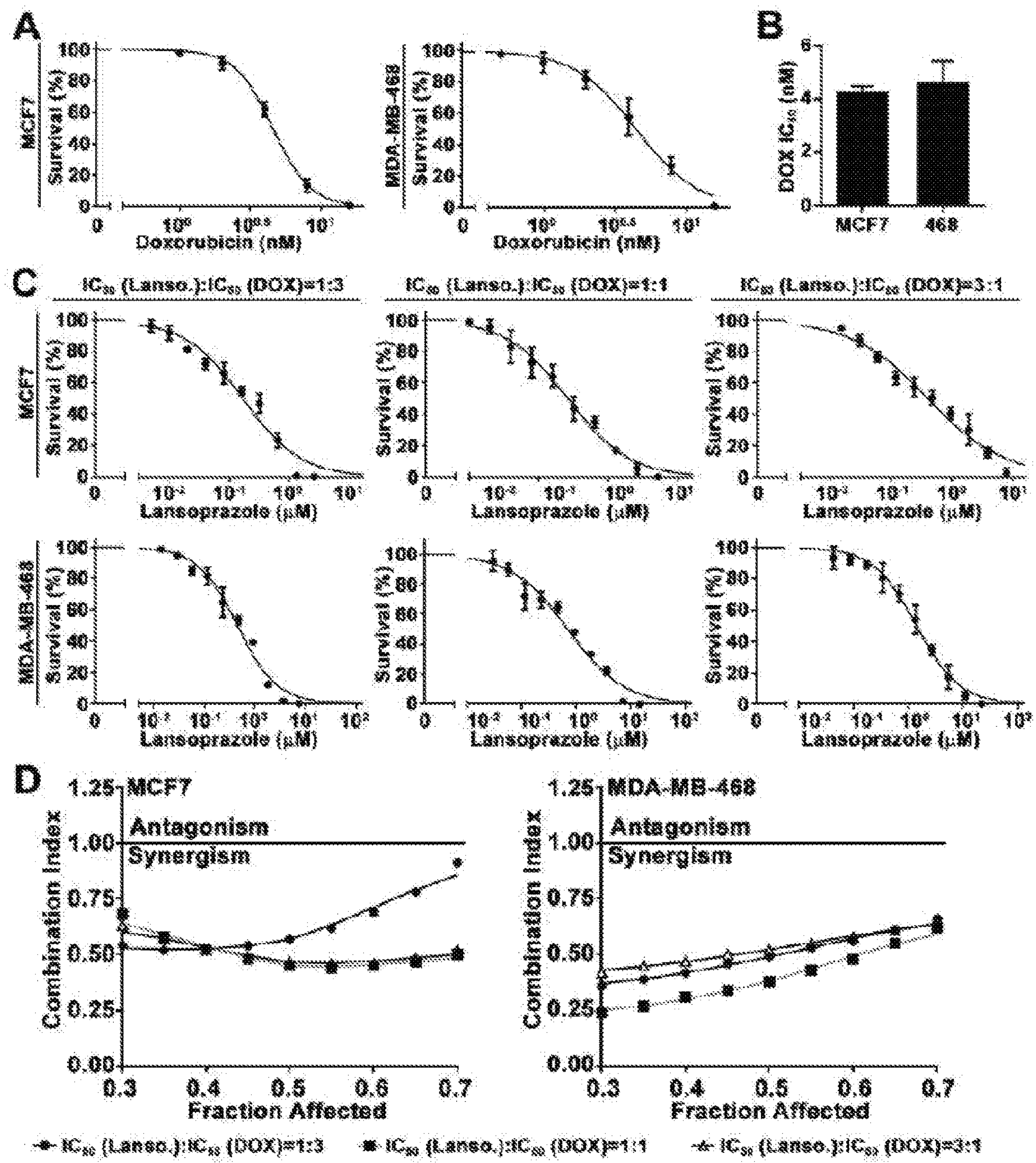

FIG. 28. A. Colony formation survival assay of MCF7 and MDA-MB-468 cells in the presence various concentrations of doxorubicin. B. Doxrubicin IC50 as determined from dose-dependent survival curves in panel A. C. Colony formation survival assay of MCF7 and MDA-MB-468 cells in the presence of different combinations of lansoprazole and doxorubicin. D. Combination index analysis between lansoprazole and doxorubicin with different combination ratios.

Figure 29:
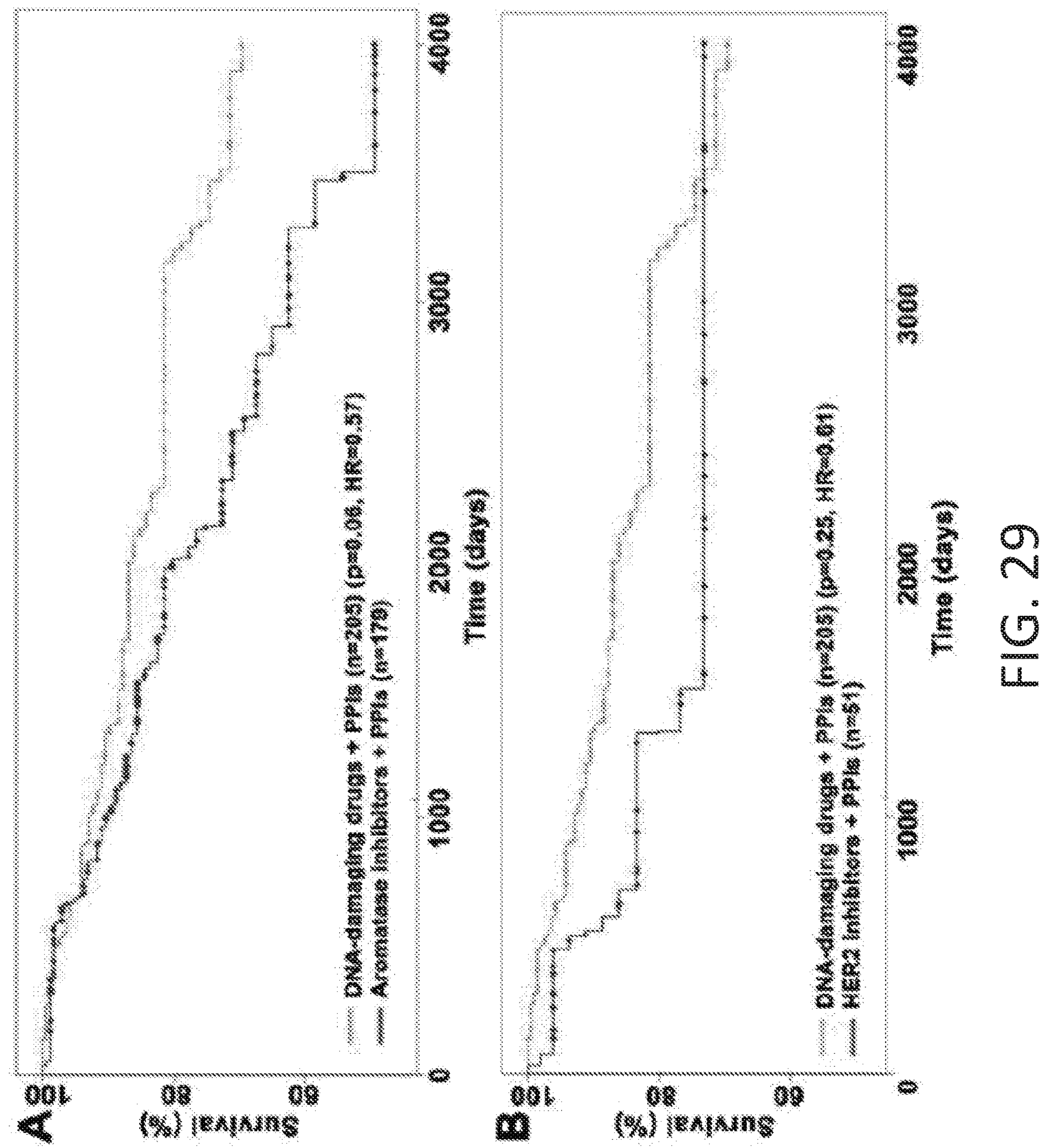

FIG. 29. A. Kaplan-Meier analysis of overall survival among breast cancer patients who took PPIs but were treated with DNA-damaging drugs or aromatase inhibitors. B. Kaplan-Meier analysis of overall survival among breast cancer patients who took PPIs but were treated with DNA-damaging drugs or HER2 inhibitors.

DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

As used herein, unless explicitly stated otherwise or clearly implied otherwise the terms 'therapeutically effective dose,' 'therapeutically effective amounts,' and the like, refer to a portion of a compound that has a net positive effect on health and well being of a human or other animal. Therapeutic effects may include an improvement in longevity, quality of life and the like these effects also may also include a reduced susceptibility to developing disease or deteriorating health or well being. The effects may be immediate realized after a single dose and/or treatment or they may be cumulative realized after a series of doses and/or treatments. A "therapeutically effective amount" in general means the amount that, when administered to a subject or animal for treating a disease, is sufficient to affect the desired degree of treatment for the disease.

The term, "treating" as used herein unless stated or implied otherwise, includes administering to a human or an animal patient at least one dose of a compound, treating includes preventing or lessening the likelihood and/or severity of at least one disease as well as limiting the length of an illness or the severity of an illness, treating may or may not result in a cure of the disease.

As used herein, "inhibition" or "inhibitory activity" each encompass whole or partial reduction of activity or effect of an enzyme or all and/or part of a pathway that includes an enzyme that is effected either directly or indirectly by the inhibitor or a pathway that is effected either directly or indirectly by the activity of the enzyme which is effected either directly or indirectly by the inhibitor.

A "selective" PARP-1 inhibitor is one that has at least 2, 5, 10, 20, 50, 100, or 200 fold greater inhibitory activity (for example, as determined by calculation of $IC_{50}$, $K_i$, or other measure of affinity or effect) for a particular isozyme of PARP-1 compared to other members of the PARP family.

As used herein, "proton pump inhibitors (PPIs)" include, but are not limited to, omeprazole, PRILOSEC®, lansoprazole, PREVACID®, dexlansoprazole, DEXILENT®, rabeprazole, ACIPHEX®, pantoprazole, PROTONIX®, esomeprazole, NEXIUM®, and ZEGARID®, anaprazole, tenatoprazole, ilaprozole, and/or metabolites thereof, and/or R- or S-enantiomers thereof, and/or a pharmaceutically acceptable salt thereof.

As used herein, "poly ADP ribose polymerase (PARP) inhibitors" include, but are not limited to, olaparib, niraparib, iniparib, talazoparib, veliparib, rucaparib, CEP 9722, E7016, and BGB-290.

As used herein, "therapeutic regime" and/or "therapeutic regimens" include, but are not limited to, surgery, chemotherapy, radiation therapy, siRNAs or shRNAs, targeted therapy, precision medicine, immunotherapy, stem cell transplant, hyperthermia, photodynamic therapy, blood product donation and transfusion, Light Amplification by Stimulated Emission of Radiation (LASER) in cancer treatment, DNA-damaging radiotherapy, endocrine therapy, and hormone therapy.

As used herein, "therapeutic agents" include, but are not limited to, fatty acid synthase (FASN) inhibitors and/or siRNAs, poly ADP ribose polymerase (PARP) inhibitors and/or siRNAs, specific protein 1 (SP1) inhibitors and/or siRNAs, proton pump inhibitors (PPIs), anti-cancer drugs, DNA-damaging drugs (e.g., doxorubicin, bleomycin, vinblastine, paclitaxel, mitoxantrone, and cisplatine), $H_2O_2$, UVB, ionizing radiation, monoclonal antibodies, and cancer vaccines.

As used herein, "cancer" includes, but is not limited to, bone cancer, brain cancer, breast cancer, endocrine cancer, gastrointestinal cancer, gynegologic cancer, head and neck cancer, hematologic cancer, lung cancer, prostate cancer, renal cell carcinoma, skin cancer, urologic cancer, and rare cancers.

As used herein, the term "pharmaceutically acceptable salt" is defined as a salt wherein the desired biological activity of the inhibitor is maintained and which exhibits a minimum of undesired toxicological effects. Non-limiting examples of such a salt are (a) acid addition salts formed with inorganic acids (e.g., hydrochloric acid, hydrobromic acid, sulphuric acid, phosphoric acid, nitric acid, and the like), and salts formed with organic acids (such as e.g. acetic acid, oxalic acid, tartaric acid, succinic acid, malic acid, ascorbic acid, benzoic acid, tannic acid, palmitic acid, polyglutamic acid, naphthalene sulphonic acid, naphthalene disulphonic acid, polygalacturonic acid and the like); (b) base additional salts formed with metal cations such as zinc, calcium, bismuth, barium, magnesium, aluminum, copper, cobalt, nickel, cadmium, sodium, potassium and the like, or with a cation formed from ammonia, N,N-dibenzylethylenediamine, D-glucosamine, tetraethylammonium or ethylenediamine; or (c) combinations of (a) and (b); e.g. a zinc tannate or the like.

Pharmaceutically acceptable salts include salts of compounds of the invention that are safe and effective for use in mammals and that possess a desired therapeutic activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention may form pharmaceutically acceptable salts with various amino acids. Suitable base salts include, but are not limited to, aluminum, calcium, lithium, magnesium, potassium, sodium, zinc, and diethanolamine salts. For additional information on some pharmaceutically acceptable salts that can be used to practice the invention please reviews such as Berge, et al., 66 J. PHARM. SCI. 1-19 (1977), Haynes, et al, J. Pharma. Sci., Vol. 94, No. 10, October 2005, pgs. 2111-2120 and See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

Pharmaceutical formulation: The compounds of the invention and their salts may be formulated as pharmaceutical compositions for administration. Such pharmaceutical compositions and processes for making the same are known in the art for both humans and non-human mammals. See, e.g., Remington: the Science and Practice of Pharmacy, (A. Gennaro, et al., eds., $19^{th}$ ed., Mack Publishing Co., 1995). Formulations can be administered through various means, including oral administration, parenteral administration such as injection (intramuscular, subcutaneous, intravenous, intraperitoneal) or the like; transdermal administration such as dipping, spray, bathing, washing, pouring-on and spotting-on, and dusting, or the like. Additional active ingredients may be included in the formulation containing a compound of the invention or a salt thereof.

The pharmaceutical formulations of the present invention include those suitable for oral, parenteral (including subcutaneous, intradermal, intramuscular and intravenous) and rectal administration. The formulations may be presented in unit dosage form and may be prepared by any of the methods known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or non-aqueous liquid such as a syrup, elixir or a draught, or as an oil-in-water liquid emulsion or a water-in-oil liquid emulsion. The formulation may also be a bolus, electuary or paste.

The pharmaceutical formulations of the present invention suitable for parenteral administration include aqueous and non-aqueous sterile injection solutions, and may also include an antioxidant, buffer, a bacteriostat and a solution which renders the composition isotonic with the blood of the recipient, and aqueous and non-aqueous sterile suspensions which may contain, for example, a suspending agent and a thickening agent. The formulations may be presented in a single unit-dose or multi-dose containers, and may be stored in a lyophilized condition requiring the addition of a sterile liquid carrier prior to use.

Pharmaceutically acceptable carrier: Pharmaceutically acceptable carrier, unless stated or implied otherwise, is used herein to describe any ingredient other than the active component(s) that may be included in a formulation. The choice of carrier will to a large extent depend on factors such as the particular mode of administration, the effect of the carrier on solubility and stability, and the nature of the dosage form.

A tablet may be made by compressing or moulding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

Fatty acid synthase (FASN) is the sole cytosolic enzyme in mammalian cells responsible for de novo lipid synthesis. FASN is not required for most non-lipogenic tissues due to high fat of modern diet, but essential for cancer cell survival and contributes to cancer drug resistance. FASN has also been suggested to contribute to insulin resistance in diabetes. Thus, FASN is an attractive target for drug discovery. Unfortunately, there is no FDA-approved drug targeting FASN for treating these diseases. In this study, it is demonstrated that proton pump inhibitors (PPIs), approved for treating digestive disorders, effectively inhibit FASN in and suppress survival of human breast cancer cells. PPIs also help overcome doxorubicin and radiation resistance in these cells by suppressing DNA damage repair via inhibiting FASN activity and PARP1 expression.

Figure 1:
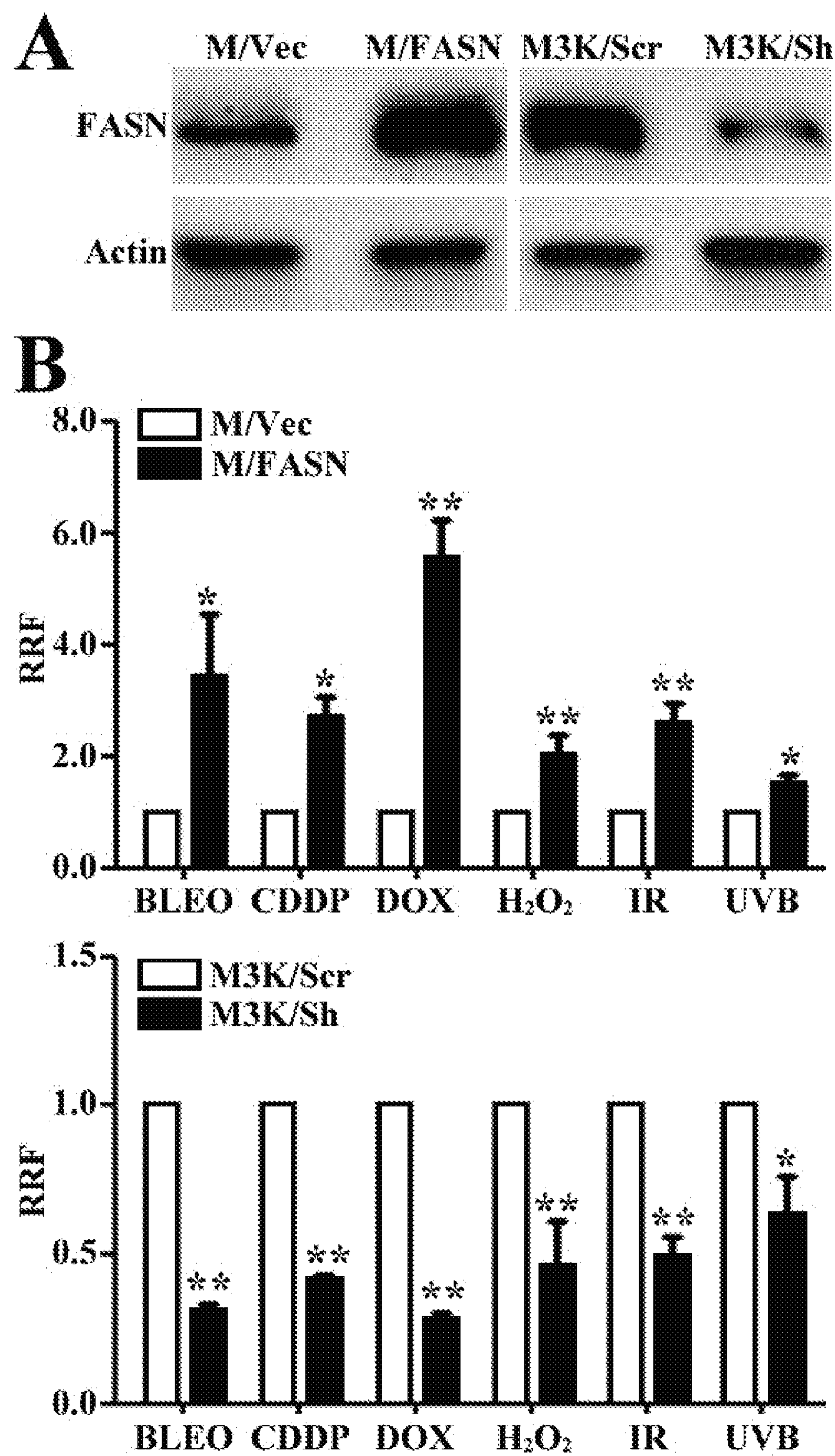
FIG. 1. Effect of FASN on cellular response to genotoxic treatments. A, Western blot analyses of FASN expression in stable MCF7 cells with FASN over-expression (M/FASN), MCF7/AdVp3000 cells with stable FASN knockdown (M3K/Sh), and their respective control vector-transfected (M/Vec) and scrambled control shRNA-transfected (M3K/Scr) cells. B, Survival assay. M/FASN, M3K/Sh, and their respective control cells were tested for resistance to bleomycin (BLEO), cisplatin (CDDP), doxorubicin (DOX), $H_2O_2$ using MTT assay and to ionizing radiation (IR) and UVB using colony formation assay. (n=3, $*p<0.05$; $**p<0.01$).
Figure 8:
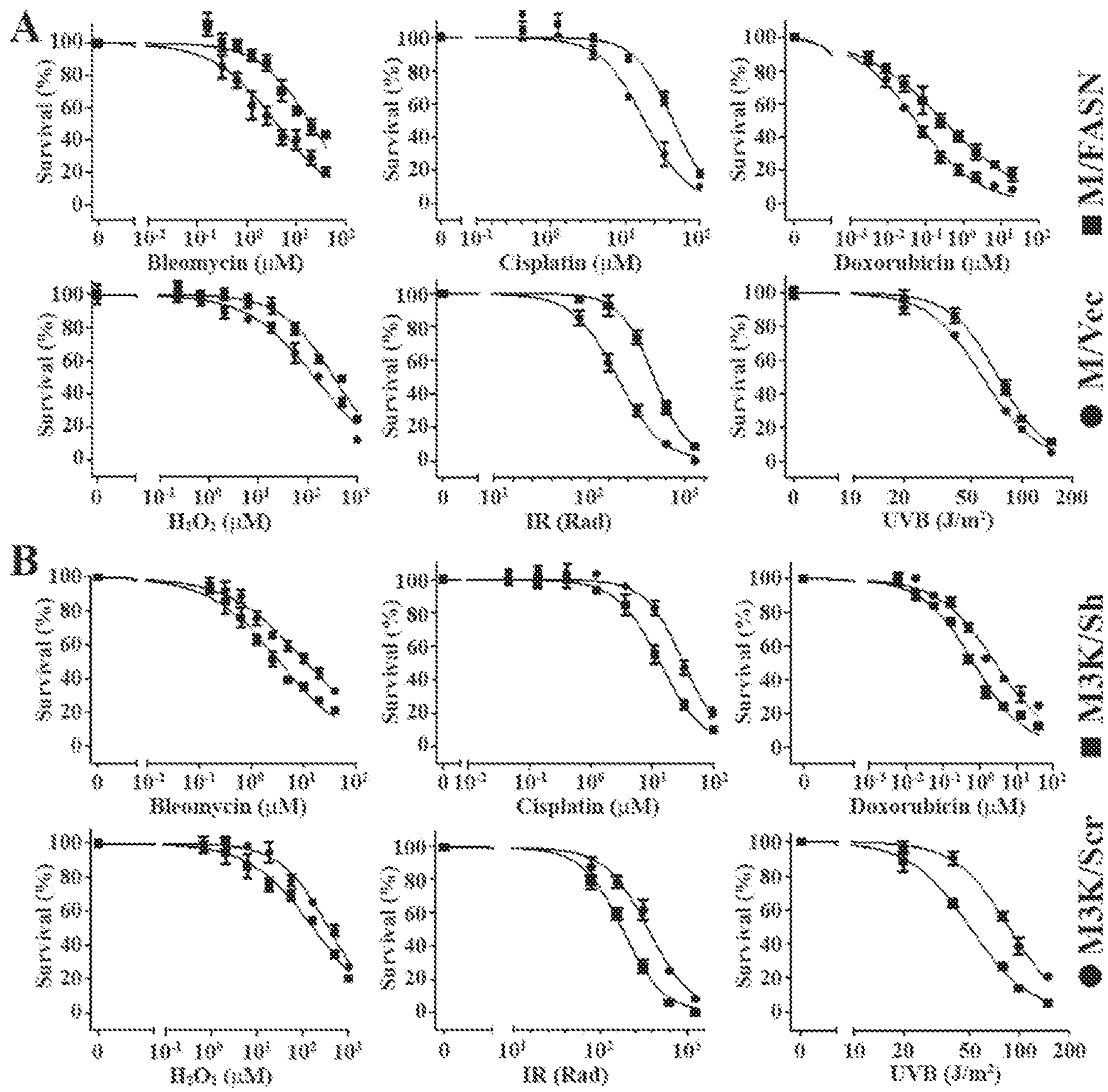
FIG. 8. Representative dose-response curves for survival assays. M/FASN with FASN over-expression (A), M3K/Sh with FASN knockdown (B), and their respective control cells (M/Vec and M3K/Scr) were tested for resistance to bleomycin (BLEO), cisplatin (CDDP), doxorubicin (DOX), and $H_2O_2$ using MTT assay and to ionizing radiation (IR) and UVB using colony formation assay. Representative survival curves are shown and expressed as % of survival to untreated controls. Each data point represents the mean±standard deviation for n=6 replicates.

FASN over-expression causes resistance to multiple genotoxic treatments. It was previously reported that FASN over-expression increased cellular resistance to anticancer drugs that cause DSB but not to non-DNA-damaging drugs. To determine if FASN over-expression causes resistance to genotoxic treatments that cause different types of DNA lesions, the survival of a previously established stable MCF7 clone with FASN over-expression (M/FASN) in comparison with vector-transfected (M/Vec) control cells (see FIG. 1A) was determined following treatments with bleomycin, cisplatin, doxorubicin, $H_2O_2$, ionizing radiation (IR), and UVB. Now referring to FIG. 1B and FIG. 8A, M/FASN cells are significantly more resistant to all these treatments than M/Vec cells. Stable FASN knockdown (M3K/Sh) in a drug resistant MCF7/AdVp3000 cell line (FIG. 1A), which has elevated endogenous FASN level than the parental MCF7 cells, significantly reduced resistance level to these treatments compared to the control cells (M3K/Scr) (FIG. 1B and FIG. 8B). Thus, FASN over-expression likely contributes to cellular resistance to multiple genotoxic treatments that cause different types of DNA lesions.

FASN over-expression increases repair of IR and doxorubicin-induced DNA damages. The above findings suggest that FASN over-expression may protect cells against DNA damages induced by these genotoxic treatments or by increasing the repair of these damages. This possibility, was tested by focusing on DSB induced by IR, in part because of the convenience of monitoring repair and in part because DSBs appear to be mostly affected by FASN (FIG. 1B). First a neutral comet assay with the two paired cell lines (M/FASN vs M/Vec and M3K/Sh vs M3K/Scr) following IR treatment was performed. Now referring to FIG. 2A, at 1 hour following IR treatment, the reported time of maximal DNA damage induction post IR exposure (see e.g., Wang H, Wang M, Bocker W, & Iliakis G (2005) Complex H2AX phosphorylation patterns by multiple kinases including ATM and DNA-PK in human cells exposed to ionizing radiation and treated with kinase inhibitors. *J Cell Physiol* 202(2): 492-502), both M/FASN and M/Vec cells formed similarly elongated tails with no difference in olive tail moment, indicating that the DNA in both cells are equally damaged by IR and that FASN over-expression may not protect cells from IR-induced DNA damages. Similar results were also observed for M3K/Sh and M3K/Scr cells (FIG. 2B). However, at 4 hours after IR, a dramatic difference in olive tail moment was observed between M/FASN and M/Vec cells and between M3K/Sh and M3K/Scr cells. While the Olive tail moment was significantly lower in M/FASN cells, it was significantly higher in M3K/Sh cells than their respective control cells. These findings indicate that FASN may increase cellular repair activity of DSBs induced by IR.

Figure 2:
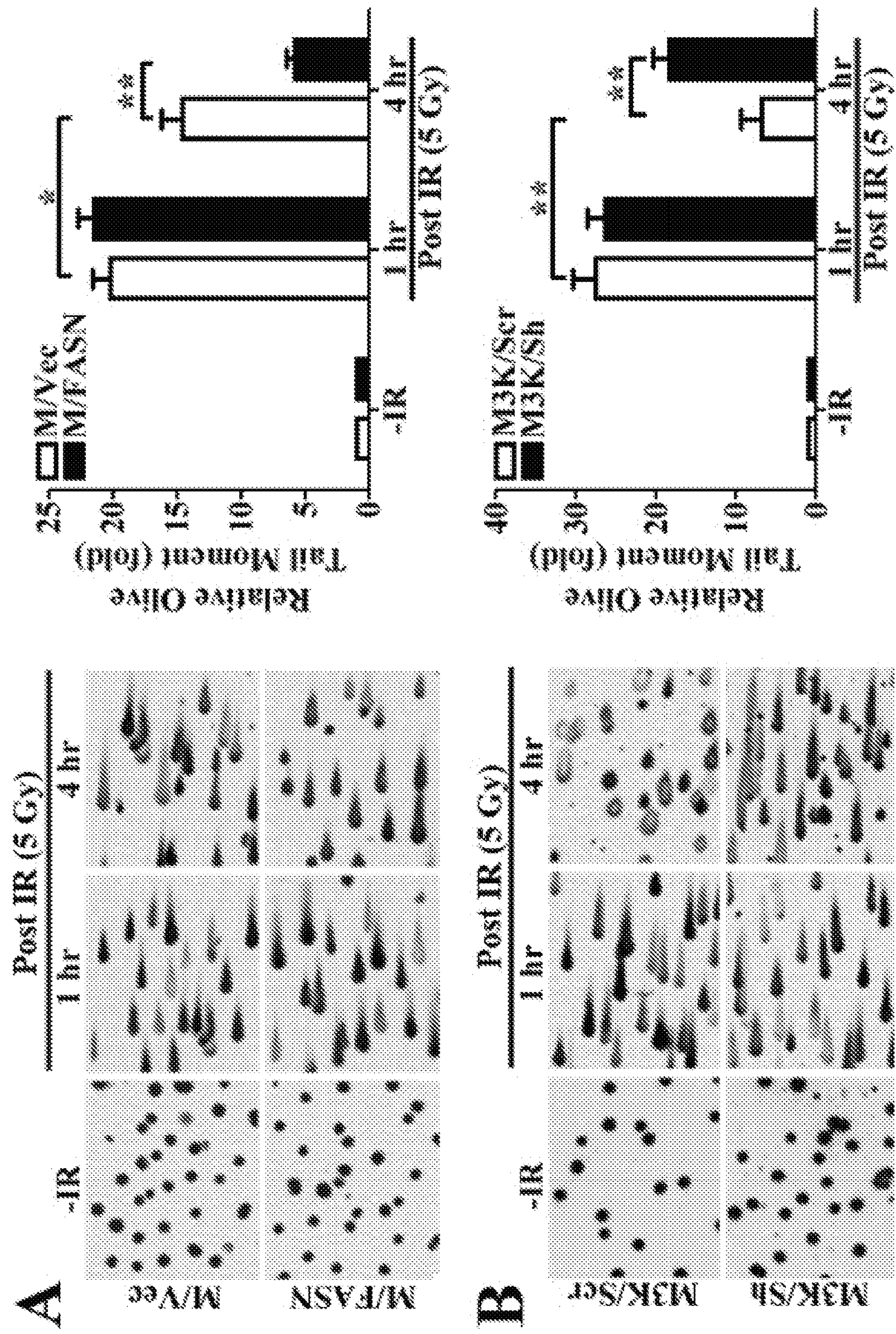
FIG. 2. Effect of FASN on accumulation of IR-induced DNA damages. Stable FASN overexpressing (M/FASN) and the control (M/Vec) cells (A) as well as stable FASN knockdown (M3K/Sh) and the control (M3K/Scr) cells (B) were treated with or without 5 Gy of IR and then subjected to neutral comet assay at different times. The histograms show quantitative olive moment analyses from three independent experiments ($*p<0.05$; $**p<0.01$).

In order to verify the afore-mentioned findings, the level of γ-H2AX, an indicator of DSBs, in these paired cells at different recovery times following IR was determined by Western blot analysis. Now referring to FIGS. 3A-3B, similarly induced level of γ-H2AX was detected between M/FASN and M/Vec cells and between M3K/Sh and M3K/Scr cells at 1 hour following IR compared to their respective untreated control cells. However, γ-H2AX level decreased significantly more in M/FASN than M/Vec control cells and decreased significantly less in M3K/Sh than M3K/Scr control cells at 4 hours following IR. These observations are consistent with the findings of the comet assay (FIG. 2). Immunofluorescence analysis of M3K/Sh and M3K/Scr cells showed equivalent increases in punctate staining of γ-H2AX in the nuclei of both cells at 1 hour after IR compared to the control untreated cells (FIG. 3D). At 4 hours after IR, the nuclear staining of γ-H2AX in M3K/Scr control cells reduced dramatically while it remained at high level in M3K/Sh cells with FASN depleted. These observations are consistent with those shown by Western blot analysis of γ-H2AX expression.

Because M3K/Scr vs M3K/Sh and M/Vec vs M/FASN cells in above studies are of the same MCF7 origin, the above observations may be specific to MCF7 cells. In order to eliminate this possibility, another pair of cell lines of different genetic background, P/FASN (with ectopic FASN over-expression) and P/Vec (vector-transfected control) were tested, both derived from Panc-1 cells (FIG. 3C). While γ-H2AX level was similarly high between P/FASN and P/Vec cells at 1 hour following IR treatment, it was significantly reduced in P/FASN cells compared with P/Vec cells at 4 hours following IR treatment (FIG. 3C). This finding is confirmed by the punctate staining of γ-H2AX in the nuclei of P/FASN and P/Vec cells (FIG. 3D). Thus, the function of FASN in promoting DSB repair may not be cell line specific.

Figure 9:
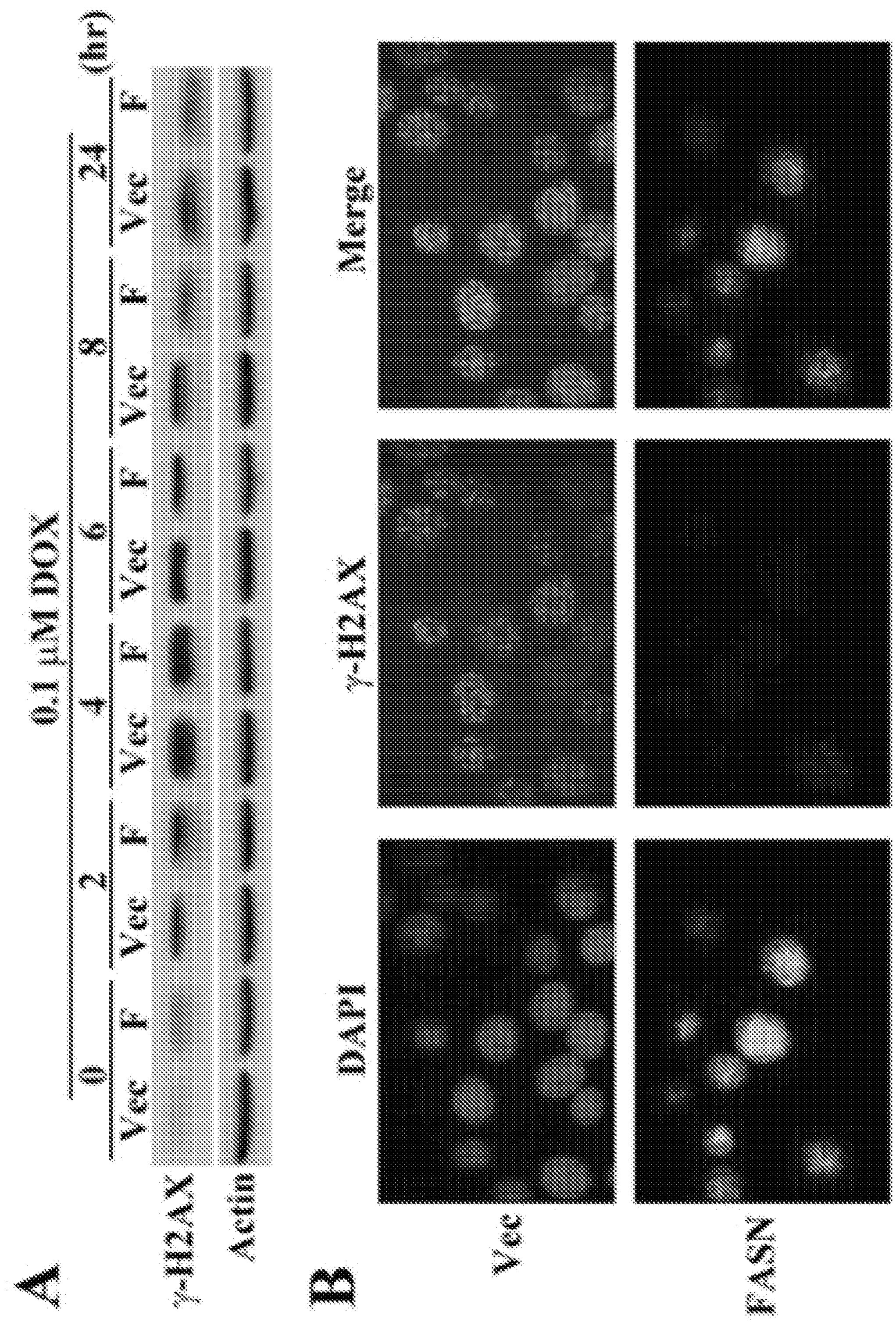
FIG. 9. Effect of FASN on γ-H2AX level following doxorubicin treatments. A, Western blot analysis (A) and immunofluorescence staining (B) of doxorubicin induced γ-H2AX in MCF7-derived FASN-overexpressing (M/FASN) and control vector-transfected cells (M/Vec). Cells were treated with 0.1 μM doxorubicin and collected at the designated time points. Immunofluorescence staining was done at 24 h post doxorubicin treatment.

Because FASN over-expression contributes to cellular resistance to anticancer drug doxorubicin (FIG. 1), which also induces DSBs, it was determined if FASN over-expression has a similar effect on γ-H2AX due to DSB induced by doxorubicin. Now referring to FIG. 9A, at 4 hours of treatment, γ-H2AX reached maximum level in both M/FASN and control M/Vec cells. At 6 hours and beyond, M/FASN cells have less γ-H2AX than the control M/Vec cells. This observation is also corroborated by immunostaining of γ-H2AX in nuclei shown in FIG. 9B. Together, these findings suggest that higher FASN expression level may increase the repair of IR- or doxorubicin-induced DSB.

Figure 10:
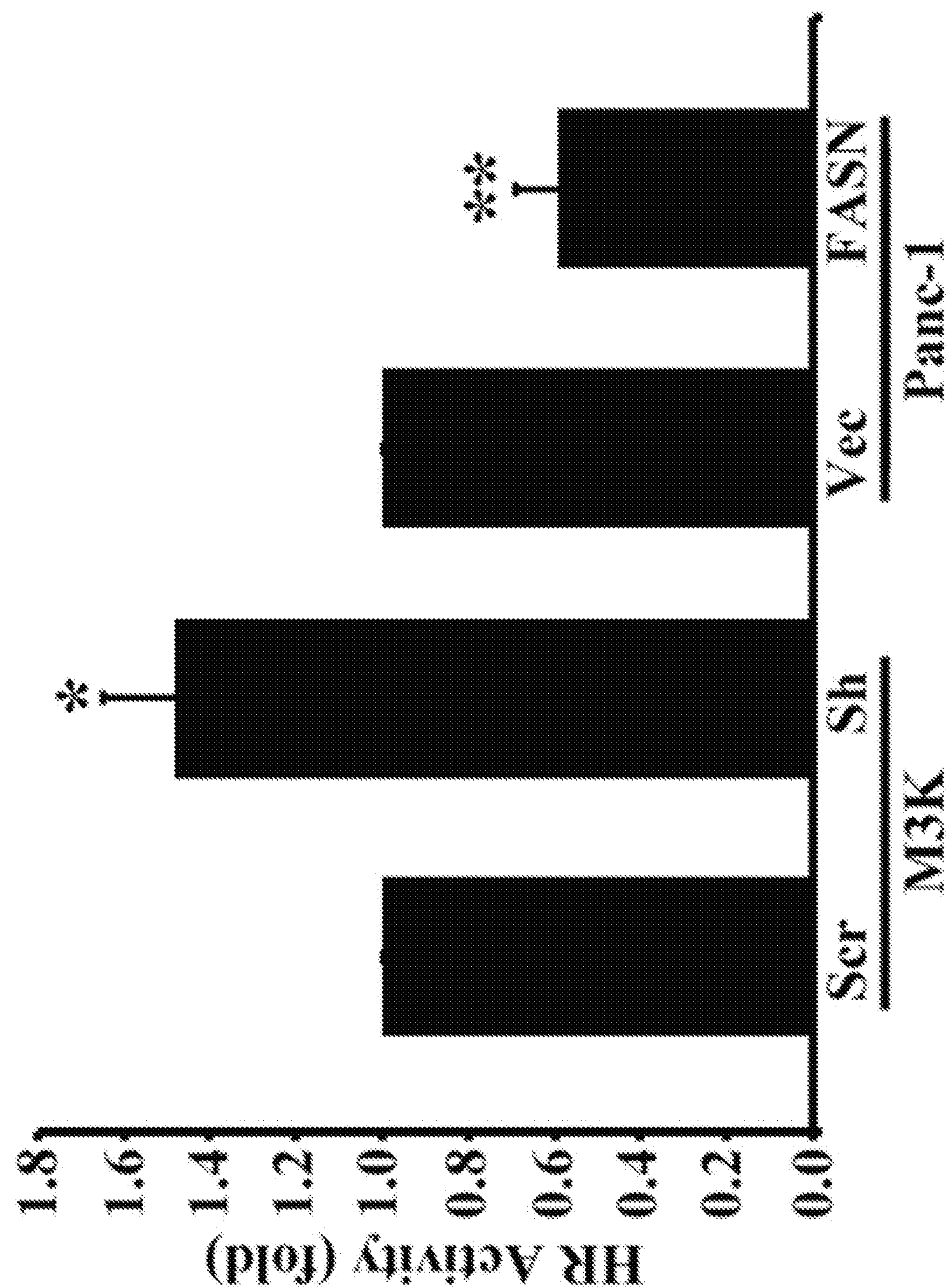
FIG. 10. Effect of FASN expression on HR activity. M3K cells with FASN knockdown (M3K/Sh) and Panc-1 cells with FASN over-expression (P/FASN) along with their respective control cells (M3K/Scr and P/Vec) were subjected to HR assay as described in Experimental Procedures. (n=3, *p<0.05, **p<0.01).

FASN over-expression increases NHEJ repair activity. Next tested was the possibility that FASN over-expression increases the repair of DSB was tested using reporter-based host-cell reactivation assay of both NHEJ and HR activities without drug or IR treatments. Now referring to FIG. 3E, M3K/Sh cells with FASN knockdown had significantly reduced NHEJ activity than the control M3K/Scr cells while P/FASN cells with FASN over-expression had significantly increased NHEJ activity than the control P/Vec cells. However, the HR activity was significantly increased and reduced, respectively, in M3K/Sh and P/FASN cells compared with their control cells (FIG. 10). These findings are very interesting and suggest that NHEJ but not HR may contribute to FASN-induced resistance to IR (see below).

Figure 4:
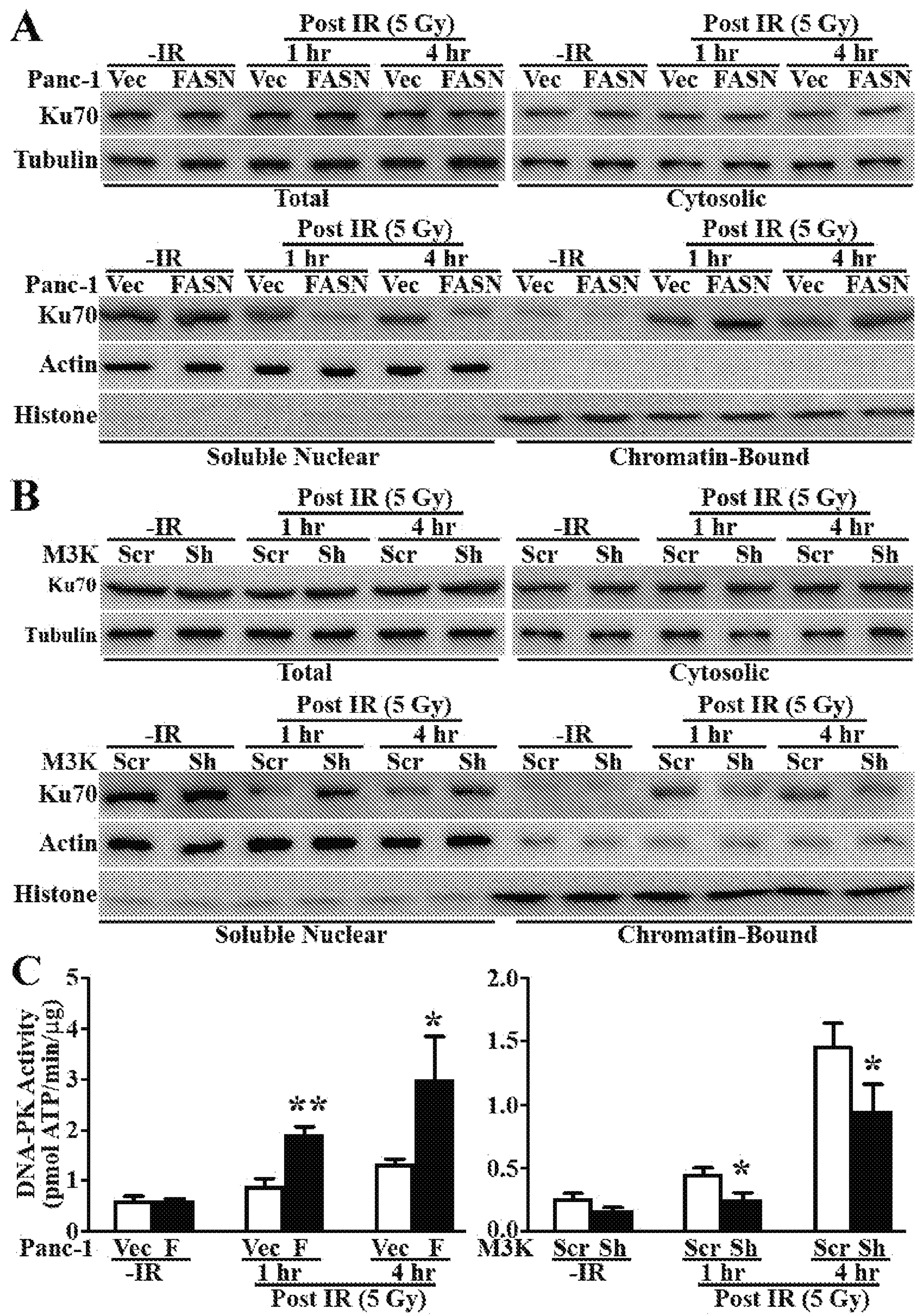
FIG. 4. Effect of FASN on Ku recruitment and DNA-PK activity. A-B, Western blot analysis of Ku70 distribution in different cellular fractions following IR in FASN-over-expressing Panc-1 cells (P/FASN) (A), FASN-knockdown MCF7/AdVp3000 cells (M3K/Sh) (B), and their respective control cells (P/Vec and M3K/Scr). Tubulin, actin, and histone H3 were used as markers for cytosolic, soluble nuclear, and insoluble chromatin fractions, respectively. C, DNA-PK activity assay. P/FASN and M3K/Sh cells together with their respective control P/Vec and M3K/Scr cells were treated without or with IR and harvested at indicated times following IR for determination of DNA-PK activity (n=3, *p<0.05; **p<0.01).

FASN over-expression enhances Ku protein recruitment and DNA-PK activity. Investigated next was the molecular basis of the up-regulated NHEJ activity by FASN over-expression. Because NHEJ repair is initiated by recruiting Ku70/80 dimers and DNA-PKcs to the damage sites and because increased Ku70 expression has been found to promote cellular resistance to doxorubicin and ionizing radiation, the effect of FASN on Ku70 expression and recruitment to damaged chromatin was tested. Now referring to FIGS. 4A and 4B, M3K/Sh cells with FASN knockdown and P/FASN cells with FASN over-expression had similar total and cytoplasmic Ku70 level as their respective control cells before and after IR. The chromatin-bound Ku70 was increased in all cells following IR treatment. However, the increase was more in P/FASN cells and less in M3K/Sh cells compared with their respective control cells. These changes were accompanied with the corresponding lower and higher levels of Ku70 in the unbound (soluble) nuclear fractions than their respective controls. Further, more chromatin-bound Ku70 protein in P/FASN and less in M3K/Sh cells were accompanied with significantly augmented and reduced DNA-PK activity following IR compared with their respective controls (FIG. 4C). This indicated that FASN over-expression increases recruitment of Ku proteins to chromatin and DNA-PK activity following IR-induced DNA damages.

Figure 3:
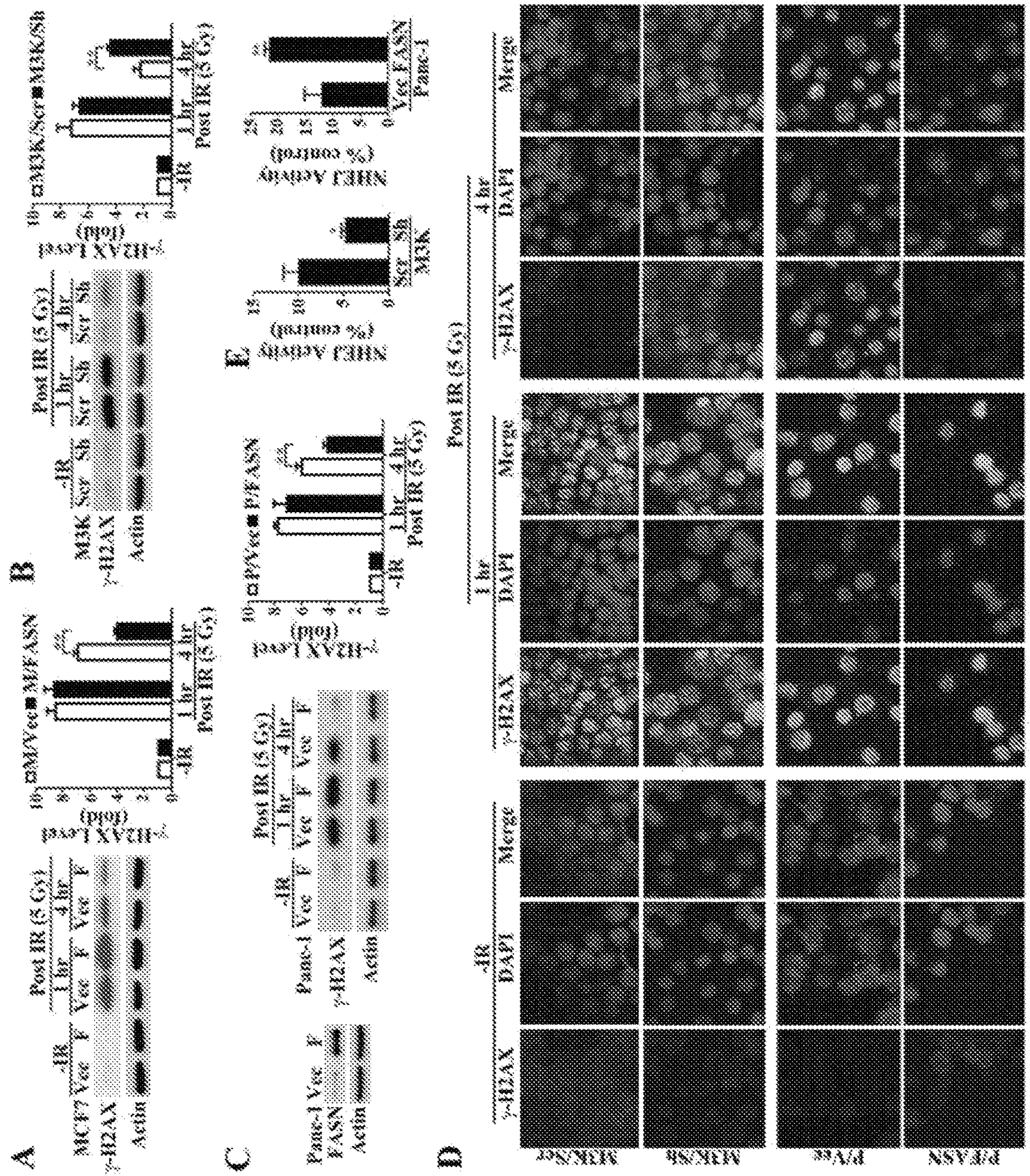
FIG. 3. Effect of FASN on DSB repair. A-C, Western blot analysis of IR-induced γ-H2AX in FASN-overexpressing MCF7 (M/FASN) and its control (M/Vec) cells (A), in stable FASN knockdown MCF7/AdVp3000 (M3K/Sh) and its control (M3K/Scr) cells (B), and in FASN-over-expressing Panc-1 (P/FASN) and its control (P/Vec) cells (C). Histograms show relative γ-H2AX levels determined from three independent experiments (**p<0.005). D, Immuno-fluorescence staining of γ-H2AX in M3K/Sh, P/FASN, and their respective control M3K/Scr and P/Vec cells. DNA was stained by DAPI. E, NHEJ activity of M3K/Sh and P/FASN cells along with their respective control M3K/Scr and P/Vec cells determined using host cell reactivation (HCR) NHEJ assay (n=4, *p<0.05; **p<0.01).
Figure 11:
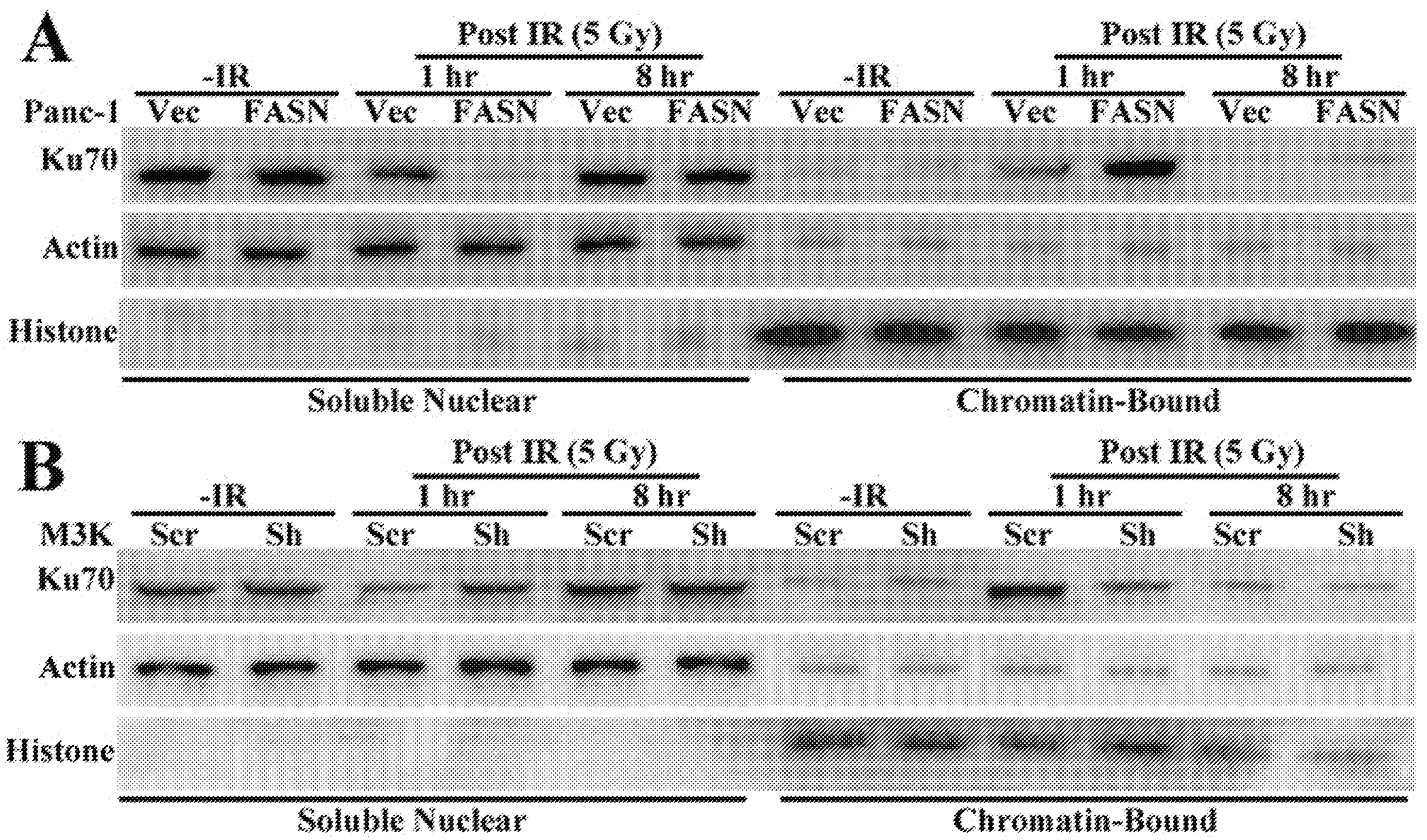
FIG. 11. Western blot analysis of Ku70 distribution in different nuclear fractions following IR in FASN-over-expressing Panc-1 (P/FASN) (A), FASN-knockdown MCF7/AdVp3000 (M3K/Sh) (B), and their respective control cells (P/Vec and M3K/Scr). Actin and histone H3 were used as markers for soluble nuclear and insoluble chromatin fractions, respectively.

It is noteworthy that Ku70 binding to chromatin and DNA-PK activity were sustained at 4 hours post IR, when most DNA damages were repaired as evidenced by the significant decrease in γ-H2AX level/foci and reduction in olive tail moment (FIG. 2 and FIG. 3). It is possible that the sustained Ku70 retention on chromatin was due to existence of residual DNA damages at 4 hours post IR also as indicated by γ-H2AX level/foci and olive tail moment (FIGS. 2A and 2B, and FIGS. 3 A, B, and C). In order to test this possibility, chromatin-bound Ku70 at 8 hours post IR was analyzed. Now referring to FIG. 11, the chromatin-bound Ku70 was reduced to the basal level. Thus, the sustained chromatin-retention of Ku70 and DNA-PK activity may be due to cellular activity to repair residual DNA damages.

Figure 5:
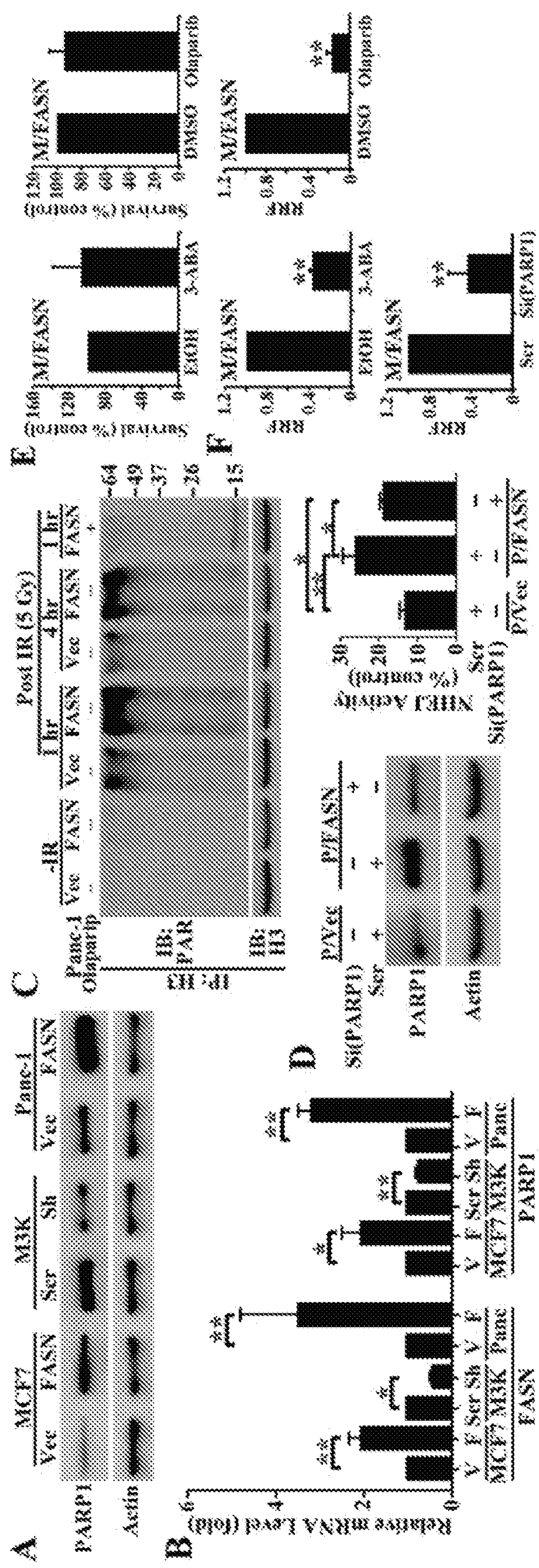
FIG. 5. PARP-1 mediates FASN-associated DNA repair and genotoxic treatment resistance. A-B, Effect of FASN on PARP-1 expression as determined by Western blot (A) and real-time RT-PCR (B) in stable FASN-over-expressing and -knockdown cells. C, Effect of FASN on IR-induced histone-H3 PARylation. Cells were pre-treated without or with 0.5 μM olaparib followed by treatment with or without IR and harvested at different times following IR for lysate preparation, immunoprecipitation of histone-H3 in the presence of 100 μM PARG inhibitor, gallotannin, and Western blot analyses of PARylated and total histone H3. D, Effect of PARP-1 knockdown on FASN-induced NHEJ up-regulation. FASN-over-expressing (P/FASN) and the control (P/Vec) cells were transiently transected with PARP-1 or scrambled control siRNA followed by Western blot analysis of PARP-1 (left panel) and NHEJ activity assay (right panel) (n=3, *p<0.05; **p<0.01). E, Effect of PARP-1 inhibition on survival. M/FASN cells were treated with 1 mM 3-ABA, 0.5 μM olaparib, or their vehicle control for 48 hours followed by MTT assay. F, Effect of PARP-1 inhibition on doxorubicin resistance. M/FASN cells were pre-treated for 6 hours by 1 mM 3-ABA, 0.5 μM olaparib, or transfected with control or PARP-1 siRNA followed by tested doxorubicin resistance using MTT survival assay. (n=3-4, *p<0.05, **p<0.01).

FASN-over-expression promotes PARP-1 expression, which mediates FASN enhancement of NHEJ repair and cellular resistance to IR. Poly (ADP-ribose) polymerase 1 (PARP-1) has emerged as a key player in DSB repair pathway and was found to promote recruitment and retention of Ku at DSB sites via Ku70 binding to PARylated nuclear proteins and facilitates the NHEJ repair. Thus, the possibility that FASN over-expression up-regulates PARP-1 expression, which in turn promotes Ku70 recruitment and increases NHEJ activity was tested. Now referring to FIG. 5A, PARP-1 protein is increased dramatically in M/FASN and P/FASN clones with FASN-over-expression but decreased in the stable M3K/Sh clone with FASN-knockdown compared with their respective control cells. PARP-1 mRNA also changed similarly as PARP-1 protein in these cells (FIG. 5B).

Next examined was if increased PARP-1 expression due to FASN-over-expression would lead to higher PARP activity following DNA damage by determining Poly (ADP-ribosyl)ated (PARylated) histone-H3, a target of PARP-1 after DNA damage and relevant to DNA repair. For this purpose, the stable P/FASN clone and its P/Vec control cells were treated without or with 5 Gy IR, followed by immunoprecipitation of histone-H3 and Western blot analysis of PARylated histone-H3. Now referring to FIG. 5C, PARylated histone-H3 was increased in P/FASN cells compared with the control P/Vec cells following IR. Pre-treatment with the PARP-1 inhibitor, olaparib, inhibited IR-induced PARylation with minimal remaining PARylation of histone-H3 (FIG. 5C). Clearly, the increased PARP-1 expression is accompanied with increased PARP-1 activity.

In order to determine if the increased PARP-1 mediates FASN enhancement of NHEJ activity, P/FASN cells were transiently transfected with PARP-1 siRNA to knockdown PARP-1 expression followed by NHEJ activity assay. Now referring to FIG. 5D, the increased PARP-1 level in P/FASN cells due to FASN over-expression is successfully suppressed by PARP-1 siRNA. The increased NHEJ activity due to FASN over-expression in P/FASN cells is significantly reduced by PARP-1 knockdown. Together, these findings suggest that FASN up-regulates PARP-1 expression, which in turn increases NHEJ activity possibly by promoting Ku recruitment and enhancing DNA-PK activity.

Figure 12:
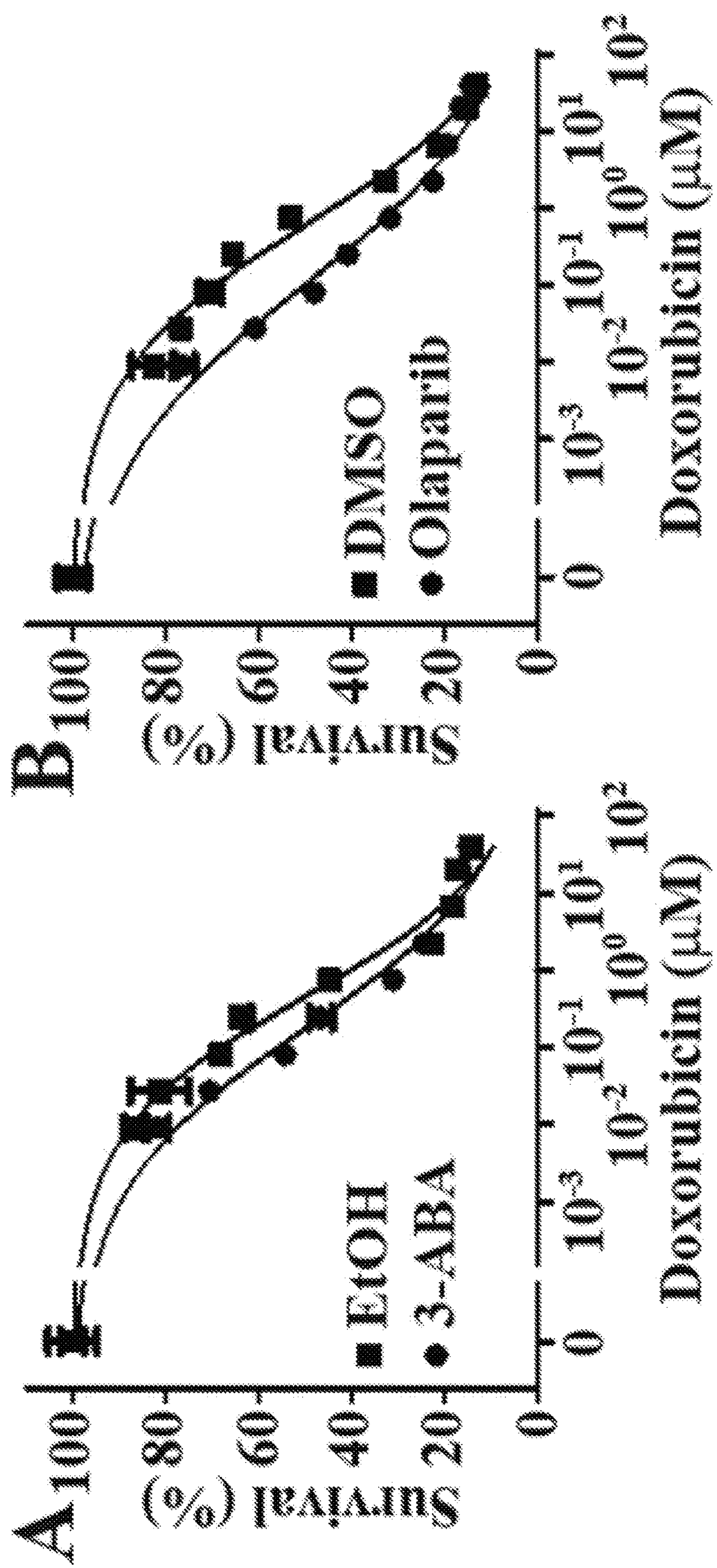
FIG. 12. Representative dose-response curves for survival assays. M/FASN cells were pre-treated with 1 mM 3-ABA (A), 0.5 μM olaparib (B) or their respective vehicle controls before subjected to MTT assay in the presence of different concentrations of doxorubicin. Representative survival curves are shown and expressed as % of survival controls without doxorubicin.

To determine if FASN enhancement of PARP-1 likely mediates FASN function in cellular resistance to DNA damages, a survival assay of P/FASN cells following doxorubicin treatment in the absence or presence of PARP-1 inhibitors, 3-ABA (3-aminobenzamide) or olaparib was carried out. Now referring to FIG. 5E, either 1 mM 3-ABA or 0.5 μM olaparib alone had no effect on M/FASN cell survival. However, 1 mM 3-ABA and 0.5 μM olaparib significantly reduced the doxorubicin resistance level of M/FASN cells (FIG. 5F and FIG. 12). Similarly, knocking down PARP-1 using siRNA also significantly sensitized M/FASN cells to doxorubicin (FIG. 5F). These findings suggest that PARP-1 likely mediates FASN over-expression-induced resistance to DSB possibly by increasing NHEJ repair of DSB.

Figure 13:
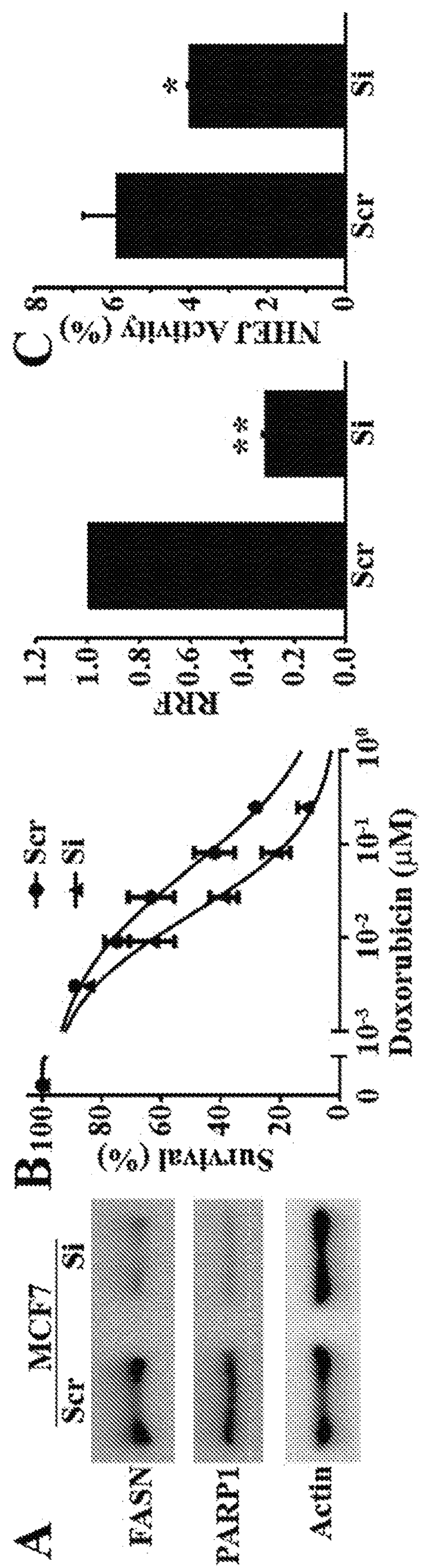
FIG. 13. Effect of FASN knockdown on doxorubicin response, NHEJ repair, and PARP-1 expression in MCF7 cells. MCF7 cells were transiently transfected with FASN siRNA followed by Western blot analysis of FASN, PARP-1, and loading control actin (A), MTT survival assay in the presence of doxorubicin (B), and NHEJ activity assay (C). (n=3, *p<0.05; **p<0.01).

Both MCF7 and Panc-1 cells are known to express high level of endogenous FASN and M3K cells have further elevated endogenous FASN. To eliminate the possibility that the above observations are peculiar due to the forced increase in FASN expression either by ectopic transfection or drug selection, FASN levels were transiently knocked down in the parental MCF7 cells and the effect of this change on doxorubicin sensitivity, NHEJ activity, and PARP-1 expression was tested. Now referring to FIG. 13, FASN knockdown in MCF7 cells significantly reduced doxorubicin resistance, NHEJ activity, and PARP-1 expression. These findings are consistent with previous observations that FASN knockdown in MDA-MB-468 cells also significantly reduced doxorubicin and mitoxantrone resistance. Thus, endogenous levels of FASN in cancer cells likely regulate cellular response to DNA damages and NHEJ repair of DSBs.

Figure 6:
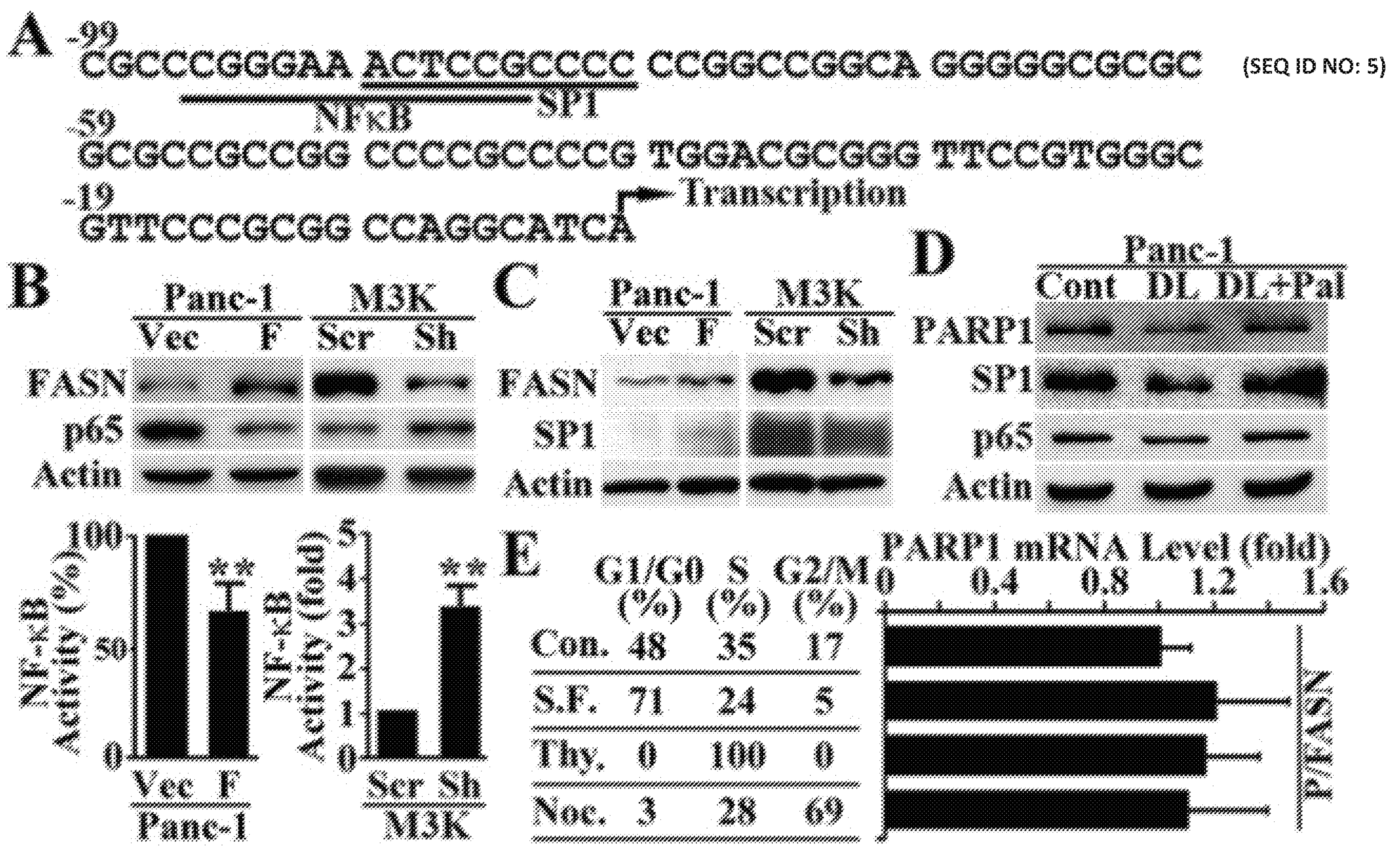
FIG. 6. Effect of FASN on p65 and SP1 expression. A, Putative composite element in the human PARP-1 proximal promoter (SEQ ID NO: 5). The overlapping underlined sequences represent NF-κB and SP1-binding sites. The numbers indicate positions relative to the transcription start site (arrow). B, Effect of FASN over-expression in Panc-1 cells or knockdown in MCF7/AdVp3000 cells on p65 expression and NF-κB activity. C, Effect of FASN over-expression in Panc-1 cells or knockdown in MCF7/AdVp3000 cells on SP1 expression. D, Effect of de-lipidation and palmitate supplementation in culture on SP1 and p65 expression in Panc-1 cells. E, Effect of cell cycle distribution on PARP-1 expression as determined using real-time RT-PCR. Different cell cycle stages were achieved by culturing P/FASN cells in serum-free (S.F) media for G0/G1, thymidine (Thy) block for S, and nocodazol (Noc) treatment for G2/M phases.

FASN transcriptionally regulates PARP-1 expression through inhibition of NF-κB and up-regulation of SP1. Now referring to FIG. 5B, the mRNA level of PARP-1 was increased by FASN over-expression and decreased by FASN knockdown, suggesting that FASN may participate in regulating PARP-1 transcription. To understand how FASN promotes PARP-1 transcription, the promoter sequence of human PARP-1 was examined and a composite element with overlapping binding sites for NF-κB and SP-1 transcription factors (FIG. 6A) was found. Previously, it has been shown that the rat PARP-1 gene is activated by SP1 and inactivated by NF1, which compete with SP1 on a composite element in the promoter of rat PARP-1. It was also shown that FASN down-regulates NF-κB expression. Now referring to FIG. 6B, FASN over-expression in Panc-1 cells and knockdown in MCF7/AdVp3000 (M3K) cells also significantly decreased and increased, respectively, p65 expression as determined using Western blot and NF-κB activity using reporter assay. On the other hand, FASN over-expression increased SP1 expression while FASN knockdown reduced SP1 expression (FIG. 6C). It also tested if the effect of FASN on SP1 and NF-κB expression is possibly via its catalytic product palmitate, this was done by culturing cells in de-lipidated serum with or without palmitate supplementation. Now referring to FIG. 6D, culturing Panc-1 cells in media with de-lipidated serum reduced the expression of SP1 and PARP-1, but not NF-κB. Supplementation of palmitate rescued both SP1 and PARP-1 expression from the suppression. However, altering cell cycle in P/FASN cells had no effect on PARP-1 expression (FIG. 6E). Thus, palmitate may play an important role in mediating FASN regulation of SP1 expression but not NF-κB.

Figure 7:
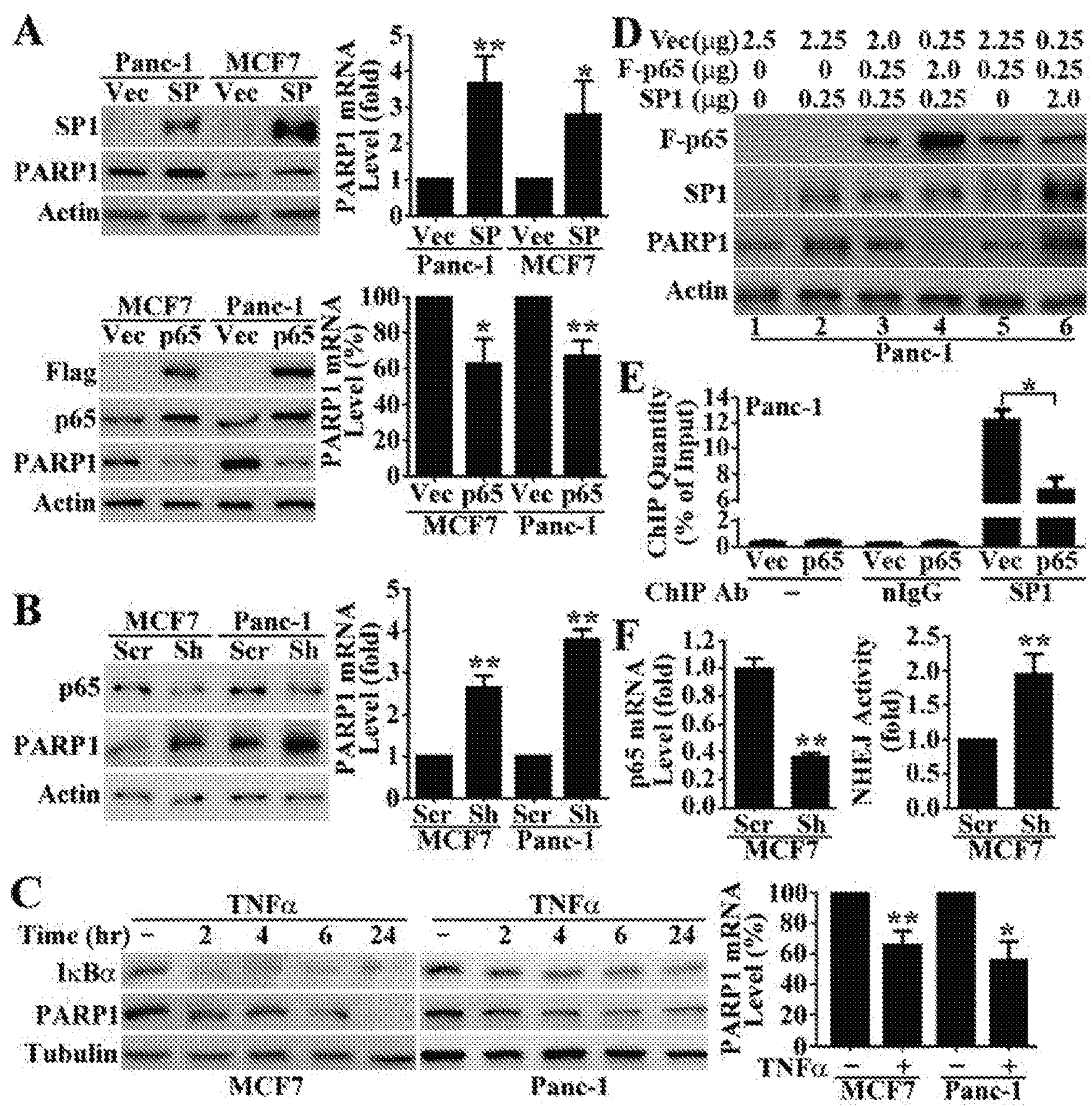
FIG. 7. NF-κB and SP1 regulate PARP-1 transcription by binding to the same site. A, Effect of SP1 or Flag-p65 over-expression on PARP-1 expression in MCF7 and Panc-1 cells as determined by Western blot analyses (left panels) and qRT-PCR (right panels). B, Effect of shRNA-induced p65 knockdown on PARP-1 expression in MCF7 and Panc-1 cells as determined using Western blot (left panel) and qRT-PCR (right panel). C Effect of NF-κB activation by TNF-α treatment on PARP-1 expression in MCF7 and Panc-1 cells as determined by Western blot and qRT-PCR analysis. D, Competition between p65 and SP1 in regulating PARP-1 expression. Panc-1 cells were transiently transfected with various combinations of Flag-p65 and SP1 cDNA together with vector-control to ensure constant total level of DNA for each transfection. Cells were harvested at 48 hours post transfection and subjected to Western blot analysis. E, ChIP assay. Panc-1 cells were transiently transfected with Flag-p65 cDNA (p65) or a vector control (Vec) followed by ChIP without or with normal IgG control or SP1 antibody and real-time PCR analysis. Data are expressed as percentage of signal detected with the non-immunoprecipitated input (10% of total chromatin). F, Effect of shRNA-mediated p65 knockdown on NHEJ activity in MCF7 cells.

Based on above studies, it was hypothesized that FASN promotes PARP-1 expression by suppressing NF-κB and increasing SP1, which bind to the PARP-1 promoter in a mutually exclusive manner. In order to test this hypothesis first it was determined if SP1 and NF-κB regulate PARP-1 expression by transiently transfecting MCF7 and Panc-1 cells with SP1 or p65 cDNA followed by determination of their effect on the expression of endogenous PARP-1. Now referring to FIG. 7A, SP1 over-expression dramatically increased whereas Flag-p65 over-expression significantly reduced PARP-1 protein and mRNA levels. Knocking down p65 using shRNA significantly increased PARP-1 protein and mRNA levels (FIG. 7B), whereas activation of p65 with TNF-α had contrary effect (FIG. 7C). Taken together, these results suggest that NF-κB and SP1 oppose each other in regulating PARP-1 transcription with NF-κB functioning as a suppressor and SP1 as an activator.

To determine if NF-κB interferes with SP1 activation of PARP-1 expression and vice versa, varying amounts of Flag-p65 and SP1 cDNAs were co-transfected into Panc-1 cells followed by determination of PARP-1 expression. Now referring to FIG. 7D, SP1 expression increased PARP-1 protein level (compare lanes 1 and 2). However, SP1-induced increase in PARP-1 protein level was diminished by p65 cDNA in a dose-dependent manner (compare lanes 2, 3, and 4, FIG. 7D). On the other hand, when p65 cDNA was kept constant, increasing SP1 cDNA from 0 to 2 μg resulted in a steady increase in PARP-1 level (compare lanes 5, 3, and 6).

To further determine if NF-κB interferes with SP1 binding to and activation of PARP-1 promoter, chromatin immunoprecipitation (ChIP) assay to quantify SP1-bound PARP-1 promoter following ectopic p65 over-expression in Panc-1 cells was performed. Now referring to FIG. 7E, the PARP-1 promoter immunoprecipitated by SP1 antibody was reduced significantly from ~13% (relative to input) in vector-transfected control cells to ~7% in p65-over-expressing cells. Collectively, these results suggest that NF-κB likely interferes with SP1 binding to and activation of PARP-1 promoter for PARP-1 expression, possibly via competition for binding onto the composite element within the PARP-1 promoter.

Finally, to determine if these transcription factors possibly play any role in up-regulating NHEJ activity, the effect of p65 knockdown on NHEJ activity was analyzed. Now referring to FIG. 7F, p65 shRNA effectively knocked down p65 expression, which led to significant increase in NHEJ activity in MCF7 cells. This finding suggests that down-regulating NF-κB expression by FASN may contribute to the increased NHEJ repair of DSBs.

Figure 14:
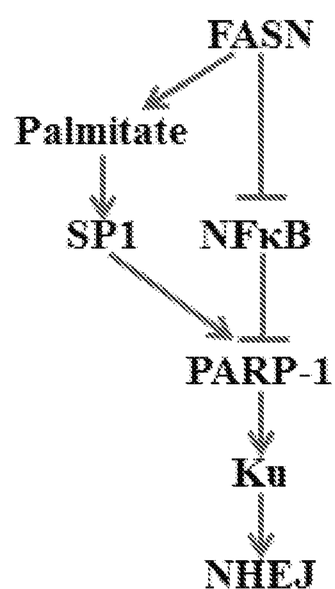
FIG. 14. Schematic representation of FASN regulation on NHEJ Repair of DSB.

Accumulating evidences show that FASN expression is up-regulated in human cancers and provides survival advantages for cancer cells. FASN over-expression has also been associated with resistance to anticancer treatments (see e.g., Liu H, Liu J Y, Wu X, & Zhang J T (2010) Biochemistry, molecular biology, and pharmacology of fatty acid synthase, an emerging therapeutic target and diagnosis/prognosis marker. *Int. J. Biochem. Mol. Biol.* 1(1):69-89). However, the molecular mechanisms of FASN function in drug resistance are largely unknown. The present study shows that FASN over-expression suppresses NF-κB while up-regulates SP1, which in turn increases PARP-1 expression and facilitates recruitment of Ku proteins to the IR or drug-induced DSBs for NHEJ repair. This cascade of events results in resistance to treatments including IR and doxorubicin that elicit DSBs (FIG. 14).

In addition to IR, doxorubicin, and bleomycin, which all cause DSB, it was also found that FASN over-expression contributes to resistance to cisplatin, $H_2O_2$, and UVB that primarily cause other types of DNA lesions repaired by the nucleotide excision repair (NER) and base excision repair (BER) pathways. Because PARP-1 is known to play important roles in both BER and NER pathways, FASN may also contribute to resistance to cisplatin, $H_2O_2$, and UVB by up-regulating NER and BER activities via increasing PARP-1 expression and activity. In line with these findings, over-expression and constitutive hyperactivation of PARP-1 has been associated with cisplatin resistance in non-small cell lung cancer.

As a nuclear enzyme, PARP-1 is activated by DNA damage. Activated PARP-1 post-translationally modifies many nuclear proteins such as histones and DNA repair proteins by adding ADP-ribose polymers onto lysine residues, a process termed Poly (ADP-ribosyl)ation (PARylation) and has been implicated to play important roles in different DNA repair pathways. For NHEJ repair of DSBs, PARP-1 was thought to exercise its role via both DNA-PK-dependent and independent manners. Two other members of the PARP family, PARP-2 and PARP-3, also possess poly (ADP-ribose) polymerase activity. However, PARP-1 is thought to be the major contributor and responsible for over 90% of cellular PARylation. Thus, it is possible that PARP-1 is the major downstream mediator of FASN in NHEJ repair of DSBs.

Currently it is not known how increased PARP-1 enhances Ku recruitment to chromatin for NHEJ repair of DSB. Recently, it was found that PARP in D. discoideum promotes Ku recruitment/retention to chromatin via PARylating nuclear proteins that bind Ku proteins at its C-terminal PAR-binding zinc finger (PBZ) domain. However, human Ku70 and Ku80 do not possess a PBZ domain. Thus, human Ku proteins unlikely bind directly to PARylated chromatin via PBZ domain. APLF, also known as Xipl, is a recently discovered DNA repair protein with two C-terminal PBZ domains, which are required for the recruitment of APLF to sites of DNA damage. Interestingly, APLF is known to associate with core NHEJ components such as XRCC4-DNA ligase IV and Ku proteins. It is, thus, tempting to speculate that the augmented Ku protein recruitment to chromatin by increased PARP-1 expression in human cancer cells may be via association with APLF that binds to the abundant PARylated chromatin via its PBZ domain carrying Ku.

It is noteworthy that PARP-1 has also been suggested to compete with Ku proteins in binding to the DNA ends and, thus, perhaps inhibits the classical NHEJ repair activity and may contribute to DSB repair via an alternative NHEJ. However, as clearly shown herein increased PARP-1 expression and activity up-regulates instead of inhibiting Ku protein recruitment and DNA-PK activity. Although the reason is currently unclear for the difference between these studies, the results from these studies indicate that PARP-1 may contribute to NHEJ repair of DSB via different pathways.

The finding that FASN may reduce HR repair of DSBs via up-regulating PARP-1 is interesting but consistent with previous observations. Initially, PARP-1 was thought to have a protective role against HR via binding to DNA break and preventing the HR machinery from recognizing and processing DNA lesions. Indeed, it was found later that inhibition or loss of PARP-1 increased HR activity in cells or in vivo. PARP-1 may inhibit HR activity by PARylating BRCA1 and inhibiting its activity or by inhibiting the expression of BRCA1 and BRCA2. It has also been observed that over-accumulation of PARylation also interferes with HR activity. Clearly, FASN regulates both NHEJ and HR via up-regulating PARP-1. The promotion of the NHEJ pathway over HR may be a unique solution adopted by FASN over-expressing cancer cells to achieve efficient repair of DSBs, as HR was associated with slower rate of repair compared to NHEJ. These finding suggest that inhibiting FASN in HR-deficient cells may provide a novel approach of eliminating cancer cells in combination with DNA-damaging treatments or with PARP inhibitors.

Although it has been shown that the rat PARP-1 promoter is regulated by a composite binding site for transcription factors SP1 and NF1, a similar composite binding site for SP1 and p65 in the promoter of human PARP-1 was found. While SP1 activates, p65 inhibits PARP-1 transcription by binding to the same composite site in a mutually exclusive manner. Composite elements are regulatory sequences commonly found in vertebrate gene promoters that contain two or more closely positioned binding sites for distinct transcription factors and provide a way for fine-tuning gene expression. Binding of transcription factors to composite elements can either synergistically or antagonistically regulate gene expression. Similar to our findings, NF-κB antagonizes SP1 activation of P-selectin promoter via an NF-κB/SP1 composite site.

Previously, it was determined that FASN suppresses TNF-α production, which is consistent with the current finding of reduced NF-κB expression by FASN. However, it is unknown how FASN inhibits NF-κB expression. Although the end product of FASN catalysis, palmitate, may mediate FASN regulation of SP1 expression, it does not appear to affect NF-κB. Previously, it was found that supplementation of palmitate increased drug resistance of breast cancer cells (see e.g., Liu H, Liu Y, & Zhang J T (2008). A new mechanism of drug resistance in breast cancer cells:

fatty acid synthase overexpression-mediated palmitate overproduction. MOL. CANCER THER. 7(2):263-270), which is consistent with the up-regulation of SP1, which in turn increases NHEJ. Thus, lipid metabolism may play an important role in cancer cell survival against genotoxic insults. However, it remains to be determined how palmitate regulates SP1 and how FASN regulates NF-κB.

Although different FASN inhibitors have been identified, none has successfully moved into clinical use. Using in silico screening of an FDA-approved drug database, proton pump inhibitors (PPIs) were identified as effective inhibitors of the thioesterase activity of human FASN. Further, PPIs exhibited inhibited proliferation and induced apoptosis of cancer cells. Supplementation of palmitate, the end product of FASN catalysis, rescued cancer cells from PPI-induced cell death. See Fako V. E. et al., Repositioning proton pump inhibitors as anticancer drugs by targeting the thioesterase domain of human fatty acid synthase, J. MED. CHEM. 2015 Jan. 22, 58(2): 778-84.

Figure 15:
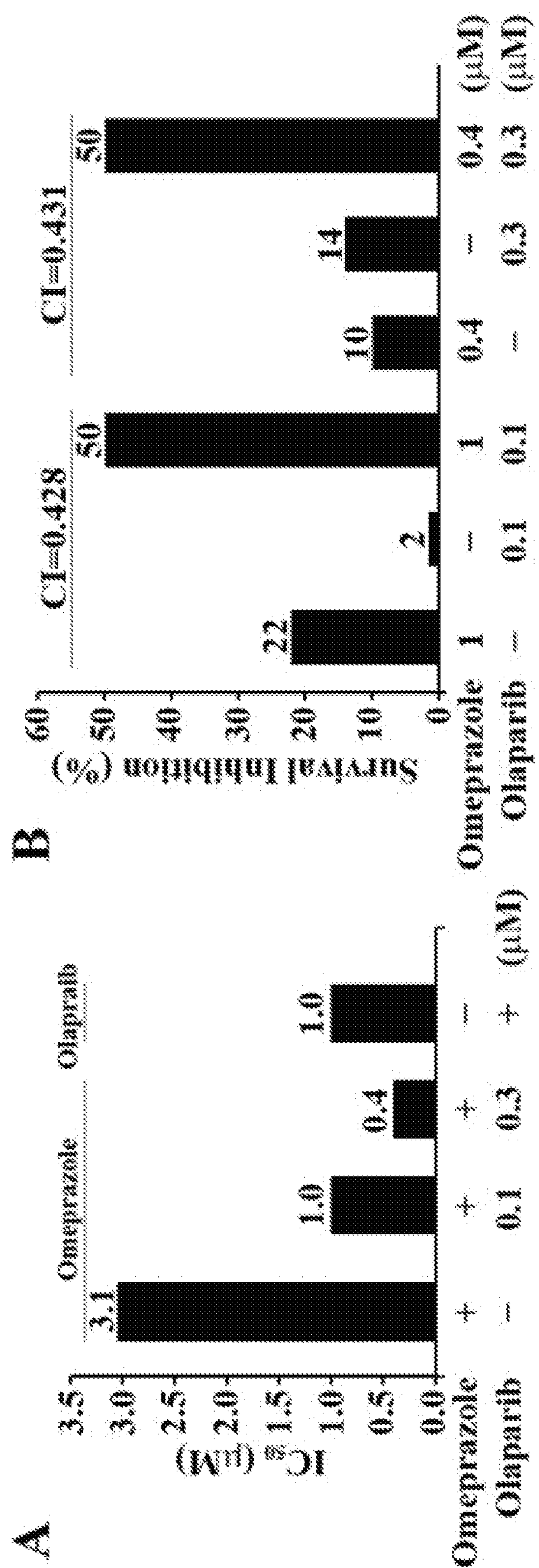
FIG. 15. Synergistic effect of proton pump inhibitor, omeprazole, and PARP-1 inhibitor, olaparib, combination on MCF-7 Cells. A. Reduction of omeprazole $IC_{50}$ by olaparib. MCF-7 cells were treated with different concentrations of omeprazole in the absence or presence of 0.1 and 0.3 μM olaparib or treated in the presence of different concentrations of olaparib alone followed by colony formation assay. The $IC_{50}$ of omeprazole in the absence or presence of olaparib and the $IC_{50}$ of olaparib alone was derived from the dose response curves. B. Combination index. Combination index (CI) was derived using the data shown in A and the formula.

The above findings suggest that inhibiting FASN by PPIs may sensitize cancer cells to PARP-1 inhibitors. To test this possibility, the combination effect on cancer cell survival was tested using omeprazole (PPI) and olaparib (PARP inhibitor). Now referring to FIG. 15A, the $IC_{50}$ of omeprazole and olaparib for MCF-7 cells are 3.1 and 1.0 μM, respectively. In the presence of 0.1 and 0.3 μM olaparib, the $IC_{50}$ of omeprazole was reduced from 3.1 μM to 1.0 and 0.4 μM, respectively. Now referring to FIG. 15B, further analysis showed that the combination of omeprazole and olaparib generated synergistic effect on inhibiting MCF-7 cell survival with the combination index (CI) of ~0.43 with two different combinations.

Because PPIs are widely used for treatment of a variety of acid-related digestive disorders, many cancer patients may use PPIs without the knowledge that the combination of PPIs with their chemotherapy may have helped them. To this end, a retrospective association analysis was conducted using de-identified electronic medical records (EMR) of 6,752 breast cancer patients from Indiana Network for Patient Care (INPC). The average age at diagnosis is 58.9 years (range 19-102) and average age at death or last visit is 61.5 (range 21-104). Of this cohort, 534 patients took one or more PPIs after diagnosis as recorded in the EMR. There are 488 triple negative breast cancer (TNBC) patients, among them 35 used PPIs. Using the Cox proportional hazard regression model, the patient overall survival was analyzed against PPI usage. Now referring to FIG. 16A, breast cancer patients who took PPIs had significantly increased overall survival than patients who did not. Now referring to FIG. 16B, analysis of the triple negative breast cancer (TNBC) patient subgroup showed that PPI usage also had significant but perhaps more protective effect. The protective effect of PPIs on patient survival was adjusted for age, tumor stage, and time of first diagnosis.

In some embodiments of this disclosure, two or more FDA-approved drugs for cancer treatments may be used together or event combined with one another the drugs used in this combined therapy may include: (1) combination of PPIs (proton pump inhibitors) that are approved for treatment of digestive disorder and PARP inhibitors that are approved for breast cancer treatments and (2) combination of PPIs with DNA-damaging anticancer drugs such as doxorubicin or cisplatin or DNA-damaging radiotherapy.

Experimental Procedures

All experiments involving human cell lines and recombinant DNAs were approved by the Institutional Biosafety Committee at Indiana University.

Construct Engineering.

A pCβA-SP1 construct was engineered for ectopic SP1 over-expression. Briefly, cDNA encoding SP1 was purchased from Open Biosystem (Lafayette, Colo.) and released from the vector, pOTB7, by double digestion with EcoR I and Xho I. The cDNA fragment was inserted into the mammalian cell expression vector, pCβA, digested with EcoR I and Xho I, resulting in pCβA-SP1, and confirmed by DNA sequencing.

Cell Lines and Transient Transfections.

Human breast cancer cell line MCF7 and pancreatic cancer cell line Panc-1 were cultured at 37° C. with 5% $CO_2$ in DMEM medium supplemented with 10% fetal bovine serum, 100 units/ml penicillin and 100 μg/ml streptomycin. FASN-overexpressing MCF7 (M/FASN) and Panc-1 (P/FASN) cells and their respective vector-transfected control clones (M/Vec, P/Vec), as well as stable MCF7/AdVp3000 cells with FASN-knockdown (M3K/Sh) and its control scrambled shRNA-transfected clone (M3K/Scr) were generated previously (see e.g., Liu H, Liu Y, & Zhang J T (2008). A new mechanism of drug resistance in breast cancer cells: fatty acid synthase overexpression-mediated palmitate overproduction. *Mol. Cancer Ther.* 7(2):263-270 and Yang Y, et al. (2011) Role of fatty acid synthase in gemcitabine and radiation resistance of pancreatic cancers. *Int. J. Biochem. Mol. Biol.* 2(1):89-98) and maintained in DMEM medium supplemented with 10% fetal bovine serum, 100 units/ml penicillin, 100 mg/ml streptomycin, and 400 μg/ml G418.

For transient transfection of pCβA-SP1, pcDNA3-p65-flag, or p65 shRNA constructs and their respective control plasmids, cells were seeded at $3\times10^5$ in 6-well plates and cultured for 24 hours before transfection with 2 μg of plasmids using METAFECTENE® pro according to manufacturer's instructions. For transient transfection of PARP-1 siRNA (Santa Cruz, sc-29437) or FASN siRNA (Santa Cruz, sc-43758), $6\times10^5$ cells were plated in 6-well plates for 24 h, followed by transfection with siRNAs using METAFECTENE® pro according to supplier's instructions. The final siRNA concentrations for PARP-1 and FASN were 50 and 100 nM, respectively. At 48 hours after transfection, the cells were collected or seeded for different assays.

Western Blot Analysis.

Western blot analysis was performed as previously described (see e.g., Liu H, Liu Y, & Zhang J T (2008). A new mechanism of drug resistance in breast cancer cells: fatty acid synthase overexpression-mediated palmitate overproduction. *Mol. Cancer Ther.* 7(2):263-270) using primary antibodies against FASN (BD Biosciences, 610962), PARP-1 (Cell Signaling, 9542), Histone-H3 (Cell Signaling, 2650), NF-κB p65 (Santa Cruz, sc372), Ku70 (Santa Cruz, sc-1487), γ-H2AX (Millipore, 05636), and Anti-PAR (Trevigen, 4335). Final images were captured using FluorChemHD2 and staining intensity was quantified using AlphaEaseFC program associated with the FluorChemHD2 imager.

MTT and Colony Formation Survival Assays.

MTT survival assay was performed as previously described (see e.g., Yang Y, Chen Q, & Zhang J T (2002) Structural and functional consequences of mutating cysteine residues in the amino terminus of human multidrug resistance-associated protein 1. *J. Biol. Chem.* 277(46):44268-44277). Briefly, cells in 96-well plate were cultured for 24 hours and treated with various concentrations of doxorubicin, bleomycin, cisplatin or $H_2O_2$ continuously for 3 days followed by addition of thiazolyl blue tetrazolium bromide (MTT) to a final concentration of 0.5 mg/mL and incubation at 37° C. for 4 hours. Medium was then removed and formazan was solubilized in dimethyl sulfoxide and the OD570 was measured by a Synergy H1 hybrid reader (BioTek, Winooski, Vt.). $IC_{50}$'s were obtained from the fitted curves generated by GraphPad Prism 5.0 program (GraphPad Software, Inc.). Relative resistance factor (RRF) is calculated using the formula $RRF=IC_{50}$ (test)/$IC_{50}$ (control) with control normalized as 1. For MCF7/AdVp3000 (M3K) derived cell lines, 10 μM fumitremorgin C (FTC) was pre-incubated for 30 minutes before addition of doxorubicin to inhibit high ABCG2 activities in these cell lines. For MTT assay following PARP-1 knockdown, MCF7/FASN cells were transiently transfected with control scramble or PARP-1 siRNA. At 24 hours after transfection, cells were re-plated in 96-well plates and treated with doxorubicin for survival analysis.

Colony formation assay was performed as previously described (see e.g., Li Z, et al. (2010) Role of 14-3-3sigma in poor prognosis and in radiation and drug resistance of human pancreatic cancers. *BMC Cancer* 10:598) for ionizing radiation (IR) and UVB treatments. Briefly, 100 cells were plated in 60-mm dishes and incubated for 24 hours followed by treatment with IR or UVB and continuous culture for 10 days before removing medium and washing cells with PBS. Colonies were fixed and stained with a solution containing 0.05% (w/v) crystal violet and 20% methanol in PBS.

Immunofluorescence Staining and Imaging.

Immunofluorescence staining and imaging were performed as previously described (see e.g., Chen Q, Yang Y, Li L, & Zhang J T (2006) The amino terminus of the human multidrug resistance transporter ABCC1 has a U-shaped folding with a gating function. *J. Biol. Chem.* 281(41): 31152-31163). Briefly, cells were cultured on coverslips in 60-mm culture dishes and treated with IR. At different times following IR treatment, cells on coverslips were washed with PBS, fixed with 50:50 (V:V) acetone/methanol at room temperature for 10 min, blocked with 1% bovine serum albumin in PBS for 30 min, and probed with anti-γ-H2AX antibody (1:100; Millipore, 05636) at room temperature for 1 hour, followed by washing and incubation with FITC-conjugated goat anti-mouse IgG at room temperature for 30 min. The cover slips were washed again and incubated with 4', 6-diamidine-2-phenylindole dihydrochloride (DAPI) (1 μg/mL in PBS) for 10 min in the dark. The coverslips were then mounted on slides before viewing with an Olympus 2 confocal microscope.

Neutral Comet Assay.

Neutral comet assay was performed using kit from Trevigen (Gaithersburg, Md.) according to the manufacturer's instructions. Briefly, cells following IR were harvested and mixed with low temperature-melting agarose as single-cell suspensions at 37° C. The resulting cell-agarose mixture was immediately layered onto Comet Slides (Trevigen). The agarose was allowed to set for 1 hour at 4° C. and the slides were then lysed at 4° C. for 30 min in the dark. After lysis, slides were subjected to electrophoresis and then immersed twice in distilled water for 10 min and once in 70% ethanol for 5 min. Slides were then dried completely at room temperature and stained with SYBR Green I (Trevigen). Comets were observed and recorded by a Zeiss Axiovert 25 fluorescent microscope equipped with a CCD camera, and analyzed with CometScore V1.5 (TriTek, Sumerduck, Va.). The Olive Tail Moment was determined by scoring 100 cells in each sample as previously described (see e.g., Olive P L, Wlodek D, & Banath J P (1991) DNA double-strand breaks measured in individual cells subjected to gel electrophoresis. *Cancer Res* 51(17):4671-4676).

Host Cell Reactivation (HCR) Assay.

The HCR assay of NHEJ activity was performed as previously described (see e.g., Boeckman H J, Trego K S, & Turchi J J (2005) Cisplatin sensitizes cancer cells to ionizing radiation via inhibition of nonhomologous end joining. *Mol Cancer Res* 3(5):277-285) with minor modifications. Briefly, $5\times10^4$ cells/well were seeded in 24-well plates, cultured overnight before transfection using Lipofectamine Plus of either 400 ng intact (control) or HindIII-linearized (test) pGL3 encoding firefly luciferase (FL) together with 20 ng pRL-TK (Promega) encoding renilla luciferase (RL) as a control for transfection efficiency. Cells were harvested at 8 hours following transfection and both FL and RL activities were determined using a Dual-Luciferase Reporter Assay System (Promega). FL activities from both control and test groups were first normalized to that of RL activities before calculating NHEJ activity using the formula NHEJ activity=(normalized FL activity in test group)×100/(normalized FL activity in control group).

The HCR assay of HR activity was performed also as previously described (see e.g., Tsai Y S, Huang J L, & Lin C S (2011) Application of Host Cell Reactivation in Evaluating the Effects of Anticancer Drugs and Environmental Toxicants on Cellular DNA Repair Activity in Head and Neck Cancer. *Selected Topics in DNA Repair*, (InTech), pp 465-482) with modifications. Briefly, the pGL3 plasmid was digested with NcoI and XcmI to generate a fragment containing the SV40 promoter and the 5'-portion of the FL gene as well as with BsrGI and BamH I to generate another fragment containing the 3'-portion of the FL gene and the poly-A signal. These two DNA fragments, containing a 245-bp overlapping region, were purified and co-transfected along with the pRL-TK control plasmid into $7\times10^4$ cells/well in a 24-well plate using Metafectene Pro transfection reagent (Biontex). The NcoI-XcmI and BsrGI-BamHI fragment alone transfection was used as negative controls. At 24 hours after transfection, cells were harvested for Dual-Luciferase Reporter Assay as described above. FL activities were first normalized to RL activities for transfection efficiency before deriving relative HR activity using the formula HR activity (fold)=(Normalized FL activity in P/FASN or M3K/Sh cells)/(Normalized FL activity in P/Vec or M3K/Scr cells)

DNA-Pk Activity.

DNA-PK activity was analyzed using SignaTECT DNA-dependent Protein Kinase Assay System (Promega, Madison, Wis.) according to manufacturer's instructions. Briefly, 10 μg nuclear extract with endogenous DNA removed by DEAE-Sepharose filtration was incubated with biotinylated peptide substrate, [γ-32P]ATP, and either DNA-PK activation buffer or DNA-PK control buffer for 5 minutes at 30° C. Termination buffer was added, and 10 μL of each reaction sample were spotted onto a SAM2™ biotin capture membrane. The SAM2™ membrane were then washed and dried before analysis by scintillation counting. DNA-PK activity is expressed as specific activity in pmol ATP/minute/μg of protein.

Real-Time Quantitative PCR Analysis.

Real-time quantitative PCR analysis was performed as previously described. Briefly, cells were harvested, and total RNA was extracted using RNeasy Mini Kit (Qiagen, Valencia, Calif.) followed by real-time RT-PCR using the Power SYBR Green RNA-to-CT 1-Step kit (Applied Biosystems, Carlsbad, Calif.). Data were normalized to an internal control gene, glyceraldehyde-3-phosphate dehydrogenase (GAPDH). Primer pairs used were 5'-CCCAGGGTCTTCG-GATAG-3' (forward) (SEQ ID NO:1) and 5'-AGCGTGCTTCAGTTCATACA-3' (reverse) (SEQ ID NO:2) for PARP-1. Amplification of a single PCR product was confirmed by melt-curve analysis.

NF-κB Activity Assay.

For NF-κB activity assay, P/FASN, M3K/Sh and their control P/Vec and M3K/Scr cells were seeded at $5\times10^4$ cells/well in 24-well plates and transfected with a PathDetect NF-κB Cis-Reporting plasmid (Agilent Technologies, Santa Clara, Calif.). pRL-TK encoding renilla luciferase was co-transfected as a control for transfection efficiency. At 48 hours after transfection, cells were harvested for luciferase assay using the Dual-Luciferase Reporter Assay System as described above.

Cell Cycle Analyses.

Cells seeded in 100-mm dishes at $6\times10^5$ cells/dish were cultured for three days before treatments and cell cycle analysis. For serum starvation, the cells were washed with serum-free media and cultured in the same media for 48 hours before fixation in 70% ethanol at room temperature for 30 minutes. For thymidine block, the cells were treated with 2 mM thymidine for 28 hours followed by thymidine removal and culture for 10 hours in complete media without thymidine. The cells were treated again with 2 mM thymidine for 24 hours followed by fixation with ethanol as described above. For nocodazole treatment, cells were cultured in media containing 100 ng/ml nocodazole for 18 hours and followed by fixation with ethanol as described above. The fixed cells were then washed with PBS, stained with 50 μg/ml propidium iodide, and digested with 100 μg/ml RNase at 37° C. for 30 min before analysis using a FAC Scan flow cytometer. Cell cycle distribution was analyzed with the Modfit LT program.

Chromatin Immunoprecipitation (ChIP).

ChIP was performed as previously described using a Millipore ChIP assay kit. Briefly, Panc-1 cells were seeded at $1\times10^6$ in 100 mm dishes and cultured for 24 hours before transfection with Flag-p65 cDNA or vector control. At 48 hours post transfection, cells were fixed with 1% formaldehyde and subjected to ChIP analyses. Primers for PARP-1 promoter were 5'-CCGGGTCCTCCAAAGAGCTA-3' (forward) (SEQ ID NO:3) and 5'-GCCGTTCCCTGATAGAT-TGCT-3' (reverse) (SEQ ID NO:4). Data were analyzed as percentage of input of total samples and calculated as previously described. See Zampieri M, et al. (2009), *Parp1 localizes within the Dnmt1 promoter and protects its unmethylated state by its enzymatic activity*. PLOS ONE 4(3): e4717.

Statistical Analysis.

Student's t-test was used for all statistical analysis with $p<0.05$ considered significant. All experiments were performed independently at least 3 times for statistical analysis.

In this study, proton pump inhibitors (PPIs), approved for treating digestive disorders, effectively inhibits FASN in and suppress survival of human breast cancer cells. PPIs also help overcome doxorubicin and radiation resistance in these cells by suppressing DNA damage repair via inhibiting FASN activity and PARP1 expression. Furthermore, retrospective analyses of a database containing 6,752 breast cancer patients showed that PPI usage dramatically increased overall survival and reduced disease recurrence of these patients. Both Caucasian and African American patients benefited from PPI usage. Also, the R-enantiomer performed better than the S-enantiomer of PPIs both clinically and in in-vitro assays. Thus, PPIs may be repurposed as drugs to treat breast cancers and diabetes by inhibiting FASN.

Fatty acid synthase (FASN) is a protein with multiple domains of different enzymatic activities and it is the sole mammalian enzyme in cytosol responsible for de-novo synthesis of fatty acids, primarily palmitate. Because western diet provides sufficient fatty acids, most of our normal tissues except lipogenic ones do not need de-novo synthesis of lipids and, thus, FASN expression is extremely low in these tissues. However, high level of FASN expression has been observed in multiple cancers including breast cancer and it was thought that cancer cells rely on de-novo synthesis of fatty acids to survive. It has also been observed that FASN expression associates with poor prognosis of many cancers including breast cancer and contributes to drug and radiation resistance possibly by regulating DNA damage repair. In addition, FASN over-expression has also been found to relate to non-alcoholic fatty liver disease and insulin-resistant diabetes. Thus, FASN may be a good target for discovery of drugs to treat various human diseases including cancer.

Indeed, targeting FASN is gaining traction and there have been various efforts toward discovery of novel drugs targeting FASN. However, no such drugs targeting FASN have been approved with few currently in clinical trials. Proton pump inhibitors (PPIs), approved for treating digestive disorders, can also effectively inhibit FASN by inhibiting the thioesterase (TE) activity of FASN and induced apoptosis of pancreatic ductal adenocarcinoma cells (Fako et al., 2015). Thus, it is possible that the PPIs may be repositioned as therapeutics targeting FASN for cancer treatment.

In this study, the above hypothesis in breast cancers were examined using cell-based and retrospective analysis of an electronic medical record (EMR) database containing a cohort of 6,752 breast cancer patients. PPIs effectively inhibited FASN in and suppressed proliferation and survival of breast cancer cells. PPIs also added synergism to treatment with DNA-damaging drug doxorubicin and ionizing radiation, consistent with the function of FASN in regulating NHEJ repair of double strand DNA breaks. Retrospective analyses of the EMR revealed that PPI usage dramatically increased overall survival and reduced disease recurrence of breast cancer patients. Both Caucasian and African American patients benefited from PPI usage. It was also found that the R-enantiomer performed better than the S-enantiomer of PPIs both clinically and in in-vitro assays. Thus, PPIs may be repurposed as drugs to treat breast cancers and diabetes by inhibiting FASN. These findings may also help physician make decisions in choosing correct PPIs for future treatment of breast cancers and perhaps other diseases such as insulin-resistant diabetes.

PPIs Inhibit FASN and Suppress Survival of Breast Cancer Cells.

PPIs can inhibit FASN activity in and suppressed proliferation and induced apoptosis of pancreatic cancer cells (Fako et al., 2015). To determine if PPIs also inhibit FASN in breast cancer cells, FASN activity assay was performed using lysate isolated from human breast cancer MCF7 cells. Referring now to FIG. 17A and FIG. 25, all four PPIs (lansoprazole, omeprazole, pantoprazole, and rabeprazole) dose-dependently inhibited FASN with $IC_{50}$ ranging from 6.7±0.9 to 18.4±1.7 μM.

Next, tested whether PPIs inhibit survival of breast cancer cell lines with different levels of FASN expression (FIG. 17B) using colony formation assay. Referring now FIG. 17C and FIG. 26, all PPIs dose-dependently inhibited survival of four breast cancer cell lines with $IC_{50}$ ranging from 1.3±0.7 to 49.4±9.5 μM with lansoprazole as the most effective one for all 4 cell lines.

FASN Mediates PPI Effects on Breast Cancer Cell Survival.

To determine if PPIs inhibit breast cancer cell survival possibly via inhibiting FASN, correlation analysis was performed between the FASN protein level of the four breast cancer cell lines and the $IC_{50}$ of four PPIs. Referring now to FIG. 17D, while the $IC_{50}$ of lansoprazole, omeprazole, and pantoprazole negatively associates with FASN level (correlation coefficient $R^2$=0.96-0.99), the association between $IC_{50}$ of rabeprazole and FASN level is less strong (correlation coefficient $R^2$=0.32). These findings suggest that the expression level of endogenous FASN may contribute to the sensitivity of breast cancer cells to PPIs and that PPIs may suppress breast cancer cell survival via inhibiting FASN.

To further determine the role of FASN in PPI inhibition of breast cancer cell survival and if PPIs act on FASN in breast cancer cells, stable MCF7 cells were used with ectopic FASN over-expression (MCF7/FASN) and MCF7/AdVp3000 cells with FASN knockdown (M3K/Sh) (FIG. 18A) and treated them with lansoprazole followed by determining survival using colony formation assay. Referring now to FIG. 18B, FASN over-expression and knockdown increased and reduced lansoprazole resistance, respectively, indicating that FASN expression affects lansoprazole sensitivity and, thus, a likely target of lansoprazole.

Next, all 4 breast cancer cell lines were treated with lansoprazole and determined the expression of PARP1, a known FASN downstream target gene (FIG. 18A, see also Wu et al., FASN regulates cellular response to genotoxic treatments by increasing PARP-1 expression and DNA repair activity via NF-kappaB and SP1. (2017) Proc Nail Acas Sci USA), using Western blot analysis. Referring now to FIG. 18C, lansoprazole dose-dependently reduced PARP1 expression in all 4 cell lines. FASN can regulate NHEJ repair activity by regulating PARP1 expression (Wu et al., 2017). Thus, using reporter assay whether lansoprazole inhibits NHEJ activity in breast cancer cells was examined. Referring now to FIG. 18D, lansoprazole significantly reduced the NHEJ activity in both MCF7 and MDA-MB-468 cells. Furthermore, over-expressing ectopic FASN was also able to overcome lansoprazole suppression of and rescue NHEJ activity in MCF7 cells (FIG. 18E).

To determine if lansoprazole treatment causes damages to chromatin DNA by inhibiting NHEJ repair, the level of γ-H2AX, an indicator of DNA damages, in MCF7 and MDA-MB-468 cells were determined following lansoprazole treatment. Referring now to FIG. 18F, lansoprazole treatment increased the level of γ-H2AX in a dose-dependent manner in both cell lines. Furthermore, the lansoprazole-induced γ-H2AX increase in MCF7 cells was ablated by over-expressing ectopic FASN (FIG. 18G). Together, the above findings suggest that lansoprazole likely inhibits breast cancer cell survival by inhibiting FASN and DNA repair, leading to increased DNA damages.

It has been shown that FASN can regulate cell cycle progression and cell survival. To further confirm that FASN mediates lansoprazole effect on breast cancer cells, the effect of lansoprazole on cell cycle and apoptosis were determined. Referring now to FIG. 26A, lansoprazole dose-dependently induced apoptosis in both MCF7 and MDA-MB-468 cells. Lansoprazole also dose-dependently caused cell cycle arrest at G1 in MCF7 and S phase in MDA-MB-468 cells (FIG. 27B).

Lansoprazole and DNA-Damaging Treatments Synergistically Inhibit Breast Cancer Cell Survival.

Based on our findings that FASN regulates NHEJ repair (Wu et al., 2017) and lansoprazole inhibits NHEJ possibly via inhibiting FASN (FIG. 18), PPI might have synergistic effect with DNA-damaging treatments on breast cancer cells. For this purpose, the effect of lansoprazole were examined on DNA damages induced by doxorubicin, an FDA-approved breast cancer drug that causes double strand DNA breaks. Referring now to FIG. 19A and FIG. 19B, lansoprazole and doxorubicin synergistically increased γ-H2AX level in both MCF7 and MDA-MB-468 cells.

To determine if the increased endogenous DNA damages by lansoprazole treatment is due to suppression of DNA repair, ionizing radiation (IR) treatment, which allows monitoring DNA repair at different times following radiation was performed. For this purpose, MCF7 and MDA-MB-468 cells were first pre-treated with lansoprazole followed by 5 Gy IR treatment. Cells were collected at 1 or 4 hrs following IR to determine the level of γ-H2AX as an indicator of remaining DNA damage levels. Referring now to FIG. 19B, without IR, lansoprazole pre-treatment increased γ-H2AX compared with control untreated cells. At 1 hr following IR treatment, dramatic increases in γ-H2AX level were observed in all cells. Interestingly, little γ-H2AX remained at 4 hrs post-IR in control cells without lansoprazole pre-treatment compared with the cells pre-treated by lansoprazole. These findings suggest that the majority of DNA damages induced by IR have been repaired at 4 hrs after IR in the control cells while the repair may have been inhibited in cells pre-treated with lansoprazole.

The above findings suggest that PPIs may have synergistic effect with DNA-damaging treatments on breast cancer cells. To test this possibility, colony formation assay were performed using different $IC_{50}$ combinations of lansoprazole and doxorubicin. Referring now to FIG. 19C and FIG. 28, lansoprazole and doxorubicin with combinations at different $IC_{50}$ ratios all synergistically inhibited both MCF7 and MDA-MB-468 cell with combination index <1.0. Similarly, lansoprazole sensitized MCF7 and MDA-MB-468 cells to IR treatment (FIG. 19D). These findings not only suggest that lansoprazole adds synergism to both chemo and radiation therapy but also confirms that FASN is the likely target of lansoprazole in breast cancer cells.

PP1 Usage Improves Overall Survival of Breast Cancer Patients.

Because PPIs are approved to treat digestive disorders, PPI usage may benefit breast cancer patients. To test this hypothesis, a retrospective analysis of a breast cancer patient database was performed with medication history (see Table 1 for patient characteristics). Analysis of the overall survival of this cohort showed that the PPI-users had significantly better overall survival than the non-PPI-users with a HR of 0.37 and a p-value <10' (FIG. 20A). Further analysis of the TNBC subgroup in this cohort also showed significant benefits of PPI usage with a HR of 0.49 and a p-value<0.01 (FIG. 20B). Thus, PPI usage may benefit breast cancer patients including the TNBC subgroup.

Differential Effects of R- and S-Enantiomers of PPIs.

Next, determined if different PPIs may have different levels of benefits for breast cancer patients by analyzing the data of patients who took only one of the FDA-approved PPIs. Patients who took more than one PPI were excluded from this analysis. Referring now to FIG. 20C, only 5 of 6 FDA-approved PPIs (lansoprazole, omeprazole, pantoprazole, rabeprazole, and esomeprazole) were used by this cohort with the majority of PPI users taking esomeprazole and omeprazole. FIG. 20D and Table 2 show that while the use of lansoprazole, omeprazole, and pantoprazole similarly increased overall survival, the use of esomeprazole had significantly less effect on the overall survival than omeprazole and lansoprazole. This finding suggests that the S-enantiomer of PPIs may be less effective than the racemic PPI, which also contains the R-enantiomer. Interestingly, rabeprazole usage did not appear to significantly benefit the overall survival.

To determine if different enantiomers of PPIs possibly have different activity in inhibiting FASN, and thus, resulting in different clinical outcomes, FASN TE activity assay was performed in the presence of R and S enantiomers of omeprazole as previously described (Fako et al., 2015). Referring now to FIG. 20E, the R-omeprazole is significantly more effective than the S-omeprazole in inhibiting TE with lower Ki. Similarly, the R-lansoprazole is also significantly more effective than the S-lansoprazole (FIG. 20E). Thus, the R-enantiomers of PPIs are likely more effective than the S-enantiomers in inhibiting FASN, which may lead to better clinical outcomes.

Association of PPI Usage with Overall Survival of Patients Using Chemo or Hormonal Therapies.

Because PPIs were likely used to treat digestive diseases other than the cancer of patients in our cohort, it is possible that PPI usage may synergize the effect of cancer therapeutics such as the DNA-damage drugs as observed above using cell-based assays. To test this possibility and to determine which cancer therapeutics have synergistic effects with PPIs clinically, patients from this cohort who were treated with chemo or hormonal therapies were first selected, followed by survival analysis of PPI usage. Referring now to FIG. 21A and FIG. 21B, PPI usage significantly increased the overall survival of patients who received chemo or hormonal therapies. Interestingly, detailed analysis of different chemo or hormonal therapies showed that patients who received anti-metabolite chemotherapy or GnRH hormonal therapy may not benefit significantly from PPI usage while all others including DNA-damaging drugs had significant benefits (Table 3). Although there are significant benefits from PPI use for patients who were treated by aromatase or HER2 inhibitors, the benefit of using PPIs in combination with HER2 or aromatase inhibitors tends to be less than that in combination with DNA-damaging drugs (FIG. 29).

Association of PPI Usage with Overall Survival of Patients in Different Ethnicity.

Next, determined if ethnicity potentially affect benefits of PPI usage. In our cohort, the vast majority of patients are either African (AA) or Caucasian (CA) Americans and there are only 117 patients with other diverse ethnic backgrounds including Hispanics, Pacific Islanders, Native Americans, South or East Asians. The sample size of the latter populations in different ethnicity is too small for any meaningful analysis. Thus, only CA and AA populations were included for this analysis. Referring now to FIG. 21C, the overall survival of CA patients is significantly better than AA patients with a HR ratio of 0.73 and a p-value of $3.05\times10^{-7}$, consistent with the knowledge of survival disparity among AA patients. Further analyses showed that PPI usage increased the overall survival in both AA and CA populations (FIG. 21D). Thus, both AA and CA patients benefited from PPI usage. It is also noteworthy that ~29% of AA patients took PPIs while only ~12% of CA patients took PPIs and that the overall survival of AA patients who took PPIs is significantly better than CA patients who did not take PPIs with a HR of 0.6061 and a p value of $9.4\times10^{-5}$ (FIG. 21D). Finally, analyses of the individual PPI usage in CA and AA patient populations showed that lansoprazole may perform better than other PPIs for AA patients while there is no difference between lansoprazole, omeprazole, and pantoprazole for CA patients (FIG. 21E, FIG. 21F and Table 4).

Association of PPI Usage with Breast Cancer Recurrence.

Finally, the potential effect of PPI usage on recurrence retrospectively was analyzed. Of this cohort, 275 breast cancer patients developed recurrent disease as recorded in the EMR. Of these patients with recurrent disease, 18 patients took PPIs. However, only 5 of these patients took PPIs before their disease recurrence and, thus, the recurrence rate is 0.6% (5 out of 876) for PPI users. Because the remaining 15 patients took PPIs after their disease recurrence, they were considered non-PPI users for our analysis of recurrence rate, resulting in 4.6% (270 out of 5876) for the non-PPI users (FIG. 22 inset). Furthermore, the overall survival of the PPI users with recurrent disease including the 15 patients who took PPIs after their disease recurrence is also significantly better than that of the non-PPI users (FIG. 22).

Lansoprazole and PARP Inhibitor Synergistically Inhibit Breast Cancer Cell Survival.

Because FASN up-regulates PARP1 expression and PPIs inhibit PAPR1 expression possibly via FASN, PPI might also have synergism with PARP inhibitors in suppressing breast cancer cell survival. For this purpose, whether over-expressing or down-regulating FASN affects cellular sensitivity to PARP inhibitor, olaparib, was examined. Referring now to FIG. 23A, MCF7 cells with FASN over-expression were significantly more resistant to olaparib than the control MCF7 cells harboring vector and M3K cells with FASN knockdown were significantly more sensitive to olaparib than the control cells harboring scrambled shRNA control. Next, the combination effect of lansoprazole with olaparib on breast cancer cell survival was tested. Referring now to FIG. 23B and FIG. 23D, lansoprazole and olaparib synergistically suppressed the survival of both MCF7 and MDA-MB-468 cells. Thus, PPIs may sensitize breast cancer cells to PARP inhibitors, a possible approach as treatment for breast cancers.

Effect of Lansoprazole Metabolites on Breast Cancer Cell Survival.

PPIs except rabeprazol are metabolized mainly by cytochrome P450 CYP2C19 and CYP3A4 (16). It is currently unknown if PPI metabolism affects PPI activity in anticancer activity and breast cancer cell survival. For this purpose, the five known metabolites of lansoprazole were tested against breast cancer cells in comparison with the parent lansoprazole. Referring now to FIG. 24A, while 5-hydroxy lansoprazole, lansoprazole sulfide, and lansoprazole sulfone lost their activity in suppressing breast cancer cell survival, 5-hydroxy lansoprazole sulfide is significantly more effective than lansoprazole in suppressing the survival of triple negative breast cancer cell survival (see also FIG. 24B). These findings suggest that the metabolite of lansoprazole, 5-hydroxy lansoprazole sulfide, is perhaps more effective than the parent lansoprazole in inhibiting triple negative breast cancer cells. 5-hydroxy lansoprazole sulfide also inhibited PARP1 expression and induced production of γ-H2AX in a dose-dependent manner (FIG. 24C), suggesting that 5-hydroxy lansoprazole sulfide may inhibit breast cancer cells by inhibiting FASN, similar as lansoprazole (see FIG. 18 and FIG. 19). It also appears that 5-hydroxy lansoprazole sulfide elicits more effect on PARP1 and γ-H2AX compared with lansoprazole (FIG. 24C), consistent with its lower $IC_{50}$ in inhibiting breast cancer cell survival.

Effect of Non-FDA-Approved PPIs.

In addition to the FDA-approved PPIs including lansoprazole, omeprazole, pantoprazole, rabeprazole, and enantiomers including esomeprazole and dexlansoprazole, several other PPIs such as tenatoprazole have also been tested clinically for treating digestive disorders. However, some of these PPIs were abandoned because they did not perform better than the existing PPIs. Nevertheless, these PPIs may perform better in inhibiting breast cancer cells for repurposing. To this end, three additional PPIs including anaprazole, tenatoprazole, and ilaprazole were tested against different breast cancer cell lines in comparison with lansoprazole. Referring now to FIG. 24D, while anaprazole and tenatoprazole performed better than lansoprazole only against some cell lines, ilaprazole had similar if not worse performance than lansoprazole. Together, the other PPIs that have not yet been approved for clinical use may also be repurposed as therapeutics for treating breast cancers.

FASN, as a potential target, are gaining traction in discovery of targeted therapeutics. Although currently there are no FDA-approved drugs targeting FASN, two drugs are currently being tested in clinical trials. Identification of PPIs as effective inhibitors of FASN provides a novel approach that can translate into human testing quickly for repurposing FDA-approved drugs. Findings disclosed herein that PPI usage significantly increases overall survival of breast cancer patients and reduces recurrent disease in a retrospective study show that PPIs, approved for treatment of digestive disorders, can be repurposed as breast cancer drugs.

Of the 4 PPIs tested in vitro, lansoprazole appears to be the best and is consistently more potent with $IC_{50}$'s of 1.3±0.7 μM for MCF7 cells to 21.4±4.1 μM for MDA-MB-231 cells. Its best potency in suppressing breast cancer cells is also consistent with its leading potency in inhibiting FASN activity.

The highest potency of lansoprazole is also reflected in the retrospective analysis of EMR of breast cancer patients. Although no significant difference in benefiting overall survival was observed between lansoprazole and omeprazole or pantoprazole, the HR for patients using omeprazole and pantoprazole is higher than patients using lansoprazole. This difference is more pronounced among AA patients with statistically significant difference observed. Thus, lansoprazole may perform better than omeprazole and pantoprazole clinically to benefit breast cancer patients particularly for AA patients.

Findings disclosed herein on rabeprazole are unexpected. While it is equally potent in inhibiting FASN activity as lansoprazole, it is much less potent than lansoprazole in inhibiting breast cancer cells. Furthermore, unlike that of other PPIs, the $IC_{50's}$ of rabeprazole against breast cancer cells weakly associate with FASN level in these cells. Furthermore, whether rabeprazole usage significantly impact on the overall survival of breast cancer patients in our cohort was not conclusive due to small sample size. The cause for the discrepancy of rabeprazole between inhibiting FASN activity and in suppressing breast cancer cell survival is currently unknown. The metabolism of rabeprazole can be non-enzyme-dependent, different from that of other PPIs (Hagymasi, K., et al. (2011), *Update on the pharmacogenomics of proton pump inhibitors*, PHARMACOGENOMICS 12, 873-888). While rabeprazole may directly inhibit FASN in cell lysate, rabeprzole may have been metabolized in non-enzyme-dependent manner, leading to inactivation of rabeprazole in the cell-based assays. It is also possible that the different metabolites of other PPIs are more potent FASN inhibitors and add benefit in both cell-based and clinical studies. The metabolites of rabeprazole, different from that of other PPIs, may lack such activity. These possibilities warrant further investigation in future studies.

FASN expression can contribute to drug and radiation resistance by up-regulating NHEJ repair via increasing PARP1 expression (Wu et al., 2017). It has also been reported that FASN expression causes resistance to taxane and herceptin. The findings disclosed herein that PPI usage significantly benefited patients who were treated by DNA-damaging, anti-mitotic, and HER2 inhibitors and that PPIs has synergistic effect on breast cancer cell lines with DNA-damaging treatment are consistent with the role of FASN in drug resistance and PPI inhibition of FASN. In particular, lansoprazole treatment reduced PARP1 expression and NHEJ activity and resulted in increased DNA damages in breast cancer cells, which can be rescued by over-expressing FASN, further confirming that PPIs may act via inhibiting FASN. Together with the observation that the PPI activities in inhibiting breast cancer cells correlate with cellular FASN level, PPIs may inhibit breast cancer cells via inhibiting FASN.

Artificially increasing FASN level can decrease the potency of lansoprazole, which suggests that PPI may inhibit breast cancer cells by acting on FASN. However, this observation appears to contradict with the finding disclosed herein that the potency of lansoprazole negatively associates with the endogenous FASN level in breast cancer cells. It is possible that the cancer cells with high endogenous FASN level may require and be addicted to the high level of FASN for survival, and thus, are more sensitive to PPI than the cells with less FASN. Expressing the ectopic FASN and producing extra FASN in these cells, on the other hand, generated more target proteins as sink for PPI but not required for cell survival. Thus, cells with high levels of ectopic FASN are more resistant to PPIs. The drug resistant MCF7/AdVp3000 cells can express extra endogenous FASN required for drug resistance but not for survival as demonstrated stable knockdown clones were successfully established. The FASN knockdown cells can become more sensitive to PPIs.

Finding disclosed herein that the R-enantiomers may be more effective than the S-enantiomers of PPIs in inhibiting FASN may explain why the racemic omeprazole is more effective than esomeprazole in benefiting breast cancer patients. Thus, it is possible that the use of R-enantiomers of PPIs may generate best clinical outcome for breast cancer patients. Unfortunately, no patients in our cohort had used dexlansoprazole, the only FDA-approve R-enantiomer of PPIs, as a single PPI, which prevented us from analyzing its potential clinical benefits.

While this study aims to develop and repurpose PPIs as breast cancer drugs, the fact that these PPIs inhibit FASN indicates that the PPIs may also be repurposed for other diseases that are associated with FASN over-expression. For example, it has recently been shown that increased FASN expression in adipose tissues are linked to obesity, type 2 diabetes, and insulin resistance (Menendez, J. A., et al. (2009), *Fatty acid synthase: association with insulin resistance, type 2 diabetes, and cancer*, CLIN CHEM 55, 425-438) and that chronic use of a FASN inhibitor, platensimycin, led to improved insulin sensitivity in db/+ mice fed with high-fructose diet and reduced ambient glucose levels in db/db mice (Wu, M., et al. (2011), *Antidiabetic and antisteatotic effects of the selective fatty acid synthase (FAS) inhibitor platensimycin in mouse models of diabetes*, PROC NATL ACAD SCI USA 108, 5378-5383). It has also been shown that increased FASN expression for increased de novo lipid synthesis in hepatocytes may contribute to non-alcoholic fatty liver disease or steatosis. Considering that PPIs are safe and have been approved as over the counter drugs, PPI may be used to benefit patients with diabetes or steatosis in addition to cancer patients.

Experimental Procedures

Cell Lines and Electronic Medical Records.

Human breast cancer cell lines MCF7, MDA-MB-231, MDA-MB-468, and T47D were from ATCC and authenticated using short tandem repeat on Aug. 3, 2016. These cells were cultured at 37° C. with 5% CO2 in DMEM medium supplemented with 10% fetal bovine serum, 100 units/ml penicillin and 100 μg/ml streptomycin. The stable FASN-overexpressing MCF7 (M/FASN) and MCF7/AdVp3000 cells with FASN-knockdown (M3K/Sh) and their control scrambled shRNA-transfected clone (M3K/Scr) were generated previously (Wu et al., 2017) and maintained in DMEM medium supplemented with 10% fetal bovine serum, 100 units/ml penicillin, 100 mg/ml streptomycin, and 400 μg/ml G418.

The patient database contains three domains of electronic medical records (EMR) of 6,752 de-identified breast cancer patients from Indiana Network for Patient Care (INPC). The first domain contains patient characteristics as shown in Supplemental Table 51. The second domain contains medical test results including body weight, blood tests, and office visit information. The third domain contains prescription information for each patient. The use of this database has been approved by IRB at Indiana University for this study.

FASN and TE Activity Assays.

FASN activity assay was performed as previously described (Liu, H., et al. (2008), *A new mechanism of drug resistance in breast cancer cells: fatty acid synthase overexpression-mediated palmitate overproduction*, Mol Cancer Ther 7, 263-270; Liu, H., et al. (2013), *Fatty acid synthase causes drug resistance by inhibiting TNF-alpha and ceramide production*, J Lipid Res 54, 776-785). Briefly, MCF7 cells were harvested and washed with and lysed in ice-cold PBS containing 1 mM DTT, 1 mM EDTA, and 0.05% Brij35 with intermittent sonication. The lysate were cleared of debris by centrifugation at 12,000 g for 20 min. 250 μg of lysate protein was incubated with PPIs in 200 mM $K_2HPO_4$ pH6.8, 1 mM DTT, 1 mM $MgCl_2$, 240 μM NADPH, 30 μM acetyl-CoA for 10 min at 37° C. followed by addition of 50 μM malonyl-CoA and measurement of $OD_{340\ nm}$ every minute for 20 min.

TE activity assay was performed also as previously described using recombinant TE (Fako et al., 2015). Briefly, purified recombinant TE (500 nM) was pre-incubated with PPIs at different concentrations in buffer A (100 mM Tris-HCl, 50 mM NaCl, 0.05% Brij35, pH 7.5) in opaque black, flat-bottom 96-well plates at 37° C. for 30 min followed by addition of 300 μM 4-MUH, incubation at 37° C. for 1 h, and measurement of fluorescence at 355/460 nm.

Colony Formation Assay.

Colony formation assay was performed as previously described (Fako et al., 2015). Briefly, breast cancer cells were seeded in six-well plates at 200 cells/well and cultured overnight followed by treatments without or with PPIs at different concentrations for 14 days. The colonies formed were then washed with PBS, fixed in 100% methanol and stained with 0.5% crystal violet in 25% methanol. The stained colonies were counted manually and concentration-response curves with $IC_{50}$ were generated using Prism 7.0 (GraphPad, La Jolla, USA).

For combination studies, colony formation assays were performed in the presence of different concentrations of lansoprazole and doxorubicin with three different potency ratios (lansoprazole/doxorubicin: 50/50, 25/75 and 75/25). For each potency ratio, combination index of three effective concentrations at $IC_{30}$, $IC_{50}$, and $IC_{70}$ were calculated for synergistic effects using Prism 7.0.

For the combination with ionizing radiation (IR), $1\times10^6$ breast cancer cells were seeded in 100-mm culture dish and pre-treated without or with 10 μM Lansoprazole for 3 days. Cells were then harvested and re-plated in 6-well plates at a density of 200 cells/well followed by IR treatment at different doses and colony formation assay or collection of cells for Western blot analysis. Concentration-response curves and $IC_{50}$ values were calculated using Prism 7.0 (GraphPad, La Jolla, USA).

Cell Lysate Preparation and Western Blot Analysis.

Cells were harvest and then lysed in TNN buffer with 1 mM DTT, 1 mM PMSF and 0.1% SDS for 30 min at 4° C. with occasional agitation. The cells were sonicated briefly and total proteins were harvested after centrifugation of the lysate at 16,000 g for 15 minutes at to remove cell debris. The protein concentration of cell lysates was determined using a Bio-Rad protein assay kit. Total cell lysates were then separated by SDS-PAGE, transferred to a polyvinylidene fluoride membrane, and probed using antibodies against fatty acid synthase (610963, BD biosciences), PARP-1 (46D11, CST), γ-H2AX (05-636, Millipore), and (3-Actin (A2228, Sigma). The blot was then probed with horseradish peroxidase-conjugated secondary antibodies (Sigma) and signals were captured on X-ray films following developing with Amersham ECL Western Blotting Detection Reagent (RPN2106, GE).

Host Cell Reactivation NHEJ Assay.

The host cell reactivation NHEJ assay was carried out as previously described (Wu et al., 2017) with minor modifications. Briefly, $1\times10^4$ cells were seeded in 24-well plates, cultured overnight and then treated with 10 μM Lansoprzole or vehicle every day for three days before transfection with either linearized or intact pGL3-luc firefly luciferase plasmids (400 ng) using Lipofectamine 2000 (Invitrogen). pGL3-luc plasmid was linearized by HindIII digestion, and linearization was verified by DNA agarose gel electrophoresis before transfection. pRL-TK (Promega) plasmid which encodes *renilla* luciferase was co-transfected (400 ng) as a control for transfection efficiency. 8 hours after transfection, cells were harvested and assayed for luciferase activity with Dual Luciferase Assay (Promega) on a luminometer. Firefly luciferase signal were normalized to *renilla* luciferase signal in each group. Overall NHEJ activity was calculated by firefly luciferase activity from cells transfected with linearized plasmid relative to that of the intact plasmid.

Flow Cytometry Assay.

Cancer cells were plated in 6-well plates at a density of $2\times10^5$ cells/well, cultured overnight. Followed by 3-day treatment with 10 μM Lansoprazole or vehicle. Cells were washed with PBS and fixed ice cold 70% ethanol overnight. After centrifugation, pellets were resuspended in PBS, stained with propidium iodide solution for 30 min in the dark and analyzed by flow cytometry.

Electronic Data Preprocessing.

The first task is to remove null and duplicated values and to resolve contradicting records. For patients that have contradicting records, different rules for different conflicts were followed. For conflicts on the first visit or diagnosis time, the earlier record at younger age were used as the first diagnosis and considered the later one as system update. For all other information including diagnosis information such as cancer subtype, the latest record was used as it is thought to be more accurate.

Next, the plain text information from the first domain of the database including but not limited to ER, PR, and HER2 test results, treatment plans, and therapy types were digitized. The record that is not clear was marked as unknown. For example, the HER2 status with a 2+ score, a borderline score, from IHC staining was usually confirmed with FISH test. Patients with a 2+ score but without a FISH test result were considered unknown in this study.

Further, the days of patient survival from data in the first domain were validated using prescription history of the same patient in the third domain of the database. When there is a conflict, the last day of office visit or prescription refill, whichever is later, was recorded as the last day of visit or death. Moreover, patients who took PPIs prior to their diagnosis of breast cancer but stopped taking them after diagnosis were considered non-PPI users in this study.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated by reference in its entirety to the extent they are not inconsistent with the explicit teachings of this specification.

TABLE 1

Patient Characteristics

| Numerical measure | Mean (SD), median | Range |
|---|---|---|
| Age of diagnosis | 58.88 (13.88), 58 | 19-102 |
| Age of last visit or death | 63.04 (14.20), 62 | 21-104 |
| Days of survival | 1259.9 (1337.83), 600 | 0-4000 |

| Categorical measure | n (%) |
|---|---|
| Gender | |
| Male | 48 (0.7%) |
| Female | 6704 (99.3%) |
| Ethnicity | |
| Caucasian | 5295 (78.42%) |
| Africa American | 1340 (19.85%) |
| Others | 117 (1.73%) |
| Types | |
| Luminal | 3195 (47.32%) |
| HER2+ | 235 (3.48%) |
| TNBC | 489 (7.24%) |
| Unknown | 2833 (41.96%) |
| Tumor Stages | |
| Stage 0 | 593 (8.78%) |
| Stage 1 | 1804 (26.72%) |
| Stage 2 | 1215 (17.99%) |
| Stage 3 | 280 (4.15%) |
| Stage 4 | 75 (1.11%) |
| Unknown | 2785 (41.25%) |
| Metastasis | |
| No sign of metastasis | 3397 (50.31%) |
| With metastasis | 217 (3.21%) |
| Not applicable | 3138 (46.48%) |
| Treatments | |
| Chemo only | 1884 (27.90%) |
| Hormone only | 2372 (35.13%) |
| Chemo + Hormone | 551 (8.16%) |
| PPIs | 876 (12.97%) |
| Surgery | 5466 (80.95%) |
| Radiation | 3069 (45.45%) |
| Status | |
| Confirmed Death | 1229 (18.20%) |
| Last visit | 5523 (81.80%) |

*All data were preprocessed.

TABLE 2

Pairwise analysis of different PPIs

| | | Omeprazole | Lansoprazole | Pantoprazole | Rabeprazole | Esomeprazole |
|---|---|---|---|---|---|---|
| No PPI | HR[a] | 0.28 | 0.17 | 0.32 | 0.47 | 0.44 |
| | P[b] | $2.66*10^{-12}$ | $4.37*10^{-5}$ | $6.48*10^{-5}$ | 0.4342 | $2.86*10^{-8}$ |
| Omeprazole | HR | | 0.68 | 1.11 | 1.50 | 1.6 |
| | P | | 0.4776 | 0.7648 | 0.6844 | 0.0488 |
| Lansoprazole | HR | | | 1.43 | 2.13 | 2.57 |
| | P | | | 0.5441 | 0.4893 | 0.0608 |
| Pantoprazole | HR | | | | 1.43 | 1.44 |
| | P | | | | 0.7302 | 0.2784 |
| Rabeprazole | HR | | | | | 0.92 |
| | P | | | | | 0.9348 |

[a]HR, CoxPH Ratio. [b]P, p-value,

TABLE 3

Benefit of PPI usage for patients receiving different treatments

| | Therapeutic subgroups | PPI users (%) | Non-PPI users | CoxPH ratio | p-value |
|---|---|---|---|---|---|
| Chemotherapy | DNA-damaging drugs | 205 (14.19%) | 1240 | 0.44 | $3.54 * 10^{-6}$ |
| | Cross-linkers[a] | 172 (13.68%) | 1085 | 0.50 | $6.46 * 10^{-4}$ |
| | Anthracyclines[b] | 138 (13.17%) | 910 | 0.46 | $5.69 * 10^{-5}$ |
| | Antimitotics[c] | 191 (14.21%) | 1153 | 0.41 | $4.02 * 10^{-7}$ |
| | Anti-metabolites[d] | 12 (8.05%) | 137 | 0.51 | 0.198 |
| Hormonal | ER[e] | 150 (11.05%) | 1208 | 0.36 | $9.21 * 10^{-6}$ |
| | GnRH[f] | 6 (14.63%) | 35 | 0.89 | 0.853 |
| | Aromatase inhibitors[g] | 179 (17.26%) | 858 | 0.65 | 0.0170 |
| | HER2 inhibitor[h] | 51 (13.82%) | 318 | 0.50 | 0.0401 |

[a]Cross-linkers: carboplatin, cisplatin, and cyclophosphamide
[b]Anthracyclines: epirubicin, doxorubicin, and liposomal doxorubicin
[c]Antimitotics: docetaxel, paclitaxel, and vinorelbine
[d]Anti-metabolites: capecitabine, gemcitabine, fluorouracil, and methotrexate
[e]ER: fulvestrant and tamoxifen
[f]GnRH: goserelin and leuprolide
[g]Aromatase inhibitors: anastrozole, exemestane, and letrozole
[h]HER2 inhibitor: Trastuzumb

TABLE 4

Pairwise comparison of PPIs on outcome in Caucasian and African American Patients

| | | Omeprazole | Lansoprazole | Pantoprazole | Rabeprazole | Esomeprazole |
|---|---|---|---|---|---|---|
| No PPI (AA) | HR | 0.33 | $1.09*10^{-7}$ | 0.59 | NA[a] | 0.49 |
| | P | $6.42*10^{-4}$ | 0.016 | 0.16 | NA | $2.40*10^{-4}$ |
| No PPI (CA) | HR | 0.27 | 0.18 | 0.18 | 0.5031 | 0.35 |
| | P | $1.42*10^{-9}$ | $1.01*10^{-3}$ | $9.05*10^{-5}$ | 0.48 | $3.08*10^{-6}$ |
| Omeprazole (AA) | HR | | $3.99*10^{-9}$ | 1.85 | NA | 1.47 |
| | P | | 0.15 | 0.22 | NA | 0.31 |
| Omeprazole (CA) | HR | | 0.81 | 0.66 | 1.77 | 1 34 |
| | P | | 0.74 | 0.44 | 0.57 | 0.37 |
| Lansoprazole (AA) | HR | | | $9.89*10^{8}$ | NA | $7.79*10^{7}$ |
| | P | | | 0.05 | NA | 0.08 |
| Lansoprazole (CA) | HR | | | 0.59 | 1.99 | 1.74 |
| | P | | | 0.49 | 0.55 | 0.37 |
| Pantoprazole (AA) | HR | | | | NA | 0.84 |
| | P | | | | NA | 0.68 |
| Pantoprazoie (CA) | HR | | | | 2.57 | 2.08 |
| | P | | | | 0.38 | 0.18 |
| Rabeprazole (AA) | HR | | | | | NA |
| | P | | | | | NA |
| Rabeprazole ((’A) | BR | | | | | 0.66 |
| | P | | | | | 0.68 |

[a]NA, not available. No African American patients used rabeprazole.

We claim:

1. A method of treating breast cancer, comprising the steps of:

administering to a patient diagnosed with breast cancer at least one therapeutically effective dose of a composition comprising: at least one proton pump inhibitor and at least one poly ADP ribose polymerase (PARP) inhibitor.

2. The method of claim 1, wherein the at least one proton pump inhibitor is at least one agent selected from the group consisting of: lansoprazole, omeprazole, pantoprazole, rabeprazole, anaprazole, tenatoprazole, ilaprazole, a metabolite thereof, a R- or S-enantiomer thereof, and a pharmaceutically acceptable salt thereof.

3. The method of claim 1, further comprising treating the patient with at least one therapeutically effective dose of at least one agent selected from the group consisting of: doxorubicin, bleomycin, vinblastine, paclitaxel, mitoxantrone, cisplatine, $H_2O_2$, UVB, and ionizing radiation.

4. The method of claim 3, wherein the patient is treated with at least one therapeutically effective dose of doxorubicin or ionizing radiation.

5. The method according to claim 1, wherein the at least one PARP inhibitor is at least one agent selected from the group consisting of: olaparib, niraparib, iniparib, talazoparib, veliparib, rucaparib, or metabolites thereof, or R- or S-enantiomers thereof, or a pharmaceutically acceptable salt thereof.

6. The method of claim 2, wherein the at least one proton pump inhibitor is at least one agent selected from the group consisting of: lansoprazole, omeprazole, pantoprazole, rabeprazole, anaprazole, tenatoprazole, ilaprazole, 5-hydroxy lansoprazole sulfide, esomeprazole, and dexlansoprazole.

7. The method of claim 6, wherein the at least one agent is lansoprazole or 5-hydroxy lansoprazole sulfide.

8. The method of claim 1, wherein the at least one proton pump inhibitor is at least one agent selected from the group consisting of: lansoprazole, omeprazole, pantoprazole, rabeprazole, anaprazole, tenatoprazole, ilaprazole, 5-hydroxy lansoprazole sulfide, esomeprazole, and dexlansoprazole, and wherein the at least one PARP inhibitor is at least one agent selected from the group consisting of: olaparib, talazoparib, niraparib, and rucaparib.

9. The method of claim 1, wherein the at least one proton pump inhibitor is at least one agent selected from the group consisting of: lansoprazole, omeprazole, pantoprazole, rabeprazole, and esomeprazole, and wherein the at least one PARP inhibitor is at least one agent selected from the group consisting of: olaparib and talazoparib.

10. The method of claim 1, wherein the at least one proton pump inhibitor is at least one agent selected from the group consisting of: lansoprazole, omeprazole, pantoprazole, rabeprazole, and esomeprazole, and wherein the at least one PARP inhibitor is at least one agent selected from the group consisting of: olaparib and talazoparib.

11. The method of claim 1, wherein the at least one proton pump inhibitor is at least one agent selected from the group consisting of: lansoprazole, 5-hydroxy lansoprazole sulfide, and omeprazole, and wherein the at least one PARP inhibitor is at least one agent selected from the group consisting of: olaparib and talazoparib.

12. The method of claim 1, wherein the at least one PARP inhibitor is olaparib or talazoparib.

* * * * *